(12) United States Patent
Anderson et al.

(10) Patent No.: US 7,196,200 B2
(45) Date of Patent: Mar. 27, 2007

(54) ANTIBACTERIAL COMPOUNDS

(75) Inventors: David D. Anderson, Kenosha, WI (US); Bruce A. Beutel, Libertyville, IL (US); Curt S. Cooper, Vernon Hills, IL (US); Yu-Gui Gu, Libertyville, IL (US); Mira M. Hinman, Libertyville, IL (US); Douglas M. Kalvin, Buffalo Grove, IL (US); Robert F. Keyes, Kenosha, WI (US); Xenia B. Searle, Grayslake, IL (US); Rolf Wagner, Gurnee, IL (US)

(73) Assignee: Abbott Laboratories, Abbott Park, IL (US)

( * ) Notice: Subject to any disclaimer, the term of this patent is extended or adjusted under 35 U.S.C. 154(b) by 352 days.

(21) Appl. No.: 10/762,002

(22) Filed: Jan. 21, 2004

(65) Prior Publication Data

US 2005/0159423 A1    Jul. 21, 2005

(51) Int. Cl.
*C07D 277/60*    (2006.01)
*A01N 43/78*    (2006.01)
(52) U.S. Cl. .................. 548/148; 548/122; 548/146; 548/152
(58) Field of Classification Search ............ 548/122, 548/146, 148, 152; 514/365, 367
See application file for complete search history.

(56) References Cited

FOREIGN PATENT DOCUMENTS

WO    WO/05 /75477    *    8/2005

* cited by examiner

*Primary Examiner*—James O. Wilson
*Assistant Examiner*—Paul V. Ward
(74) *Attorney, Agent, or Firm*—B. Gregory Donner

(57) ABSTRACT

Bacterial protein synthesis-inhibiting compounds having formula (I)

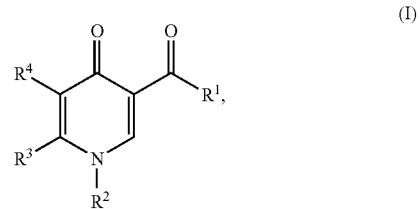

and salts, prodrugs, and salts of prodrugs thereof, processes for making the compounds and intermediates in the processes, compositions containing the compounds, and methods of using the compounds are disclosed.

7 Claims, No Drawings

ANTIBACTERIAL COMPOUNDS

FIELD OF THE INVENTION

This invention pertains to compounds which inhibit bacterial protein synthesis, processes for making the compounds and intermediates in the processes, compositions containing the compounds, and uses for the compounds.

BACKGROUND OF THE INVENTION

Because the effectiveness of many drugs currently available for treating bacterial infections can be compromised by the emergence of drug-resistant bacteria, novel antibacterials would be useful for their therapeutic value and their contribution to the antibacterial arts.

SUMMARY OF THE INVENTION

Accordingly, one embodiment of this invention pertains to compounds, and salts, prodrugs, salts of prodrugs, and metabolites thereof, which inhibit bacterial protein synthesis, the compounds having formula (I)

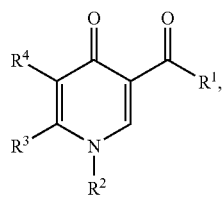

(I)

in which $R^1$ is —OH, —OR$^5$, —NH$_2$, —NHR$^5$, or —N(R$^5$)$_2$; $R^2$ is hydrogen, tert-butyl, —O(allyl), (4-methoxyphenyl)methyl, or (2,4-dimethoxyphenyl)methyl; $R^3$ and $R^4$ together are thiazole or pyrimidine, each of which is substituted with one or two independently selected $R^6$, $R^7$, $R^8$, $R^9$, $R^{10}$, $R^{11}$, —OR$^6$, —O(CH$_2$)R$^7$, —O(CH$_2$)R$^8$, —OR$^9$, —O(CH$_2$)R$^{10}$, —O(CH$_2$)R$^{11}$, —SR$^6$, —S(CH$_2$)R$^7$, —S(CH$_2$)R$^8$, —SR$^9$, —S(CH$_2$)R$^{10}$, —S(CH$_2$)R$^{11}$, —S(O)R$^6$, —S(O)(CH$_2$)R$^7$, —S(O)(CH$_2$)R$^8$, —S(O)R$^9$, —S(O)(CH$_2$)R$^{10}$, —S(O)(CH$_2$)R$^{11}$, —SO$_2$R$^6$, —SO$_2$(CH$_2$)R$^7$, —SO$_2$(CH$_2$)R$^8$, —SO$_2$R$^9$, —SO$_2$(CH$_2$)R$^{10}$, —SO$_2$(CH$_2$)R$^{11}$, —CO(O)R$^6$, —C(O)OR$^7$, —C(O)OR$^8$, —CO(O)R$^9$, —C(O)OR$^{10}$, —C(O)OR$^{11}$, —NH$_2$, —NHR$^6$, —NHR$^7$, —NHR$^8$, —NHR$^9$, —NHR$^{10}$, —NHR$^{11}$, —NHC(O)R$^6$, —NHC(O)R$^7$, —NHC(O)R$^8$, —NHC(O)R$^9$, —NHC(O)R$^{10}$, —NHC(O)R$^{11}$, —NHC(O)OR$^6$, —NHC(O)OR$^7$, —NHC(O)OR$^8$, —NHC(O)OR$^9$, —NHC(O)OR$^{10}$, —NHC(O)OR$^{11}$, —NHSO$_2$R$^6$, —NHSO$_2$R$^7$, —NHSO$_2$R$^8$, —NHSO$_2$R$^9$, —NHSO$_2$R$^{10}$, —NHSO$_2$R$^{11}$, —N(R$^6$)$_2$, —N(R$^7$)$_2$, —N(R$^8$)$_2$, —N(R$^9$)$_2$, —N(R$^{10}$)$_2$, or —N(R$^{11}$)$_2$ substituents; $R^5$ is C$_1$-alkyl, C$_2$-alkyl, C$_3$-alkyl, C$_4$-alkyl, C$_5$-alkyl, or C$_6$-alkyl; $R^6$ is C$_1$-alkyl, C$_2$-alkyl, C$_3$-alkyl, C$_4$-alkyl, C$_5$-alkyl, or C$_6$-alkyl, each of which is unsubstituted or substituted with one —F, —Cl, —Br, —I, —OH, —OR$^{6a}$, —NH$_2$, —NHR$^{6a}$, —N(R$^{6a}$)$_2$, R$^{12}$, R$^{13}$, or R$^{14}$ substituent; $R^{6a}$ is C$_1$-alkyl, C$_2$-alkyl, C$_3$-alkyl, C$_4$-alkyl, C$_5$-alkyl, C$_6$-alkyl, or R$^{6b}$; R$^{6b}$ is C$_1$-alkyl, C$_2$-alkyl, C$_3$-alkyl, C$_4$-alkyl, C$_5$-alkyl, or C$_6$-alkyl, each of which is substituted with one or two independently selected —F, —Cl, —Br, —I, —OH, =O, —OR$^{6c}$, —NH$_2$, —NHR$^{6c}$, —N(R$^{6c}$)$_2$, or R$^{6d}$ substituents; R$^{6c}$ is C$_1$-alkyl, C$_2$-alkyl, C$_3$-alkyl, C$_4$-alkyl, C$_5$-alkyl, or C$_6$-alkyl; R$^{6d}$ is phenyl, furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl; R$^7$ is C$_2$-alkenyl, C$_3$-alkenyl, C$_4$-alkenyl, C$_5$-alkenyl, or C$_6$-alkenyl, each of which is unsubstituted or substituted with one —F, —Cl, —Br, —I, —OH, —OR$^{7a}$, —NH$_2$, —NHR$^{7a}$, —N(R$^{7a}$)$_2$, R$^{12}$, R$^{13}$, or R$^{14}$ substituent; R$^{7a}$ is C$_1$-alkyl, C$_2$-alkyl, C$_3$-alkyl, C$_4$-alkyl, C$_5$-alkyl, or C$_6$-alkyl, or R$^{7b}$; R$^{7b}$ is C$_1$-alkyl, C$_2$-alkyl, C$_3$-alkyl, C$_4$-alkyl, C$_5$-alkyl, or C$_6$-alkyl, each of which is substituted with one or two independently selected —F, —Cl, —Br, —I, —OH, =O, —OR$^{7c}$, —NH$_2$, —NHR$^{7c}$, —N(R$^{7c}$)$_2$, or R$^{7d}$ substituents; R$^{7c}$ is C$_1$-alkyl, C$_2$-alkyl, C$_3$-alkyl, C$_4$-alkyl, C$_5$-alkyl, or C$_6$-alkyl; R$^{7d}$ is phenyl, furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl; R$^8$ is C$_2$-alkynyl, C$_3$-alkynyl, C$_4$-alkynyl, C$_5$-alkynyl, or C$_6$-alkynyl, each of which is unsubstituted or substituted with one —F, —Cl, —Br, —I, —OH, —OR$^{8a}$, —NH$_2$, —NHR$^{8a}$, —N(R$^{8a}$)$_2$, R$^{12}$, R$^{13}$, or R$^{14}$ substituent; R$^{8a}$ is C$_1$-alkyl, C$_2$-alkyl, C$_3$-alkyl, C$_4$-alkyl, C$_5$-alkyl, C$_6$-alkyl, or R$^{8b}$; R$^{8b}$ is C$_1$-alkyl, C$_2$-alkyl, C$_3$-alkyl, C$_4$-alkyl, C$_5$-alkyl, or C$_6$-alkyl, each of which is substituted with one or two independently selected —F, —Cl, —Br, —I, —OH, =O, —OR$^{8c}$, —NH$_2$, —NHR$^{8c}$, —N(R$^{8c}$)$_2$, or R$^{8d}$ substituents; R$^{8c}$ is C$_1$-alkyl, C$_2$-alkyl, C$_3$-alkyl, C$_4$-alkyl, C$_5$-alkyl, or C$_6$-alkyl; R$^{8d}$ is phenyl, furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl; R$^9$ is phenyl which is unfused or fused with cyclopentane, cyclohexane, cyclopentene, cyclohexene, benzene, naphthalene, furan, imidazole, isothiazole, isoxazole, oxazole, pyrazine, pyrazole, pyridazine, pyridine, pyrimidine, pyrrole, thiazole, or thiophene, in which each ring is unsubstituted or substituted with one or two or three or four independently selected R$^{9a}$, —F, —Cl, —Br, —I, —CN, —OH, —OR$^{9a}$, —NH$_2$, —NHR$^{9a}$, —N(R$^{9a}$)$_2$, —NO$_2$, —CF$_3$, —OCF$_3$, —SR$^{9a}$, —S(O)R$^{9a}$, —SO$_2$R$^{9a}$, —C(O)R$^{9a}$, —C(O)OH, —C(O)OR$^{9a}$, —C(O)NH$_2$, —C(O)NHR$^{9a}$, —C(O)N(R$^{9a}$)$_2$, R$^{15}$, or R$^{16}$ substituents; R$^{9a}$ is C$_1$-alkyl, C$_2$-alkyl, C$_3$-alkyl, C$_4$-alkyl, C$_5$-alkyl, C$_6$-alkyl, or R$^{9b}$; R$^{9b}$ is C$_1$-alkyl, C$_2$-alkyl, C$_3$-alkyl, C$_4$-alkyl, C$_5$-alkyl, or C$_6$-alkyl, each of which is substituted with one or two independently selected —F, —Cl, —Br, —I, —OH, =O, —OR$^{9c}$, —NH$_2$, —NHR$^{9c}$, —N(R$^{9c}$)$_2$, or R$^{9d}$ substituents; R$^{9c}$ is C$_1$-alkyl, C$_2$-alkyl, C$_3$-alkyl, C$_4$-alkyl, C$_5$-alkyl, or C$_6$-alkyl; R$^{9d}$ is phenyl, furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl; R$^{10}$ is furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl, each of which is unfused or fused with benzene, naphthalene, furan, imidazole, isothiazole, isoxazole, oxazole, pyrazine, pyrazole, pyridazine, pyridine, pyrimidine, pyrrole, thiazole, or thiophene, in which each ring is unsubstituted or substituted with one or two or three independently selected R$^{10a}$, —F, —Cl, —Br, —I, —CN, —OH, —OR$^{10a}$, —NH$_2$, —NHR$^{10a}$, —N(R$^{10a}$)$_2$, —NO$_2$, —CF$_3$, —OCF$_3$, —SR$^{10a}$, —S(O)R$^{10a}$, —SO$_2$R$^{10a}$, —C(O)R$^{10a}$, —C(O)OH, —C(O)OR$^{10a}$, —C(O)NH$_2$, —C(O)NHR$^{10a}$, —C(O)N(R$^{10a}$)$_2$, R$^{15}$, or R$^{16}$ substituents; R$^{10a}$ is C$_1$-alkyl, C$_2$-alkyl, C$_3$-alkyl, C$_4$-alkyl, C$_5$-alkyl, C$_6$-alkyl, or R$^{10b}$; R$^{10b}$ is C$_1$-alkyl, C$_2$-alkyl, C$_3$-alkyl, C$_4$-alkyl, C$_5$-alkyl, or C$_6$-alkyl, each of which is substituted with one or two independently selected —F, —Cl, —Br, —I, —OH, =O, —OR$^{10c}$, —NH$_2$, —NHR$^{10c}$, —N(R$^{10c}$)$_2$, or R$^{10d}$ substituents; R$^{10c}$ is C$_1$-alkyl, C$_2$-alkyl, C$_3$-alkyl, C$_4$-alkyl, C$_5$-alkyl, or C$_6$-alkyl; R$^{10d}$ is phenyl, furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl; R$^{11}$ is aziridinyl, azetidinyl, pyrrolidinyl, piperidinyl, or piperazinyl, each of which is unfused or fused with benzene, aziridine, azetidine, pyrrolidine, piperidine, or piperazine, in which each ring is unsubstituted or substituted with one or two or three independently selected R$^{11a}$, —F, —Cl, —Br, —I, —CN, —OH, =O, —OR$^{11a}$, —NH$_2$, —NHR$^{11a}$, —N(R$^{11a}$)$_2$, —NO$_2$, —CF$_3$, —OCF$_3$, —SR$^{11a}$, —S(O)R$^{11a}$, —SO$_2$R$^{11a}$, —C(O)R$^{11a}$, —C(O)OH, —C(O)OR$^{11a}$, —C(O)NH$_2$, —C(O)NHR$^{11a}$, —C(O)N(R$^{11a}$)$_2$, R$^{15}$, or R$^{16}$ substituents; R$^{11a}$ is C$_1$-alkyl, C$_2$-alkyl, C$_3$-alkyl, C$_4$-alkyl, C$_5$-alkyl, C$_6$-alkyl, or R$^{11b}$; R$^{11B}$ is C$_1$-alkyl, C$_2$-alkyl, C$_3$-alkyl, C$_4$-alkyl, C$_5$-alkyl, or C$_6$-alkyl, each of which is substituted with one or two independently selected —F, —Cl, —Br, —I, —OH, =O, —OR$^{11c}$, —NH$_2$, —NHR$^{11c}$, —N(R$^{11c}$)$_2$, or R$^{11d}$ substituents; R$^{11c}$ is C$_1$-alkyl, C$_2$-alkyl, C$_3$-alkyl, C$_4$-alkyl, C$_5$-alkyl, or C$_6$-alkyl; R$^{11d}$ is phenyl, furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl; R$^{12}$ is phenyl which is unfused or fused with cyclopentane, cyclohexane, cyclopentene, cyclohexene, benzene, naphthalene, furan, imidazole, isothiazole, isoxazole, oxazole, pyrazine, pyrazole, pyridazine, pyridine, pyrimidine, pyrrole, thiazole, or thiophene, in which each ring is unsubstituted or substituted with one or two or three or four independently selected R$^{12a}$, —F, —Cl, —Br, —I, —CN, —OH, —OR$^{12a}$, —NH$_2$, —NHR$^{12a}$, —N(R$^{12a}$)$_2$, —NO$_2$, —CF$_3$, —OCF$_3$, —SR$^{12a}$, —S(O)R$^{12a}$, —SO$_2$R$^{12a}$, —C(O)R$^{12a}$, —C(O)OH, —C(O)OR$^{12a}$, —C(O)NH$_2$, —C(O)NHR$^{12a}$, —C(O)N(R$^{12a}$)$_2$, R$^{15}$, or R$^{16}$ substituents; R$^{12a}$ is C$_1$-alkyl, C$_2$-alkyl, C$_3$-alkyl, C$_4$-alkyl, C$_5$-alkyl, C$_6$-alkyl, or R$^{12b}$; R$^{12b}$ is C$_1$-alkyl, C$_2$-alkyl, C$_3$-alkyl, C$_4$-alkyl, C$_5$-alkyl, or C$_6$-alkyl, each of which is substituted with one or two independently selected —F, —Cl, —Br, —I, —OH, =O, —OR$^{12a}$, —NH$_2$, —NHR$^{12c}$, —N(R$^{12c}$)$_2$, or R$^{12d}$ substituents; R$^{12c}$ is C$_1$-alkyl, C$_2$-alkyl, C$_3$-alkyl, C$_4$-alkyl, C$_5$-alkyl, or C$_6$-alkyl; R$^{12d}$ is phenyl, furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl; R$^{13}$ is furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl, each of which is unfused or fused with benzene, naphthalene, furan, imidazole, isothiazole, isoxazole, oxazole, pyrazine, pyrazole, pyridazine, pyridine, pyrimidine, pyrrole, thiazole, or thiophene, in which each ring is unsubstituted or substituted with one or two or three independently selected R$^{13a}$, —F, —Cl, —Br, —I, —CN, —OH, —OR$^{13a}$, —NH$_2$, —NHR$^{13a}$, —N(R$^{13a}$)$_2$, —NO$_2$, —CF$_3$, —OCF$_3$, —SR$^{13a}$, —S(O)R$^{13a}$, —SO$_2$R$^{13a}$, —C(O)R$^{13a}$, —C(O)OH, —C(O)OR$^{13a}$, —C(O)NH$_2$, —C(O)NHR$^{13a}$, —C(O)N(R$^{13a}$)$_2$, R$^{15}$, or R$^{16}$ substituents; R$^{13a}$ is C$_1$-alkyl, C$_2$-alkyl, C$_3$-alkyl, C$_4$-alkyl, C$_5$-alkyl, C$_6$-alkyl, or R$^{13b}$; R$^{13b}$ is C$_1$-alkyl, C$_2$-alkyl, C$_3$-alkyl, C$_4$-alkyl, C$_5$-alkyl, or C$_6$-alkyl, each of which is substituted with one or two independently selected —F, —Cl, —Br, —I, —OH, =O, —OR$^{13c}$, —NH$_2$, —NHR$^{13c}$, —N(R$^{13c}$)$_2$, or R$^{13d}$ substituents; R$^{13c}$ is C$_1$-alkyl, C$_2$-alkyl, C$_3$-alkyl, C$_4$-alkyl, C$_5$-alkyl, or C$_6$-alkyl; R$^{13d}$ is phenyl, furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl; R$^{14}$ is aziridinyl, azetidinyl, pyrrolidinyl, piperidinyl, or piperazinyl, each of which is unfused or fused with benzene, aziridine, azetidine, pyrrolidine, piperidine, or piperazine, in which each ring is unsubstituted or substituted with one or two or three independently selected R$^{14a}$, —F, —Cl, —Br, —I, —CN, —OH, =O, —OR$^{14a}$, —NH$_2$, —NHR$^{14a}$, —N(R$^{14a}$)$_2$, —NO$_2$, —CF$_3$, —OCF$_3$, —SR$^{14a}$, —S(O)R$^{14a}$, —SO$_2$R$^{14a}$, —C(O)R$^{14a}$, —C(O)OH, —C(O)OR$^{14a}$, —C(O)NH$_2$, —C(O)NHR$^{14a}$, —C(O)N(R$^{14a}$)$_2$, R$^{15}$, or R$^{16}$ substituents; R$^{14a}$ is C$_1$-alkyl, C$_2$-alkyl, C$_3$-alkyl, C$_4$-alkyl, C$_5$-alkyl, C$_6$-alkyl, or R$^{14b}$; R$^{14b}$ is C$_1$-alkyl, C$_2$-alkyl, C$_3$-alkyl, C$_4$-alkyl, C$_5$-alkyl, or C$_6$-alkyl, each of which is substituted with one or two independently selected —F, —Cl, —Br, —I, —OH, =O, —OR$^{14c}$, —NH$_2$, —NHR$^{14c}$, —N(R$^{14c}$)$_2$, or R$^{14d}$ substituents; R$^{14c}$ is C$_1$-alkyl, C$_2$-alkyl, C$_3$-alkyl, C$_4$-alkyl, C$_5$-alkyl, or C$_6$-alkyl; R$^{14d}$ is phenyl, furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl; R$^{15}$ is phenyl which is unsubstituted or substituted with one or two or three or four independently selected R$^{15a}$, —F, —Cl, —Br, —I, —CN, —OH, —OR$^{15a}$, —NH$_2$, —NHR$^{15a}$, —N(R$^{15a}$)$_2$, —NO$_2$, —CF$_3$, —OCF$_3$, —SR$^{15a}$, —S(O)R$^{15a}$, —SO$_2$R$^{15a}$, —C(O)R$^{15a}$, —C(O)OH, —C(O)OR$^{15a}$, —C(O)NH$_2$, —C(O)NHR$^{15a}$, or —C(O)N(R$^{15a}$)$_2$ substituents; R$^{15a}$ is C$_1$-alkyl, C$_2$-alkyl, C$_3$-alkyl, C$_4$-alkyl, C$_5$-alkyl, or C$_6$-alkyl, or R$^{15b}$; R$^{15b}$ is C$_1$-alkyl, C$_2$-alkyl, C$_3$-alkyl, C$_4$-alkyl, C$_5$-alkyl, or C$_6$-alkyl, each of which is substituted with one or two independently selected —F, —Cl, —Br, —I, —OH, =O, —OR$^{15c}$, —NH$_2$, —NHR$^{15c}$, N(R$^{15c}$)$_2$, or R$^{15d}$ substituents; R$^{15c}$ is C$_1$-alkyl, C$_2$-alkyl, C$_3$-alkyl, C$_4$-alkyl, C$_5$-alkyl, or C$_6$-alkyl; R$^{15d}$ is phenyl, furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl; R$^{16}$ is furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl, each of which is unsubstituted or substituted with one or two or three independently selected R$^{16a}$, —F, —Cl, —Br, —I, —CN, —OH, —OR$^{16a}$, —NH$_2$, —NHR$^{16a}$, —N(R$^{16a}$)$_2$, —NO$_2$, —CF$_3$, —OCF$_3$, —SR$^{16a}$, —S(O)R$^{16a}$, —SO$_2$R$^{16a}$, —C(O)R$^{16a}$, —C(O)OH, —C(O)OR$^{16a}$, —C(O)NH$_2$, —C(O)NHR$^{16a}$, or —C(O)N(R$^{16a}$)$_2$ substituents; R$^{16a}$ is C$_1$-alkyl, C$_2$-alkyl, C$_3$-alkyl, C$_4$-alkyl, C$_5$-alkyl, C$_6$-alkyl, or R$^{16b}$; R$^{16b}$ is C$_1$-alkyl, C$_2$-alkyl, C$_3$-alkyl, C$_4$-alkyl, C$_5$-alkyl, or C$_6$-alkyl, each of which is substituted with one or two independently selected —F, —Cl, —Br, —I, —OH, —OR$^{16c}$, =O, —NH$_2$, —NHR$^{16c}$, —N(R$^{16c}$)$_2$, or R$^{16d}$ substituents; R$^{16c}$ is C$_1$-alkyl, C$_2$-alkyl, C$_3$-alkyl, C$_4$-alkyl, C$_5$-alkyl, or C$_6$-alkyl; and R$^{16d}$ is phenyl, furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl.

Another embodiment of this invention pertains to processes for making the compounds of this invention having formula (I), and salts, prodrugs, and salts of prodrugs thereof.

Still another embodiment of this invention pertains to intermediates which are used in the processes for making the compounds of this invention having formula (I), and salts, prodrugs, and salts of prodrugs thereof.

Still yet another embodiment of this invention pertains to metabolites of the compounds of this invention having formula (I), and salts, prodrugs, and salts of prodrugs thereof.

Still even yet another embodiment of this invention pertains to compositions for inhibiting bacterial protein synthesis in vitro, the compositions comprising a therapeutically effective amount of a compound of this invention having formula (I), or a salt, prodrug, or salt of a prodrug thereof, and an excipient.

Still even yet another embodiment of this invention pertains to compositions for inhibiting bacterial protein synthesis in vitro, the compositions comprising therapeutically effective amounts of more than one compound of this invention having formula (I), or salts, prodrugs, or salts of prodrugs thereof, and an excipient.

Still even yet another embodiment of this invention pertains to compositions for inhibiting antibacterial-resistant bacterial protein synthesis in vitro, the compositions comprising a therapeutically effective amount of a compound of this invention having formula (I), or a salt, prodrug, or salt of a prodrug thereof, and an excipient.

Still even yet another embodiment of this invention pertains to compositions for inhibiting antibacterial-resistant bacterial protein synthesis in vitro, the compositions comprising therapeutically effective amounts of more than one compound of this invention having formula (I), or salts, prodrugs, or salts of prodrugs thereof, and an excipient.

Still even yet another embodiment of this invention pertains to compositions for inhibiting quinolone-resistant bacterial protein synthesis in vitro, the compositions comprising a therapeutically effective amount of a compound of this invention having formula (I), or a salt, prodrug, or salt of a prodrug thereof, and an excipient.

Still even yet another embodiment of this invention pertains to compositions for inhibiting quinolone-resistant bacterial protein synthesis in vitro, the compositions comprising therapeutically effective amounts of more than one compound of this invention having formula (I), or salts, prodrugs, or salts of prodrugs thereof, and an excipient.

Still even yet another embodiment of this invention pertains to compositions for inhibiting cell-free bacterial protein synthesis in vitro, the compositions comprising a therapeutically effective amount of a compound of this invention having formula (I), or a salt, prodrug, or salt of a prodrug thereof, and an excipient.

Still even yet another embodiment of this invention pertains to compositions for inhibiting cell-free bacterial protein synthesis in vitro, the compositions comprising therapeutically effective amounts of more than one compound of this invention having formula (I), or salts, prodrugs, or salts of prodrugs thereof, and an excipient.

Still even yet another embodiment of this invention pertains to compositions for inhibiting cell-free, antibacterial-resistant bacterial protein synthesis in vitro, the compositions comprising a therapeutically effective amount of a compound of this invention having formula (I), or a salt, prodrug, or salt of a prodrug thereof, and an excipient.

Still even yet another embodiment of this invention pertains to compositions for inhibiting cell-free, antibacterial-resistant bacterial protein synthesis in vitro, the compositions comprising more than one compound of this invention having formula (I), or salts, prodrugs, or salts of prodrugs thereof, and an excipient.

Still even yet another embodiment of this invention pertains to compositions for inhibiting cell-free, quinolone-resistant bacterial protein synthesis in vitro, the compositions comprising a therapeutically effective amount of a compound of this invention having formula (I), or a salt, prodrug, or salt of a prodrug thereof, and an excipient.

Still even yet another embodiment of this invention pertains to compositions for inhibiting cell-free, quinolone-resistant bacterial protein synthesis in vitro, the compositions comprising therapeutically effective amounts of more than one compound of this invention having formula (I), or salts, prodrugs, or salts of prodrugs thereof, and an excipient.

Still even yet another embodiment of this invention pertains to compositions for inhibiting bacterial growth in vitro, the compositions comprising a therapeutically effective amount of a compound of this invention having formula (I), or a salt, prodrug, or salt of a prodrug thereof, and an excipient.

Still even yet another embodiment of this invention pertains to compositions for inhibiting bacterial growth in vitro, the compositions comprising therapeutically effective amounts of more than one compound of this invention having formula (I), or salts, prodrugs, or salts of prodrugs thereof, and an excipient.

Still even yet another embodiment of this invention pertains to compositions for inhibiting antibacterial-resistant bacterial growth in vitro, the compositions comprising a therapeutically effective amount of a compound of this invention having formula (I), or a salt, prodrug, or salt of a prodrug thereof, and an excipient.

Still even yet another embodiment of this invention pertains to compositions for inhibiting antibacterial-resistant bacterial growth in vitro, the compositions comprising therapeutically effective amounts of more than one compound of this invention having formula (I), or salts, prodrugs, or salts of prodrugs thereof, and an excipient.

Still even yet another embodiment of this invention pertains to compositions for inhibiting quinolone-resistant bacterial growth in vitro, the compositions comprising a therapeutically effective amount of a compound of this invention having formula (I), or a salt, prodrug, or salt of a prodrug thereof, and an excipient.

Still even yet another embodiment of this invention pertains to compositions for inhibiting quinolone-resistant bacterial growth in vitro, the compositions comprising therapeutically effective amounts of more than one compound of this invention having formula (I), or salts, prodrugs, or salts of prodrugs thereof, and an excipient.

Still even yet another embodiment of this invention pertains to compositions for inhibiting cell-free bacterial growth in vitro, the compositions comprising a therapeutically effective amount of a compound of this invention having formula (I), or a salt, prodrug, or salt of a prodrug thereof, and an excipient.

Still even yet another embodiment of this invention pertains to compositions for inhibiting cell-free bacterial growth in vitro, the compositions comprising therapeutically effective amounts of more than one compound of this invention having formula (I), or salts, prodrugs, or salts of prodrugs thereof, and an excipient.

Still even yet another embodiment of this invention pertains to compositions for inhibiting cell-free, antibacterial-resistant bacterial growth in vitro, the compositions comprising a therapeutically effective amount of a compound of this invention having formula (I), or a salt, prodrug, or salt of a prodrug thereof, and an excipient.

Still even yet another embodiment of this invention pertains to compositions for inhibiting cell-free, antibacterial-resistant bacterial growth in vitro, the compositions comprising therapeutically effective amounts of more than one compound of this invention having formula (I), or salts, prodrugs, or salts of prodrugs thereof, and an excipient.

Still even yet another embodiment of this invention pertains to compositions for inhibiting cell-free, quinolone-resistant bacterial growth in vitro, the compositions comprising a therapeutically effective amount of a compound of this invention having formula (I), or a salt, prodrug, or salt of a prodrug thereof, and an excipient.

Still even yet another embodiment of this invention pertains to compositions for inhibiting cell-free, quinolone-resistant bacterial growth in vitro, the compositions comprising therapeutically effective amounts of more than one compound of this invention having formula (I), or salts, prodrugs, or salts of prodrugs thereof, and an excipient.

Still even yet another embodiment of this invention pertains to compositions for inhibiting bacterial protein synthesis in a fish or a mammal, the compositions comprising a therapeutically effective amount of a compound of this invention having formula (I), or a salt, prodrug, or salt of a prodrug thereof, and an excipient.

Still even yet another embodiment of this invention pertains to compositions for inhibiting bacterial protein synthesis in a fish or a mammal, the compositions comprising therapeutically effective amounts of more than one compound of this invention having formula (I), or salts, prodrugs, or salts of prodrugs thereof, and an excipient.

Still even yet another embodiment of this invention pertains to compositions for inhibiting antibacterial-resistant bacterial protein synthesis in a fish or a mammal, the compositions comprising a therapeutically effective amount of a compound of this invention having formula (I), or a salt, prodrug, or salt of a prodrug thereof, and an excipient.

Still even yet another embodiment of this invention pertains to compositions for inhibiting antibacterial-resistant bacterial protein synthesis in a fish or a mammal, the compositions comprising therapeutically effective amounts of more than one compound of this invention having formula (I), or salts, prodrugs, or salts of prodrugs thereof, and an excipient.

Still even yet another embodiment of this invention pertains to compositions for inhibiting quinolone-resistant bacterial protein synthesis in a fish or a mammal, the compositions comprising a therapeutically effective amount of a compound of this invention having formula (I), or a salt, prodrug, or salt of a prodrug thereof, and an excipient.

Still even yet another embodiment of this invention pertains to compositions for inhibiting quinolone-resistant bacterial protein synthesis in a fish or a mammal, the compositions comprising therapeutically effective amounts of more than one compound of this invention having formula (I), or salts, prodrugs, or salts of prodrugs thereof, and an excipient.

Still even yet another embodiment of this invention pertains to compositions for inhibiting bacterial growth in a fish or a mammal, the compositions comprising a therapeutically effective amount of a compound of this invention having formula (I), or a salt, prodrug, or salt of a prodrug thereof, and an excipient.

Still even yet another embodiment of this invention pertains to compositions for inhibiting bacterial growth in a fish or a mammal, the compositions comprising therapeutically effective amounts of more than one compound of this invention having formula (I), or salts, prodrugs, or salts of prodrugs thereof, and an excipient.

Still even yet another embodiment of this invention pertains to compositions for inhibiting antibacterial-resistant bacterial growth in a fish or a mammal, the compositions comprising a therapeutically effective amount of a compound of this invention having formula (I), or a salt, prodrug, or salt of a prodrug thereof, and an excipient.

Still even yet another embodiment of this invention pertains to compositions for inhibiting antibacterial-resistant bacterial growth in a fish or a mammal, the compositions comprising therapeutically effective amounts of more than one compound of this invention having formula (I), or salts, prodrugs, or salts of prodrugs thereof, and an excipient.

Still even yet another embodiment of this invention pertains to compositions for inhibiting quinolone-resistant bacterial growth in a fish or a mammal, the compositions comprising a therapeutically effective amount of a compound of this invention having formula (I), or a salt, prodrug, or salt of a prodrug thereof, and an excipient.

Still even yet another embodiment of this invention pertains to compositions for inhibiting quinolone-resistant bacterial growth in a fish or a mammal, the compositions comprising therapeutically effective amounts of more than one compound of this invention having formula (I), or salts, prodrugs, or salts of prodrugs thereof, and an excipient.

Still even yet another embodiment of this invention pertains to compositions for treating bacterial infections in a fish or a mammal, the compositions comprising a therapeutically effective amount of a compound of this invention having formula (I), or a salt, prodrug, or salt of a prodrug thereof, and an excipient.

Still even yet another embodiment of this invention pertains to compositions for treating bacterial infections in a fish or a mammal, the compositions comprising therapeutically effective amounts of more than one compound of this invention having formula (I), or salts, prodrugs, or salts of prodrugs thereof, and an excipient.

Still even yet another embodiment of this invention pertains to compositions for treating antibacterial-resistant bacterial infections in a fish or a mammal, the compositions comprising a therapeutically effective amount of a compound of this invention having formula (I), or a salt, prodrug, or salt of a prodrug thereof, and an excipient.

Still even yet another embodiment of this invention pertains to compositions for treating antibacterial-resistant bacterial infections in a fish or a mammal, the compositions comprising therapeutically effective amounts of more than one compound of this invention having formula (I), or salts, prodrugs, or salts of prodrugs thereof, and an excipient.

Still even yet another embodiment of this invention pertains to compositions for treating quinolone-resistant bacterial infections in a fish or a mammal, the compositions comprising a therapeutically effective amount of a compound of this invention having formula (I), or a salt, prodrug, or salt of a prodrug thereof, and an excipient.

Still even yet another embodiment of this invention pertains to compositions for treating quinolone-resistant bacterial infections in a fish or a mammal, the compositions comprising therapeutically effective amounts of more than one compound of this invention having formula (I), or salts, prodrugs, or salts of prodrugs thereof, and an excipient.

Still even yet another embodiment of this invention pertains to methods for inhibiting bacterial protein synthesis in vitro, the methods comprising administering thereto a therapeutically effective amount of a compound of this invention having formula (I), or a salt, prodrug, or salt of a prodrug thereof.

Still even yet another embodiment of this invention pertains to methods for inhibiting bacterial protein synthesis in vitro, the methods comprising administering therapeutically effective amounts of more than one compound of this invention having formula (I), or salts, prodrugs, or salts of prodrugs thereof.

Still even yet another embodiment of this invention pertains to methods for inhibiting antibacterial-resistant bacterial protein synthesis in vitro, the methods comprising administering thereto a therapeutically effective amount of a compound of this invention having formula (I), or a salt, prodrug, or salt of a prodrug thereof.

Still even yet another embodiment of this invention pertains to methods for inhibiting antibacterial-resistant bacterial protein synthesis in vitro, the methods comprising administering therapeutically effective amounts of more than one compound of this invention having formula (I), or salts, prodrugs, or salts of prodrugs thereof.

Still even yet another embodiment of this invention pertains to methods for inhibiting quinolone-resistant bacterial protein synthesis in vitro, the methods comprising administering thereto a therapeutically effective amount of a compound of this invention having formula (I), or a salt, prodrug, or salt of a prodrug thereof.

Still even yet another embodiment of this invention pertains to methods for inhibiting quinolone-resistant bacterial protein synthesis in vitro, the methods comprising administering therapeutically effective amounts of more than one compound of this invention having formula (I), or salts, prodrugs, or salts of prodrugs thereof.

Still even yet another embodiment of this invention pertains to methods for inhibiting cell-free bacterial protein synthesis in vitro, the methods comprising administering thereto a therapeutically effective amount of a compound of this invention having formula (I), or a salt, prodrug, or salt of a prodrug thereof.

Still even yet another embodiment of this invention pertains to methods for inhibiting cell-free bacterial protein synthesis in vitro, the methods comprising administering therapeutically effective amounts of more than one compound of this invention having formula (I), or salts, prodrugs, or salts of prodrugs thereof.

Still even yet another embodiment of this invention pertains to methods for inhibiting cell-free, antibacterial-resistant bacterial protein synthesis in vitro, the methods comprising administering thereto a therapeutically effective amount of a compound of this invention having formula (I), or a salt, prodrug, or salt of a prodrug thereof.

Still even yet another embodiment of this invention pertains to methods for inhibiting cell-free, antibacterial-resistant bacterial protein synthesis in vitro, the methods comprising administering therapeutically effective amounts of more than one compound of this invention having formula (I), or salts, prodrugs, or salts of prodrugs thereof.

Still even yet another embodiment of this invention pertains to methods for inhibiting cell-free, quinolone-resistant bacterial protein synthesis in vitro, the methods comprising administering thereto a therapeutically effective amount of a compound of this invention having formula (I), or a salt, prodrug, or salt of a prodrug thereof.

Still even yet another embodiment of this invention pertains to methods for inhibiting cell-free, quinolone-resistant bacterial protein synthesis in vitro, the methods comprising administering therapeutically effective amounts of more than one compound of this invention having formula (I), or salts, prodrugs, or salts of prodrugs thereof.

Still even yet another embodiment of this invention pertains to methods for inhibiting bacterial growth in vitro, the methods comprising administering thereto a therapeutically effective amount of a compound of this invention having formula (I), or a salt, prodrug, or salt of a prodrug thereof.

Still even yet another embodiment of this invention pertains to methods for inhibiting bacterial growth in vitro, the methods comprising administering therapeutically effective amounts of more than one compound of this invention having formula (I), or salts, prodrugs, or salts of prodrugs thereof.

Still even yet another embodiment of this invention pertains to methods for inhibiting antibacterial-resistant bacterial growth in vitro, the methods comprising administering thereto a therapeutically effective amount of a compound of this invention having formula (I), or a salt, prodrug, or salt of a prodrug thereof.

Still even yet another embodiment of this invention pertains to methods for inhibiting antibacterial-resistant bacterial growth in vitro, the methods comprising administering therapeutically effective amounts of more than one compound of this invention having formula (I), or salts, prodrugs, or salts of prodrugs thereof.

Still even yet another embodiment of this invention pertains to methods for inhibiting quinolone-resistant bacterial growth in vitro, the methods comprising administering thereto a therapeutically effective amount of a compound of this invention having formula (I), or a salt, prodrug, or salt of a prodrug thereof.

Still even yet another embodiment of this invention pertains to methods for inhibiting quinolone-resistant bacterial growth in vitro, the methods comprising administering therapeutically effective amounts of more than one compound of this invention having formula (I), or salts, prodrugs, or salts of prodrugs thereof.

Still even yet another embodiment of this invention pertains to methods for inhibiting cell-free bacterial growth in vitro, the methods comprising administering thereto a therapeutically effective amount of a compound of this invention having formula (I), or a salt, prodrug, or salt of a prodrug thereof.

Still even yet another embodiment of this invention pertains to methods for inhibiting cell-free bacterial growth in vitro, the methods comprising administering therapeutically effective amounts of more than one compound of this invention having formula (I), or salts, prodrugs, or salts of prodrugs thereof.

Still even yet another embodiment of this invention pertains to methods for inhibiting cell-free, antibacterial-resistant bacterial growth in vitro, the methods comprising administering thereto a therapeutically effective amount of a compound of this invention having formula (I), or a salt, prodrug, or salt of a prodrug thereof.

Still even yet another embodiment of this invention pertains to methods for inhibiting cell-free, antibacterial-resistant bacterial growth in vitro, the methods comprising administering therapeutically effective amounts of more than one compound of this invention having formula (I), or salts, prodrugs, or salts of prodrugs thereof.

Still even yet another embodiment of this invention pertains to methods for inhibiting cell-free, quinolone-resistant bacterial growth in vitro, the methods comprising administering thereto a therapeutically effective amount of a compound of this invention having formula (I), or a salt, prodrug, or salt of a prodrug thereof.

Still even yet another embodiment of this invention pertains to methods for inhibiting cell-free, quinolone-resistant bacterial growth in vitro, the methods comprising administering therapeutically effective amounts of more than one compound of this invention having formula (I), or salts, prodrugs, or salts of prodrugs thereof.

Still even yet another embodiment of this invention pertains to methods for inhibiting bacterial protein synthesis in a fish or a mammal, the methods comprising administering thereto a therapeutically effective amount of a compound of this invention having formula (I), or a salt, prodrug, or salt of a prodrug thereof.

Still even yet another embodiment of this invention pertains to methods for inhibiting bacterial protein synthesis in a fish or a mammal, the methods comprising administering therapeutically effective amounts of more than one compound of this invention having formula (I), or salts, prodrugs, or salts of prodrugs thereof.

Still even yet another embodiment of this invention pertains to methods for inhibiting antibacterial-resistant bacterial protein synthesis in a fish or a mammal, the methods comprising administering thereto a therapeutically effective amount of a compound of this invention having formula (I), or a salt, prodrug, or salt of a prodrug thereof.

Still even yet another embodiment of this invention pertains to methods for inhibiting antibacterial-resistant bacterial protein synthesis in a fish or a mammal, the methods comprising administering therapeutically effective amounts of more than one compound of this invention having formula (I), or salts, prodrugs, or salts of prodrugs thereof.

Still even yet another embodiment of this invention pertains to methods for inhibiting quinolone-resistant bacterial protein synthesis in a fish or a mammal, the methods comprising administering thereto a therapeutically effective amount of a compound of this invention having formula (I), or a salt, prodrug, or salt of a prodrug thereof.

Still even yet another embodiment of this invention pertains to methods for inhibiting quinolone-resistant bacterial protein synthesis in a fish or a mammal, the methods comprising administering therapeutically effective amounts of more than one compound of this invention having formula (I), or salts, prodrugs, or salts of prodrugs thereof.

Still even yet another embodiment of this invention pertains to methods for inhibiting bacterial growth in a fish or a mammal, the methods comprising administering thereto a therapeutically effective amount of a compound of this invention having formula (I), or a salt, prodrug, or salt of a prodrug thereof.

Still even yet another embodiment of this invention pertains to methods for inhibiting bacterial growth in a fish or a mammal, the methods comprising administering therapeutically effective amounts of more than one compound of this invention having formula (I), or salts, prodrugs, or salts of prodrugs thereof.

Still even yet another embodiment of this invention pertains to methods for inhibiting antibacterial-resistant bacterial growth in a fish or a mammal, the methods comprising administering thereto a therapeutically effective amount of a compound of this invention having formula (I), or a salt, prodrug, or salt of a prodrug thereof.

Still even yet another embodiment of this invention pertains to methods for inhibiting antibacterial-resistant bacterial growth in a fish or a mammal, the methods comprising administering therapeutically effective amounts of more than one compound of this invention having formula (I), or salts, prodrugs, or salts of prodrugs thereof.

Still even yet another embodiment of this invention pertains to methods for inhibiting quinolone-resistant bacterial growth in a fish or a mammal, the methods comprising administering thereto a therapeutically effective amount of a compound of this invention having formula (I), or a salt, prodrug, or salt of a prodrug thereof.

Still even yet another embodiment of this invention pertains to methods for inhibiting quinolone-resistant bacterial growth in a fish or a mammal, the methods comprising administering therapeutically effective amounts of more than one compound of this invention having formula (I), or salts, prodrugs, or salts of prodrugs thereof.

Still even yet another embodiment of this invention pertains to methods for treating bacterial infections in a fish or a mammal, the methods comprising administering thereto a therapeutically effective amount of a compound of this invention having formula (I), or a salt, prodrug, or salt of a prodrug thereof.

Still even yet another embodiment of this invention pertains to methods for treating bacterial infections in a fish or a mammal, the methods comprising administering therapeutically effective amounts of more than one compound of this invention having formula (I), or salts, prodrugs, or salts of prodrugs thereof.

Still even yet another embodiment of this invention pertains to methods for treating antibacterial-resistant bacterial infections in a fish or a mammal, the methods comprising administering thereto a therapeutically effective amount of a compound of this invention having formula (I), or a salt, prodrug, or salt of a prodrug thereof.

Still even yet another embodiment of this invention pertains to methods for treating antibacterial-resistant bacterial infections in a fish or a mammal, the methods comprising administering therapeutically effective amounts of more than one compound of this invention having formula (I), or salts, prodrugs, or salts of prodrugs thereof.

Still even yet another embodiment of this invention pertains to methods for treating quinolone-resistant bacterial infections in a fish or a mammal, the methods comprising administering thereto a therapeutically effective amount of a compound of this invention having formula (I), or a salt, prodrug, or salt of a prodrug thereof.

Still even yet another embodiment of this invention pertains to methods for treating quinolone-resistant bacterial infections in a fish or a mammal, the methods comprising administering therapeutically effective amounts of more than one compound of this invention having formula (I), or salts, prodrugs, or salts of prodrugs thereof.

Still even yet another embodiment of this invention pertains to use of a compound of this invention having formula (I), or a salt, prodrug, or salt of a prodrug thereof, in the preparation of a composition for the inhibition of bacterial protein synthesis in a fish or a mammal.

Still even yet another embodiment of this invention pertains to use of more than one compound of this invention formula (I), or salts, prodrugs, or salts of prodrugs thereof, in the preparation of a composition for the inhibition of bacterial protein synthesis in a fish or a mammal.

Still even yet another embodiment of this invention pertains to use of a compound of this invention having formula (I), or a salt, prodrug, or salt of a prodrug thereof, in the preparation of a composition for the inhibition of antibacterial-resistant bacterial protein synthesis in a fish or a mammal.

Still even yet another embodiment of this invention pertains to use of more than one compound of this invention having formula (I), or salts, prodrugs, or salts of prodrugs thereof, in the preparation of a composition for the inhibition of antibacterial-resistant bacterial protein synthesis in a fish or a mammal.

Still even yet another embodiment of this invention pertains to use of a compound of this invention having formula (I), or a salt, prodrug, or salt of a prodrug thereof, in the preparation of a composition for the inhibition of quinolone-resistant bacterial protein synthesis in a fish or a mammal.

Still even yet another embodiment of this invention pertains to use of more than one compound of this invention having formula (I), or salts, prodrugs, or salts of prodrugs thereof, in the preparation of a composition for the inhibition of quinolone-resistant bacterial protein synthesis in a fish or a mammal.

Still even yet another embodiment of this invention pertains to use of a compound of this invention having formula (I), or a salt, prodrug, or salt of a prodrug thereof, in the preparation of a composition for the inhibition of bacterial growth in a fish or a mammal.

Still even yet another embodiment of this invention pertains to use of more than one compound of this invention having formula (I), or salts, prodrugs, or salts of prodrugs thereof, in the preparation of a composition for the inhibition of bacterial growth in a fish or a mammal.

Still even yet another embodiment of this invention pertains to use of a compound of this invention having formula (I), or a salt, prodrug, or salt of a prodrug thereof, in the preparation of a composition for the inhibition of antibacterial-resistant bacterial growth in a fish or a mammal.

Still even yet another embodiment of this invention pertains to use of more than one compound of this invention having formula (I), or salts, prodrugs, or salts of prodrugs thereof, in the preparation of a composition for the inhibition of antibacterial-resistant bacterial growth in a fish or a mammal.

Still even yet another embodiment of this invention pertains to use of a compound of this invention having formula (I), or a salt, prodrug, or salt of a prodrug thereof, in the preparation of a composition for the inhibition of quinolone-resistant bacterial growth in a fish or a mammal.

Still even yet another embodiment of this invention pertains to use of more than one compound of this invention having formula (I), or salts, prodrugs, or salts of prodrugs thereof, in the preparation of a composition for the inhibition of quinolone-resistant bacterial growth in a fish or a mammal.

Still even yet another embodiment of this invention pertains to use of a compound of this invention having formula (I), or a salt, prodrug, or salt of a prodrug thereof, in the preparation of a composition for treating bacterial infections in a fish or a mammal.

Still even yet another embodiment of this invention pertains to use of more than one compound of this invention having formula (I), or salts, prodrugs, or salts of prodrugs thereof, in the preparation of a composition for treating bacterial infections in a fish or a mammal.

Still even yet another embodiment of this invention pertains to use of a compound of this invention having formula (I), or a salt, prodrug, or salt of a prodrug thereof, in the preparation of a composition for treating antibacterial-resistant bacterial infections in a fish or a mammal.

Still even yet another embodiment of this invention pertains to use of more than one compound of this invention having formula (I), or salts, prodrugs, or salts of prodrugs thereof, in the preparation of a composition for treating antibacterial-resistant bacterial infections in a fish or a mammal.

Still even yet another embodiment of this invention pertains to use of a compound of this invention having formula (I), or a salt, prodrug, or salt of a prodrug thereof, in the preparation of a composition for treating quinolone-resistant bacterial infections in a fish or a mammal.

Still even yet another embodiment of this invention pertains to use of more than one compound of this invention having formula (I), or salts, prodrugs, or salts of prodrugs thereof, in the preparation of a composition for treating quinolone-resistant bacterial infections in a fish or a mammal.

DETAILED DESCRIPTION OF THE INVENTION

The compounds of this invention are represented by fixed and variable moieties, the latter of which are represented by identifiers (capital letters with numerical and/or alphabetical superscripts) and can be specifically embodied.

It is meant to be understood that a specific embodiment of a variable moiety can be the same or different as another specific embodiment having the same identifier if the possibility of more than one specific embodiment having that identifier exists.

The term "$C_2$-alkenyl" means ethenyl (vinyl).

The term "$C_3$-alkenyl" means 1-propen-1-yl, 1-propen-2-yl (isopropenyl), and 1-propen-3-yl (allyl).

The term "$C_4$-alkenyl" means 1-buten-1-yl, 1-buten-2-yl, 1,3-butadien-1-yl, 1,3-butadien-2-yl, 2-buten-1-yl, 2-buten-2-yl, 3-buten-1-yl, 3-buten-2-yl, 2-methyl-1-propen-1-yl, and 2-methyl-2-propen-1-yl.

The term "$C_5$-alkenyl" means 2-methylene-3-buten-1-yl, 2-methylenebut-1-yl, 2-methyl-1-buten-1-yl, 2-methyl-1,3-butadien-1-yl, 2-methyl-2-buten-1-yl, 2-methyl-3-buten-1-yl, 2-methyl-3-buten-2-yl, 3-methyl-1-buten-1-yl, 3-methyl-1-buten-2-yl, 3-methyl-1,3-butadien-1-yl, 3-methyl-1,3-butadien-2-yl, 3-methyl-2-buten-1-yl, 3-methyl-2-buten-2-yl, 3-methyl-3-buten-1-yl, 3-methyl-3-buten-2-yl, 1-penten-1-yl, 1-penten-2-yl, 1-penten-3-yl, 1,3-pentadien-1-yl, 1,3-pentadien-2-yl, 1,3-pentadien-3-yl, 1,4-pentadien-1-yl, 1,4-pentadien-2-yl, 1,4-pentadien-3-yl, 2-penten-1-yl, 2-penten-2-yl, 2-penten-3-yl, 2,4-pentadien-1-yl, 2,4-pentadien-2-yl, 3-penten-1-yl, 3-penten-2-yl, 4-penten-1-yl, and 4-penten-2-yl.

The term "$C_6$-alkenyl" means 2,2-dimethyl-3-buten-1-yl, 2,3-dimethyl-1-buten-1-yl, 2,3-dimethyl-1,3-butadien-1-yl, 2,3-dimethyl-2-buten-1-yl, 2,3-dimethyl-3-buten-1-yl, 2,3-dimethyl-3-buten-2-yl, 3,3-dimethyl-1-buten-1-yl, 3,3-dimethyl-1-buten-2-yl, 2-ethenyl-1,3-butadien-1-yl, 2-ethenyl-2-buten-1-yl, 2-ethyl-1-buten-1-yl, 2-ethyl-1,3-butadien-1-yl, 2-ethyl-2-buten-1-yl, 2-ethyl-3-buten-1-yl, 1-hexen-1-yl, 1-hexen-2-yl, 1-hexen-3-yl, 1,3-hexadien-1-yl, 1,3-hexadien-2-yl, 1,3-hexadien-3-yl, 1,3,5-hexatrien-1-yl, 1,3,5-hexatrien-2-yl, 1,3,5-hexatrien-3-yl, 1,4-hexadien-1-yl, 1,4-hexadien-2-yl, 1,4-hexadien-3-yl, 1,5-hexadien-1-yl, 1,5-hexadien-2-yl, 1,5-hexadien-3-yl, 2-hexen-1-yl, 2-hexen-2-yl, 2-hexen-3-yl, 2,4-hexadien-1-yl, 2,4-hexadien-2-yl, 2,4-hexadien-3-yl, 2,5-hexadien-1-yl, 2,5-hexadien-2-yl, 2,5-hexadien-3-yl, 3-hexen-1-yl, 3-hexen-2-yl, 3-hexen-3-yl, 3,5-hexadien-1-yl, 3,5-hexadien-2-yl, 3,5-hexadien-3-yl, 4-hexen-1-yl, 4-hexen-2-yl, 4-hexen-3-yl, 5-hexen-1-yl, 5-hexen-2-yl, 5-hexen-3-yl, 2-methylene-3-methyl-3-buten-1-yl, 2-methylene-3-methylbut-1-yl, 2-methylene-3-penten-1-yl, 2-methylene-4-penten-1-yl, 2-methylenepent-1-yl, 2-methylenepent-3-yl, 3-methylene-1-penten-1-yl, 3-methylene-1-penten-2-yl, 3-methylenepent-1-yl, 3-methylene-1,4-pentadien-1-yl, 3-methylene-1,4-pentadien-2-yl, 3-methylenepent-2-yl, 2-methyl-1-penten-1-yl, 2-methyl-1-penten-3-yl, 2-methyl-1,3-pentadien-1-yl, 2-methyl-1,3-pentadien-3-yl, 2-methyl-1,4-pentadien-1-yl, 2-methyl-1,4-pentadien-3-yl, 2-methyl-2-penten-1-yl, 2-methyl-2-penten-3-yl, 2-methyl-2,4-pentadien-1-yl, 2-methyl-2,4-pentadien-3-yl, 2-methyl-3-penten-1-yl, 2-methyl-3-penten-2-yl, 2-methyl-3-penten-3-yl, 2-methyl-4-penten-1-yl, 2-methyl-4-penten-2-yl, 2-methyl-4-penten-3-yl, 3-methyl-1-penten-1-yl, 3-methyl-1-penten-2-yl, 3-methyl-1,3-pentadien-1-yl, 3-methyl-1,3-pentadien-2-yl, 3-methyl-1,4-pentadien-1-yl, 3-methyl-1,4-pentadien-2-yl, 3-methyl-2-penten-1-yl, 3-methyl-2-penten-2-yl, 3-methyl-2,4-pentadien-1-yl, 3-methyl-3-penten-1-yl, 3-methyl-3-penten-2-yl, 3-methyl-4-penten-1-yl, 3-methyl-4-penten-2-yl, 3-methyl-4-penten-3-yl, 4-methyl-1-penten-1-yl, 4-methyl-1-penten-2-yl, 4-methyl-1-penten-3-yl, 4-methyl-1,3-pentadien-1-yl, 4-methyl-1,3-pentadien-2-yl, 4-methyl-1,3-pentadien-3-yl, 4-methyl-1,4-pentadien-1-yl, 4-methyl-1,4-pentadien-2-yl, 4-methyl-1,4-pentadien-3-yl, 4-methylene-2-penten-3-yl, 4-methyl-2-penten-1-yl, 4-methyl-2-penten-2-yl, 4-methyl-2-penten-3-yl, 4-methyl-2,4-pentadien-1-yl, 4-methyl-2,4-pentadien-2-yl, 4-methyl-3-penten-1-yl, 4-methyl-3-penten-2-yl, 4-methyl-3-penten-3-yl, 4-methyl-4-penten-1-yl, and 4-methyl-4-penten-2-yl.

The term "$C_1$-alkyl" means methyl.

The term "$C_2$-alkyl" means ethyl.

The term "$C_3$-alkyl" means prop-1-yl and prop-2-yl (isopropyl).

The term "$C_4$-alkyl" means but-1-yl, but-2-yl, 2-methylprop-1-yl, and 2-methylprop-2-yl (tert-butyl).

The term "$C_5$-alkyl" means 2,2-dimethylprop-1-yl (neopentyl), 2-methylbut-1-yl, 2-methylbut-2-yl, 3-methylbut-1-yl, 3-methylbut-2-yl, pent-1-yl, pent-2-yl, and pent-3-yl.

The term "$C_6$-alkyl" means 2,2-dimethylbut-1-yl, 2,3-dimethylbut-1-yl, 2,3-dimethylbut-2-yl, 3,3-dimethylbut-1-yl, 3,3-dimethylbut-2-yl, 2-ethylbut-1-yl, hex-1-yl, hex-2-yl, hex-3-yl, 2-methylpent-1-yl, 2-methylpent-2-yl, 2-methylpent-3-yl, 3-methylpent-1-yl, 3-methylpent-2-yl, 3-methylpent-3-yl, 4-methylpent-1-yl, and 4-methylpent-2-yl.

The term "$C_2$-alkynyl" means ethynyl (acetylenyl).

The term "$C_3$-alkynyl" means 1-propyn-1-yl and 2-propyn-1-yl (propargyl).

The term "$C_4$-alkynyl" means 1-butyn-1-yl, 1,3-butadiyn-1-yl, 2-butyn-1-yl, 3-butyn-1-yl, and 3-butyn-2-yl.

The term "$C_5$-alkynyl" means 2-methyl-3-butyn-1-yl, 2-methyl-3-butyn-2-yl, 3-methyl-1-butyn-1-yl, 1,3-pentadiyn-1-yl, 1,4-pentadiyn-1-yl, 1,4-pentadiyn-3-yl, 2,4-pentadiyn-1-yl, 1-pentyn-1-yl, 1-pentyn-3-yl, 2-pentyn-1-yl, 3-pentyn-1-yl, 3-pentyn-2-yl, 4-pentyn-1-yl, and 4-pentyn-2-yl.

The term "$C_6$-alkynyl" means 2,2-dimethyl-3-butyn-1-yl, 3,3-dimethyl-1-butyn-1-yl, 2-ethyl-3-butyn-1-yl, 2-ethynyl-3-butyn-1-yl, 1-hexyn-1-yl, 1-hexyn-3-yl, 1,3-hexadiyn-1-yl, 1,3,5-hexatriyn-1-yl, 1,4-hexadiyn-1-yl, 1,4-hexadiyn-3-yl, 1,5-hexadiyn-1-yl, 1,5-hexadiyn-3-yl, 2-hexyn-1-yl, 2,5-hexadiyn-1-yl, 3-hexyn-1-yl, 3-hexyn-2-yl, 3,5-hexadiyn-2-yl, 4-hexyn-1-yl, 4-hexyn-2-yl, 4-hexyn-3-yl, 5-hexyn-1-yl, 5-hexyn-2-yl, 5-hexyn-3-yl, 2-methyl-3-pentyn-1-yl, 2-methyl-3-pentyn-2-yl, 2-methyl-4-pentyn-1-yl, 2-methyl-4-pentyn-2-yl, 2-methyl-4-pentyn-3-yl, 3-methyl-1-pentyn-1-yl, 3-methyl-4-pentyn-1-yl, 3-methyl-4-pentyn-2-yl, 3-methyl-1,4-pentadiyn-1-yl, 3-methyl-1,4-pentadiyn-3-yl, 3-methyl-4-pentyn-1-yl, 3-methyl-4-pentyn-3-yl, 4-methyl-1-pentyn-1-yl, and 4-methyl-2-pentyn-1-yl.

Variable moieties can combine with the parent molecular moieties of the compounds of this invention to provide still even yet another embodiment of this invention, which embodiment pertains to compounds of this invention having formula (I), and salts, prodrugs, salts of prodrugs, and metabolites thereof, in which $R^1$ is —OH, —$OR^5$, —$NH_2$, —$NHR^5$, or —$N(R^5)_2$; $R^2$ is hydrogen, tert-butyl, —O(allyl), (4-methoxyphenyl)methyl, or (2,4-dimethoxyphenyl)methyl; $R^3$ and $R^4$ together are thiazole or pyrimidine, each of which is substituted with one or two independently selected $R^6$, $R^9$, $R^{10}$, $R^{11}$, —$OR^6$, —$OR^9$, —$O(CH_2)R^{10}$, —$O(CH_2)R^{11}$, —$SR^6$, —$SR^9$, —$S(CH_2)R^{10}$, —$S(CH_2)R^{11}$, —$S(O)R^6$, —$S(O)R^9$, —$S(O)(CH_2)R^{10}$, —$S(O)(CH_2)R^{11}$, —$SO_2R^6$, —$SO_2R^9$, —$SO_2(CH_2)R^{10}$, —$SO_2(CH_2)R^{11}$, —$CO(O)R^6$, —$CO(O)R^9$, —$C(O)OR^{10}$, —$C(O)OR^{11}$, —$NH_2$, —$NHR^6$, —$NHR^9$, —$NHR^{10}$, —$NHR^{11}$, —$NHC(O)R^6$, —$NHC(O)R^9$, —$NHC(O)R^{10}$, —$NHC(O)R^{11}$, —$NHC(O)OR^6$, —$NHC(O)OR^9$, —$NHC(O)OR^{10}$, —$NHC(O)OR^{11}$, —$NHSO_2R^6$, —$NHSO_2R^9$, —$NHSO_2R^{10}$, —$NHSO_2R^{11}$, —$N(R^6)_2$, —$N(R^9)_2$, —$N(R^{10})_2$, or —$N(R_{11})_2$ substituents; $R^5$ is $C_1$-alkyl, $C_2$-alkyl, $C_3$-alkyl, $C_4$-alkyl, $C_5$-alkyl, or $C_6$-alkyl; $R^6$ is $C_1$-alkyl, $C_2$-alkyl, $C_3$-alkyl, $C_4$-alkyl, $C_5$-alkyl, or $C_6$-alkyl, each of which is unsubstituted or substituted with one —F, —Cl, —Br, —I, —OH, —$OR^{6a}$, —$NH_2$, —$NHR^{6a}$, —$N(R^{6a})_2$, $R^{12}$, $R^{13}$, or $R^{14}$ substituent; $R^{6a}$ is $C_1$-alkyl, $C_2$-alkyl, $C_3$-alkyl, $C_4$-alkyl, $C_5$-alkyl, $C_6$-alkyl, or $R^{6b}$; $R^{6b}$ is $C_1$-alkyl, $C_2$-alkyl, $C_3$-alkyl, $C_4$-alkyl, $C_5$-alkyl, or $C_6$-alkyl, each of which is substituted with one or two independently selected —F, —Cl, —Br, —I, —OH, =O, —$OR^{6c}$, —$NH_2$, —$NHR^{6c}$, or —$N(R^{6c})_2$ substituents; $R^{6c}$ is $C_1$-alkyl, $C_2$-alkyl, $C_3$-alkyl, $C_4$-alkyl, $C_5$-alkyl, or $C_6$-alkyl; $R^9$ is phenyl which is unsubstituted or substituted with one or two or three or four independently selected $R^{9a}$, —F, —Cl, —Br, —I, —CN, —OH, —$OR^{9a}$, —$NH_2$, —$NHR^{9a}$, —$N(R^{9a})_2$, —$NO_2$, —$CF_3$, —$OCF_3$, —$SR^{9a}$, —$S(O)R^{9a}$, —$SO_2R^{9a}$, —$C(O)R^{9a}$, —$C(O)OH$, —$C(O)OR^{9a}$, —$C(O)NH_2$, —$C(O)NHR^{9a}$, —$C(O)N(R^{9a})_2$, $R^{15}$, or $R^{16}$ substituents; $R^{9a}$ is $C_1$-alkyl, $C_2$-alkyl, $C_3$-alkyl, $C_4$-alkyl, $C_5$-alkyl, $C_6$-alkyl, or $R^{9b}$; $R^{9b}$ is $C_1$-alkyl, $C_2$-alkyl, $C_3$-alkyl, $C_4$-alkyl, $C_5$-alkyl, or $C_6$-alkyl, each of which is substituted with one or two independently selected —F, —Cl, —Br, —I, —OH, =O, —$OR^{9c}$, —$NH_2$, —$NHR^{9c}$, or —$N(R^{9c})_2$ substituents; $R^{9c}$ is $C_1$-alkyl, $C_2$-alkyl, $C_3$-alkyl, $C_4$-alkyl, $C_5$-alkyl, or $C_6$-alkyl; $R^{10}$ is furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl, each of which is unsubstituted or substituted with one or two or three independently selected $R^{10a}$, —F, —Cl, —Br, —I, —CN, —OH, —$OR^{10a}$, —$NH_2$, —$NHR^{10a}$, —$N(R^{10a})_2$, —$NO_2$, —$CF_3$, —$OCF_3$, —$SR^{10a}$, —$S(O)R^{10a}$, —$SO_2R_{10}$, —$C(O)R^{10a}$, —$C(O)OH$, —$C(O)OR^{10a}$, —$C(O)NH_2$, —$C(O)NHR^{10a}$, —$C(O)N(R^{10a})_2$, $R^{15}$, or $R^{16}$ substituents; $R^{10a}$ is $C_1$-alkyl, $C_2$-alkyl, $C_3$-alkyl, $C_4$-alkyl, $C_5$-alkyl, $C_6$-alkyl, or $R^{10b}$; $R^{10b}$ is $C_1$-alkyl, $C_2$-alkyl, $C_3$-alkyl, $C_4$-alkyl, $C_5$-alkyl, or $C_6$-alkyl, each of which is substituted with one or two independently selected —F, —Cl, —Br, —I, —OH, =O, —$OR^{10c}$, —$NH_2$, —$NHR^{10c}$, or —$N(R^{10c})_2$, substituents; $R^{10c}$ is $C_1$-alkyl, $C_2$-alkyl, $C_3$-alkyl, $C_4$-alkyl, $C_5$-alkyl, or $C_6$-alkyl; $R^{11}$ is aziridinyl, azetidinyl, pyrrolidinyl, piperidinyl, or piperazinyl, each of which is unfused or fused with benzene, aziridine, azetidine, pyrrolidine, piperidine, or piperazine, in which each ring is unsubstituted or substituted with one or two or three independently selected $R^{11a}$, —F, —Cl, —Br, —I, —CN, —OH, =O, —$OR^{11a}$, —$NH_2$, —$NHR^{11a}$, —$N(R^{11a})_2$, —$NO_2$, —$CF_3$, —$OCF_3$, —$SR^{11a}$, —$S(O)R^{11a}$, —$SO_2R^{11a}$, —$C(O)R^{11a}$, —$C(O)OH$, —$C(O)OR^{11a}$, —$C(O)NH_2$, —$C(O)NHR^{11a}$, —$C(O)N(R^{11a})_2$, $R^{15}$, or $R^{16}$ substituents; $R^{11a}$ is $C_1$-alkyl, $C_2$-alkyl, $C_3$-alkyl, $C_4$-alkyl, $C_5$-alkyl, $C_6$-alkyl, or $R^{11b}$; $R^{11B}$ is $C_1$-alkyl, $C_2$-alkyl, $C_3$-alkyl, $C_4$-alkyl, $C_5$-alkyl, or $C_6$-alkyl, each of which is substituted with one or two independently selected —F, —Cl, —Br, —I, —OH, =O, —$OR^{11c}$, —$NH_2$, —$NHR^{11c}$, or —$N(R^{11c})_2$ substituents; $R^{11c}$ is $C_1$-alkyl, $C_2$-alkyl, $C_3$-alkyl, $C_4$-alkyl, $C_5$-alkyl, or $C_6$-alkyl; $R^{12}$ is phenyl which is unsubstituted or substituted with one or two or three or four independently selected $R^{12a}$, —F, —Cl, —Br, —I, —CN, —OH, —$OR^{12a}$, —$NH_2$, —$NHR^{12a}$, —$N(R^{12a})_2$, —$NO_2$, —$CF_3$, —$OCF_3$, —$SR^{12a}$, —$S(O)R^{12a}$, —$SO_2R^{12a}$, —$C(O)R^{12a}$, —C(O)OH, —C(O)$OR^{12a}$, —$C(O)NH_2$, —$C(O)NHR^{12a}$, —$C(O)N(R^{12a})_2$, $R^{15}$, or $R^{16}$ substituents; $R^{12a}$ is $C_1$-alkyl, $C_2$-alkyl, $C_3$-alkyl, $C_4$-alkyl, $C_5$-alkyl, or $C_6$-alkyl, or $R^{12b}$; $R^{12b}$ is $C_1$-alkyl, $C_2$-alkyl, $C_3$-alkyl, $C_4$-alkyl, $C_5$-alkyl, or $C_6$-alkyl, each of which is substituted with one or two independently selected —F, —Cl, —Br, —I, —OH, =O, —$OR^{12c}$, —$NH_2$, —$NHR^{12c}$, or —$N(R^{12c})_2$ substituents; $R^{12c}$ is $C_1$-alkyl, $C_2$-alkyl, $C_3$-alkyl, $C_4$-alkyl, $C_5$-alkyl, or $C_6$-alkyl; $R^{13}$ is furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl, each of which is unsubstituted or substituted with one or two or three independently selected $R^{13a}$, —F, —Cl, —Br, —I, —CN, —OH, —$OR^{13a}$, —$NH_2$, —$NHR^{13a}$, —$N(R^{13a})_2$, —$NO_2$, —$CF_3$, —$OCF_3$, —$SR^{13a}$, —$S(O)R^{13a}$, —$SO_2R^{13a}$, —$C(O)R^{13a}$, —C(O)OH, —C(O)$OR^{13a}$, —$C(O)NH_2$, —$C(O)NHR^{13a}$, —$C(O)N(R^{13a})_2$, $R^{15}$ or $R^{16}$ substituents; $R^{13a}$ is $C_1$-alkyl, $C_2$-alkyl, $C_3$-alkyl, $C_4$-alkyl, $C_5$-alkyl, $C_6$-alkyl, or $R^{13b}$; $R^{13b}$ is $C_1$-alkyl, $C_2$-alkyl, $C_3$-alkyl, $C_4$-alkyl, $C_5$-alkyl, or $C_6$-alkyl, each of which is substituted with one or two independently selected —F, —Cl, —Br, —I, —OH, =O, —$OR^{13c}$, —$NH_2$, —$NHR^{13c}$, or —$N(R^{13c})_2$ substituents; $R^{13c}$ is $C_1$-alkyl, $C_2$-alkyl, $C_3$-alkyl, $C_4$-alkyl, $C_5$-alkyl, or $C_6$-alkyl; $R^{14}$ is aziridinyl, azetidinyl, pyrrolidinyl, piperidinyl, or piperazinyl, each of which is unsubstituted or substituted with one or two or three independently selected $R^{14a}$, —F, —Cl, —Br, —I, —CN, —OH, =O, —$OR^{14a}$, —$NH_2$, —$NHR^{14a}$, —$N(R^{14a})_2$, —$NO_2$, —$CF_3$, —$OCF_3$, —$SR^{14a}$, —$S(O)R^{14a}$, —$SO_2R^{14a}$, —$C(O)R^{14a}$, —C(O)OH, —C(O)$OR^{14a}$, —$C(O)NH_2$, —$C(O)NHR^{14a}$, —$C(O)N(R^{14a})_2$, $R^{16}$, or $R^{17}$ substituents; $R^{14a}$ is $C_1$-alkyl, $C_2$-alkyl, $C_3$-alkyl, $C_4$-alkyl, $C_5$-alkyl, $C_6$-alkyl, or $R^{14b}$; $R^{14b}$ is $C_1$-alkyl, $C_2$-alkyl, $C_3$-alkyl, $C_4$-alkyl, $C_5$-alkyl, or $C_6$-alkyl, each of which is substituted with one or two independently selected —F, —Cl, —Br, —I, —OH, =O, —$OR^{14c}$, —$NH_2$, —$NHR^{14c}$, or —$N(R^{14a})_2$, substituents; $R^{14c}$ is $C_1$-alkyl, $C_2$-alkyl, $C_3$-alkyl, $C_4$-alkyl, $C_5$-alkyl, or $C_6$-alkyl; $R^{15}$ is phenyl which is unsubstituted or substituted with one or two or three or four independently selected $R^{15a}$, —F, —Cl, —Br, —I, —CN, —OH, —$OR^{15a}$, —$NH_2$, —$NHR^{15a}$, —$N(R^{15a})_2$, —$NO_2$, —$CF_3$, —$OCF_3$, —$SR^{15a}$, —$S(O)R^{15a}$, —$SO_2R^{15a}$, —$C(O)R^{15a}$, —C(O)OH, —C(O)$OR^{15a}$, —$C(O)H_2$, —$C(O)NHR^{15a}$, or —$C(O)N(R^{15a})_2$ substituents; $R^{15a}$ is $C_1$-alkyl, $C_2$-alkyl, $C_3$-alkyl, $C_4$-alkyl, $C_5$-alkyl, $C_6$-alkyl, or $R^{15b}$; $R^{15b}$ is $C_1$-alkyl, $C_2$-alkyl, $C_3$-alkyl, $C_4$-alkyl, $C_5$-alkyl, or $C_6$-alkyl, each of which is substituted with one or two independently selected —F, —Cl, —Br, —I, —OH, =O, —$OR^{15c}$, —$NH_2$, —$NHR^{15c}$, or —$N(R^{15c})_2$ substituents; $R^{15c}$ is $C_1$-alkyl, $C_2$-alkyl, $C_3$-alkyl, $C_4$-alkyl, $C_5$-alkyl, or $C_6$-alkyl; $R^{16}$ is furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl, each of which is unsubstituted or substituted with one or two or three independently selected $R^{16a}$, —F, —Cl, —Br, —I, —CN, —OH, —$OR^{16a}$, —$NH_2$, —$NHR^{16a}$, —$N(R^{16a})_2$, —$CF_3$, —$OCF_3$, —$SR^{16a}$, —$S(O)R^{16a}$, —$SO_2R^{16a}$, —$C(O)R^{16a}$, —C(O)OH, —C(O)$OR^{16a}$, —$C(O)NH_2$, —$C(O)NHR^{16a}$, or —$C(O)N(R^{16a})_2$ substituents; $R^{16a}$ is $C_1$-alkyl, $C_2$-alkyl, $C_3$-alkyl, $C_4$-alkyl, $C_5$-alkyl, $C_6$-alkyl, or $R^{16b}$; $R^{16b}$ is $C_1$-alkyl, $C_2$-alkyl, $C_3$-alkyl, $C_4$-alkyl, $C_5$-alkyl, or $C_6$-alkyl, each of which is substituted with one or two independently selected —F, —Cl, —Br, —I, —OH, —$OR^{16c}$, =O, —$NH_2$, —$NHR^{16c}$, or —$N(R^{16c})_2$ substituents; and $R^{16c}$ is $C_1$-alkyl, $C_2$-alkyl, $C_3$-alkyl, $C_4$-alkyl, $C_5$-alkyl, or $C_6$-alkyl.

Variable moieties can also combine with the parent molecular moieties of the compounds of this invention to provide still even yet another embodiment of this invention, which embodiment pertains to compounds of this invention having formula (I), and salts, prodrugs, salts of prodrugs, and metabolites thereof, in which $R^1$ is —OH, —$OR^5$, —$NH_2$, —$NHR^5$, or —$N(R^5)_2$; $R^2$ is hydrogen, tert-butyl, —O(allyl), (4-methoxyphenyl)methyl, or (2,4-dimethoxyphenyl)methyl; $R^3$ and $R^4$ together are thiazole or pyrimidine, each of which is substituted with one or two independently selected $R^6$, $R^9$, $R^{11}$, —$OR^6$, —$OR^9$, —$O(CH_2)R^{11}$, —$SR^6$, —$SR^9$, —$S(CH_2)R^{11}$, —$S(O)R^6$, —$S(O)R^9$, —$S(O)(CH_2)R^{11}$, —$SO_2R^6$, —$SO_2R^9$, —$SO_2(CH_2)R^{11}$, —$CO(O)R^6$, —$CO(O)R^9$, —$C(O)OR^{11}$, —$NH_2$, —$NHR^6$, —$NHR^9$, —$NHR^{11}$, —$NHC(O)R^6$, —$NHC(O)R^9$, —$NHC(O)R^{11}$, —$NHC(O)OR^6$, —$NHC(O)OR^9$, —$NHC(O)OR^{11}$, —$NHSO_2R^6$, —$NHSO_2R^9$, —$NHSO_2R^{11}$, —$N(R^6)_2$, —$N(R^9)_2$, or —$N(R^{11})_2$ substituents; $R^5$ is $C_1$-alkyl, $C_2$-alkyl, $C_3$-alkyl, $C_4$-alkyl, $C_5$-alkyl, or $C_6$-alkyl; $R^6$ is $C_1$-alkyl, $C_2$-alkyl, $C_3$-alkyl, $C_4$-alkyl, $C_5$-alkyl, or $C_6$-alkyl, each of which is unsubstituted or substituted with one —F, —Cl, —Br, —I, —OH, —$OR^{6a}$, —$NH_2$, —$NHR^{6a}$, —$N(R^{6a})_2$, $R^{12}$, $R^{13}$, or $R^{14}$ substituent; $R^{6a}$ is $C_1$-alkyl, $C_2$-alkyl, $C_3$-alkyl, $C_4$-alkyl, $C_5$-alkyl, or $C_6$-alkyl; $R^9$ is phenyl which is unsubstituted or substituted with one or two or three or four independently selected $R^{9a}$, —F, —Cl, —Br, —I, —CN, —OH, —$OR^{9a}$, —$NH_2$, —$NHR^{9a}$, —$N(R^{9a})_2$, —$NO_2$, —$CF_3$, —$OCF_3$, —$SR^{9a}$, —$S(O)R^{9a}$, —$SO_2R^{9a}$, —$C(O)R^{9a}$, —C(O)OH, —C(O)$OR^{9a}$, —$C(O)NH_2$, —$C(O)NHR^{9a}$, —$C(O)N(R^{9a})_2$, $R^{15}$, or $R^{16}$ substituents; $R^{9a}$ is $C_1$-alkyl, $C_2$-alkyl, $C_3$-alkyl, $C_4$-alkyl, $C_5$-alkyl, or $C_6$-alkyl; $R^{10}$ is furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl, each of which is unsubstituted or substituted with one or two or three independently selected $R^{10a}$, —F, —Cl, —Br, —I, —CN, —OH, —$OR^{10a}$, —$NH_2$, —$NHR^{10a}$, —$N(R^{10a})_2$, —$NO_2$, —$CF_3$, —$OCF_3$, —$SR^{10a}$, —$S(O)R^{10a}$, —$SO_2R^{10}$, —$C(O)R^{10a}$, —C(O)OH, —C(O)$OR^{10a}$, —$C(O)NH_2$, —$C(O)NHR^{10a}$, —$C(O)N(R^{10a})_2$, $R^{15}$, or $R^{16}$ substituents; $R^{10a}$ is $C_1$-alkyl, $C_2$-alkyl, $C_3$-alkyl, $C_4$-alkyl, $C_5$-alkyl, or $C_6$-alkyl; $R^{11}$ is aziridinyl, azetidinyl, pyrrolidinyl, piperidinyl, or piperazinyl, each of which is unfused or fused with benzene, aziridine, azetidine, pyrrolidine, piperidine, or piperazine, in which each ring is unsubstituted or substituted with one or two or three independently selected $R^{11a}$, —F, —Cl, —Br, —I, —CN, —OH, =O, —$OR^{11a}$, —$NH_2$, —$NHR^{11a}$, —$N(R^{11a})_2$, —$NO_2$, —$CF_3$, —$OCF_3$, —$SR^{11a}$, —$S(O)R^{11a}$, —$SO_2R^{11a}$, —$C(O)R^{11a}$, —C(O)OH, —C(O)$OR^{11a}$, —$C(O)NH_2$, —$C(O)NHR^{11a}$, —$C(O)N(R^{11a})_2$, $R^{15}$, or $R^{16}$ substituents; $R^{11a}$ is $C_1$-alkyl, $C_2$-alkyl, $C_3$-alkyl, $C_4$-alkyl, $C_5$-alkyl, $C_6$-alkyl, or $R^{11b}$; $R^{11B}$ is $C_1$-alkyl, $C_2$-alkyl, $C_3$-alkyl, $C_4$-alkyl, $C_5$-alkyl, or $C_6$-alkyl, each of which is substituted with one or two independently selected —F, —Cl, —Br, —I, —OH, =O, —$OR^{11c}$, —$NH_2$, —$NHR^{11c}$, or —$N(R^{11c})_2$, substituents; $R^{11c}$ is $C_1$-alkyl, $C_2$-alkyl, $C_3$-alkyl, $C_4$-alkyl, $C_5$-alkyl, or $C_6$-alkyl; $R^{12}$ is phenyl which is unsubstituted or substituted with one or two or three or four independently selected $R^{12a}$, —F, —Cl, —Br, —I, —CN, —OH, —$OR^{12a}$, —$NH_2$, —$NHR^{12a}$, —$N(R^{12a})_2$, —$NO_2$, —$CF_3$, —$OCF_3$, —$SR^{12a}$, —$S(O)R^{12a}$, —$SO_2R^{12a}$, —$C(O)R^{12a}$, —C(O)OH, —$C(O)OR^{12a}$, —$C(O)NH_2$, —$C(O)NHR^{12a}$, —$C(O)N(R^{12a})_2$, $R^{15}$, or $R^{16}$ substituents; $R^{12a}$ is $C_1$-alkyl, $C_2$-alkyl, $C_3$-alkyl, $C_4$-alkyl, $C_5$-alkyl, or $C_6$-alkyl; $R^{13}$ is furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl, each of which is unsubstituted or substituted with one or two or three independently selected $R^{13a}$, —F, —Cl, —Br, —I, —CN, —OH, —$OR^{13a}$, —$NH_2$, —$NHR^{13a}$, —$N(R^{13a})_2$, —$NO_2$, —$CF_3$, —$OCF_3$, —$SR^{13a}$, —$S(O)R^{13a}$, $SO_2R^{13a}$, —$C(O)R^{13a}$, —C(O)OH, —$C(O)OR^{13a}$, —$C(O)NH_2$, —$C(O)NHR^{13a}$, —C(O)N $(R^{13a})_2$, $R^{15}$, or $R^{16}$ substituents; $R^{13a}$ is $C_1$-alkyl, $C_2$-alkyl, $C_3$-alkyl, $C_4$-alkyl, $C_5$-alkyl, or $C_6$-alkyl; $R^{14}$ is aziridinyl, azetidinyl, pyrrolidinyl, piperidinyl, or piperazinyl, each of which is unsubstituted or substituted with one or two or three independently selected $R^{14a}$, —F, —Cl, —Br, —I, —CN, —OH, =O, —$OR^{14a}$, —$NH_2$, —$NHR^{14a}$, —$N(R^{14a})_2$, —$NO_2$, —$CF_3$, —$OCF_3$, —$SR^{14a}$, —$S(O)R^{14a}$, —$SO_2R^{14a}$, —$C(O)R^{14a}$, —C(O)OH, —$C(O)OR^{14a}$, —$C(O)NH_2$, —$C(O)NHR^{14a}$, —$C(O)N(R^{14a})_2$, $R^{16}$, or $R^{17}$ substituents; $R^{14a}$ is $C_1$-alkyl, $C_2$-alkyl, $C_3$-alkyl, $C_4$-alkyl, $C_5$-alkyl, or $C_6$-alkyl; $R^{15}$ is phenyl which is unsubstituted or substituted with one or two or three or four independently selected $R^{15a}$, —F, —Cl, —Br, —I, —CN, —OH, —$OR^{15a}$, —$NH_2$, —$NHR^{15a}$, —$N(R^{15a})_2$, —$NO_2$, —$CF_3$, —$OCF_3$, —$SR^{15a}$, —$S(O)R^{15a}$, —$SO_2R^{15a}$, —$C(O)R^{15a}$, —C(O)OH, —$C(O)OR^{15a}$, —$C(O)NH_2$, —$C(O)NHR^{15a}$, or —$C(O)N(R^{15a})_2$ substituents; $R^{15a}$ is $C_1$-alkyl, $C_2$-alkyl, $C_3$-alkyl, $C_4$-alkyl, $C_5$-alkyl, or $C_6$-alkyl; $R^{16}$ is furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl, each of which is unsubstituted or substituted with one or two or three independently selected $R^{16a}$, —F, —Cl, —Br, —I, —CN, —OH, —$OR^{16a}$, —$NH_2$, —$NHR^{16a}$, —$N(R^{16a})_2$, —$NO_2$, —$CF_3$, —$OCF_3$, —$SR^{16a}$, —$S(O)R^{16a}$, —$SO_2R^{16a}$, —$C(O)R^{16a}$, —C(O) OH, —$C(O)OR^{16a}$, —$C(O)NH_2$, —$C(O)NHR^{16a}$, or —$C(O)N(R_{16a})_2$ substituents; and $R^{16a}$ is $C_1$-alkyl, $C_2$-alkyl, $C_3$-alkyl, $C_4$-alkyl, $C_5$-alkyl, or $C_6$-alkyl.

Variable moieties can still also combine with the parent molecular moieties of the compounds of this invention to provide still even yet another embodiment of this invention, which embodiment pertains to compounds of this invention having formula (I), and salts, prodrugs, salts of prodrugs, and metabolites thereof, in which $R^1$ is —OH or —$OR^5$; $R^2$ is hydrogen or (4-methoxyphenyl)methyl; $R^3$ and $R^4$ together are thiazole or pyrimidine, each of which is substituted with one —$N(R^6)_2$, —$NHR^9$, or $R^{11}$ substituent; $R^5$ is $C_1$-alkyl, $C_2$-alkyl, $C_3$-alkyl, $C_4$-alkyl, $C_5$-alkyl, or $C_6$-alkyl; $R^6$ is $C_1$-alkyl, $C_2$-alkyl, $C_3$-alkyl, $C_4$-alkyl, $C_5$-alkyl, or $C_6$-alkyl, each of which is unsubstituted or substituted with one $R^{12}$ substituent; $R^9$ is phenyl which is substituted with two independently selected $R^{9a}$, —F, —Cl, —Br, —I, —$OR^{9a}$, or —$SR^{9a}$ substituents; $R^{9a}$ is $C_1$-alkyl, $C_2$-alkyl, $C_3$-alkyl, $C_4$-alkyl, $C_5$-alkyl, or $C_6$-alkyl; $R^{11}$ is azetidinyl, pyrrolidinyl, piperidinyl, or piperazinyl, each of which is unfused or fused with pyrrolidine, in which each ring is unsubstituted or substituted with one $R^{11a}$, —$NH_2$, or $R^{15}$ substituent; $R^{11a}$ is $C_1$-alkyl, $C_2$-alkyl, $C_3$-alkyl, $C_4$-alkyl, $C_5$-alkyl, $C_6$-alkyl, or $R^{11b}$; $R^{11B}$ is $C_1$-alkyl, $C_2$-alkyl, $C_3$-alkyl, $C_4$-alkyl, $C_5$-alkyl, or $C_6$-alkyl, each of which is substituted with one —$NH_2$ substituent; $R^{12}$ is phenyl which is substituted with two —$OR^{12a}$ substituents; $R^{12a}$ is $C_1$-alkyl, $C_2$-alkyl, $C_3$-alkyl, $C_4$-alkyl, $C_5$-alkyl, or $C_6$-alkyl; $R^{15}$ is phenyl which is substituted with one —F, —Cl, —Br, or —I substituent.

Variable moieties can still even also combine with the parent molecular moieties of the compounds of this invention to provide still even yet another embodiment of this invention, which embodiment pertains to compounds of this invention having formula (I), and salts, prodrugs, salts of prodrugs, and metabolites thereof, in which $R^1$ is —OH, or —$OR^5$; $R^2$ is hydrogen or (4-methoxyphenyl)methyl; $R^3$ and $R^4$ together are thiazole or pyrimidine, each of which is substituted with one or two independently selected —$NH_2$, —$N(R^6)_2$, —$NHR^9$, or $R^{11}$ substituents; $R^5$ is $C_2$-alkyl; $R^6$ is $C_1$-alkyl or $C_2$-alkyl, both of which are unsubstituted or substituted with one $R^{12}$ substituent; $R^9$ is phenyl which is substituted with two independently selected $R^{9a}$, —F, —Cl, —Br, —I, —$OR^{9a}$, or —$SR^{9a}$ substituents; $R^{9a}$ is $C_1$-alkyl, $C_2$-alkyl, or $C_3$-alkyl; $R^{11}$ is azetidinyl, pyrrolidinyl, piperidinyl, or piperazinyl, each of which is unfused or fused with pyrrolidine, in which each ring is unsubstituted or substituted with one $R^{11a}$, —$NH_2$, or $R^{15}$ substituent; $R^{11a}$ is $C_1$-alkyl substituted with —$NH_2$; $R^{12}$ is phenyl substituted with two —$OR^{12a}$ substituents; $R^{12a}$ is $C_1$-alkyl; $R^{15}$ is phenyl substituted with one —F, —Cl, —Br, or —I substituent.

$R^1$ is specifically embodied by —OH and —O(ethyl); $R^2$ is specifically embodied by hydrogen; and $R^3$ and $R^4$ together are specifically embodied by 2-(aminomethyl)piperidin-1-yl[1,3]thiazolo, 2-(aminomethyl)-pyrrolidin-1-yl[1,3]thiazolo, 3-aminopiperidin-1-yl[1,3]thiazolo, 2-(3-aminopyrrolidin-1-yl)-4-amino-[2,3-d]pyrimidino, 2-(3-aminopyrrolidin-1-yl)[2,3-d]pyrimidino, 2-(azetidin-1-yl)-4-amino-[2,3-d]pyrimidino, 2-(azetidin-1-yl)[2,3-d]pyrimidino, 2-(1-benzylhexahydropyrrolo[3,4-b]pyrrol-5(1H)-yl)-4-amino-[2,3-d]pyrimidino, 4-bromo-3-methylanilino[1,3]thiazolo, 4-(2-chlorophenyl)piperazin-1-yl[1,3]thiazolo,((3,4-dimethoxyphenyl)ethyl)(methyl) amino[1, 3]thiazolo, 2-fluoro-4-methylanilino[1,3]thiazolo, 3-fluoro-4-methylanilino[1,3]thiazolo, 4-(2-fluorophenyl) piperazin-1-yl[1,3]thiazolo, 1H-indazol-4-ylamino[1,3]thiazolo, methyl(2-phenylethyl)amino[1,3]thiazolo, 4-(methylsulfanyl)-anilino[1,3]thiazolo, 4-propoxyanilino-[1,3] thiazolo, 2-(pyrrolidin-1-yl)-4-amino-[2,3-d]pyrimidino, 2-(pyrrolidin-1-yl)[2,3-d]pyrimidino, and pyrrolidin-1-yl[1,3]thiazolo.

These specific embodiments can combine with the parent molecular moieties of the compounds of this invention to provide still even yet another embodiment of this invention, which embodiment pertains to compounds of this invention having formula (I), and salts, prodrugs, salts of prodrugs, and metabolites thereof, in which $R^1$ is —OH or —O(ethyl); $R^2$ is hydrogen; and $R^3$ and $R^4$ together are 2-(3-aminopyrrolidin-1-yl)-4-amino[2,3-d]pyrimidino, 2-(3-aminopyrrolidin-1-yl)[2,3-d]pyrimidino, 2-(azetidin-1-yl)-4-amino[2,3-d]pyrimidine, or 2-(azetidin-1-yl)[2,3-d]pyrimidino.

These specific embodiments can also combine with the parent molecular moieties of the compounds of this invention to provide still even yet another embodiment of this invention, which embodiment pertains to compounds of this invention having formula (I), and salts, prodrugs, salts of prodrugs, and metabolites thereof, in which $R^1$ is —OH or —O(ethyl); $R^2$ is hydrogen; and $R^3$ and $R^4$ together are 2-(1-benzylhexahydro-pyrrolo[3,4-b]pyrrol-5(1H)-yl)-4-amino[2,3-d]pyrimidino, 2-(pyrrolidin-1-yl)-4-amino[2,3-d]pyrimidino, or 2-(pyrrolidin-1-yl)[2,3-d]pyrimidino.

These specific embodiments can still also combine with the parent molecular moieties of the compounds of this invention to provide still even yet another embodiment of this invention, which embodiment pertains to compounds of this invention having formula (I), and salts, prodrugs, salts of prodrugs, and metabolites thereof, in which $R^1$ is —OH or —O(ethyl); $R^2$ is hydrogen; and $R^3$ and $R^4$ together are 2-(aminomethyl)-piperidin-1-yl[1,3]thiazolo, 2-(amino-methyl)pyrrolidin-1-yl[1,3]thiazolo, 3-aminopiperidin-1-yl[1,3]thiazolo, 4-bromo-3-methylanilino[1,3]thiazolo, 4-(2-chlorophenyl)-piperazin-1-yl[1,3]thiazolo, ((3,4-dimethoxyphenyl)ethyl)(methyl)amino[1,3]thiazolo, 2-fluoro-4-methylanilino[1,3]thiazolo, or 3-fluoro-4-methylanilino[1,3]thiazolo.

These specific embodiments can still even also combine with the parent molecular moieties of the compounds of this invention to provide still even yet another embodiment of this invention, which embodiment pertains to compounds of this invention having formula (I), and salts, prodrugs, salts of prodrugs, and metabolites thereof, in which $R^1$ is —OH or —O(ethyl); $R^2$ is hydrogen; and $R^3$ and $R^4$ together are together are 4-(2-fluorophenyl)piperazin-1-yl[1,3]thiazolo, 1H-indazol-4-ylamino[1,3]thiazolo, methyl(2-phenylethyl)amino-[1,3]thiazolo, 4-(methylsulfanyl)anilino[1,3]thiazolo, 4-propoxyanilino[1,3]thiazolo, or pyrrolidin-1-yl-[1,3]thiazolo.

These specific embodiments can still even also combine with the parent molecular moieties of the compounds of this invention to provide still even yet another embodiment of this invention, which embodiment pertains to compounds of this invention having formula (I), and salts, prodrugs, salts of prodrugs, and metabolites thereof, which are 2-(3-(aminomethyl)pyrrolidin-1-yl)-4-(4-methoxybenzyl)-7-oxo-4,7-dihydro[1,3]thiazolo[4,5-b]pyridine-6-carboxylic acid, 2-(3-aminopiperidin-1-yl)-7-oxo-4,7-dihydro[1,3]thiazolo[4,5-b]pyridine-6-carboxylic acid, 2-(3-(aminomethyl)piperidin-1-yl)-7-oxo-4,7-dihydro[1,3]thiazolo[4,5-b]pyridine-6-carboxylic acid, 2-(methyl(2-phenylethyl)amino)-7-oxo-4,7-dihydro[1,3]thiazolo[4,5-b]pyridine-6-carboxylic acid, 2-((2-(3,4-dimethoxyphenyl)ethyl)(methyl)amino)-7-oxo-4,7-dihydro[1,3]thiazolo[4,5-b]pyridine-6-carboxylic acid, 2-(4-(2-fluorophenyl)piperazin-1-yl)-7-oxo-4,7-dihydro[1,3]thiazolo[4,5-b]pyridine-6-carboxylic acid, 2-(4-(2-chlorophenyl)piperazin-1-yl)-7-oxo-4,7-dihydro[1,3]thiazolo[4,5-b]pyridine-6-carboxylic acid, 2-(2-fluoro-4-methylanilino)-7-oxo-4,7-dihydro[1,3]thiazolo[4,5-b]pyridine-6-carboxylic acid, 2-(3-fluoro-4-methylanilino)-7-oxo-4,7-dihydro[1,3]thiazolo[4,5-b]pyridine-6-carboxylic acid, 2-(4-bromo-3-methylanilino)-7-oxo-4,7-dihydro[1,3]thiazolo[4,5-b]pyridine-6-carboxylic acid, 7-oxo-2-(4-propoxyanilino)-4,7-dihydro[1,3]thiazolo[4,5-b]pyridine-6-carboxylic acid, 2-(4-(methylsulfanyl)anilino)-7-oxo-4,7-dihydro[1,3]thiazolo[4,5-b]pyridine-6-carboxylic acid, 2-(pyrrolidin-1-yl)-5-oxo-5,8-dihydro[2,3-d]pyrimidinopyridine-6-carboxylic acid, 2-(azetidin-1-yl)-5-oxo-5,8-dihydro[2,3-d]pyrimidinopyridine-6-carboxylic acid, 2-(3-aminopyrrolidin-1-yl)-5-oxo-5,8-dihydro[2,3-d]pyrimidinopyridine-6-carboxylic acid, 4-amino-5-oxo-2-(pyrrolidin-1-yl)-5,8-dihydro[2,3-d]pyrimidinopyridine-6-carboxylic acid, 2-(azetidin-1-yl)-4-amino-5-oxo-5,8-dihydro[2,3-d]pyrimidinopyridine-6-carboxylic acid, ethyl 2-(3-aminopyrrolidin-1-yl)-4-amino-5-oxo-5,8-dihydro[2,3-d]pyrimidinopyridine-6-carboxylate 2-(3-aminopyrrolidin-1-yl)-4-amino-5-oxo-5,8-dihydro[2,3-d]pyrimidinopyridine-6-carboxylic acid, and 2-(1-benzylhexahydropyrrolo[3,4-b]pyrrol-5(1H)-yl)-4-amino-5-oxo-5,8-dihydropyrido[2,3-d]pyrimidine-6-carboxylic acid.

The compounds of this invention can have one or more than one asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13–10. Compounds of this invention having asymmetrically substituted carbon atoms enriched with one configuration over the other can be assigned the configuration which is present in the higher amount, preferably about 85% to about 95% enrichment, more preferably about 95% to about 99% enrichment, and still more preferably greater than about 99% enrichment. Accordingly, compounds of this invention can exist as enantiomers, mixtures of enantiomers, diastereomers having relative stereochemistry, diastereomers having absolute stereochemistry, diastereomers having at least one asymmetrically substituted carbon atom which is enriched in one configuration and at least one asymmetrically substituted carbon atom which is not enriched, and mixtures comprising the foregoing.

The compounds of this invention can also contain carbon-carbon double bonds or carbon-nitrogen double bonds in the Z or E configuration, in which the term "Z" means the two larger substituents are on the same side of the carbon-carbon or carbon-nitrogen double bond, and the term "E" means the two larger substituents are on opposite sides of the carbon-carbon or carbon-nitrogen double bond. The compounds of this invention can also exist as a mixture containing carbon-carbon double bonds or carbon-nitrogen double bonds in both Z and E configurations.

Prodrugs of the compounds of this invention having formula (I) are derivatives of the same which can hydrolyze, oxidize, reduce, or otherwise react under in vivo or in vitro biological conditions. Compounds of this invention having formula (I) having an —OH, —NH—, —SH, or —CO$_2$H moiety can have attached therethrough a prodrug-forming moiety which is removed by metabolic processes to release the compounds of this invention having formula (I) having the freed —OH, —NH—, —SH, or —CO$_2$H moiety in vivo. Prodrugs are useful for adjusting such pharmacokinetic properties of the compounds of this invention having formula (I), or the salts thereof, as solubility, hydrophobicity, absorption in the gastrointestinal tract, bioavailability, tissue penetration, and rate of clearance. Accordingly, still even yet another embodiment of this invention pertains to compounds of this invention having formula (I), or salts thereof, which exist as prodrugs or to which are attached prodrug-forming moieties.

Compounds of this invention having formula (I), and prodrugs thereof, can exist as acid addition salts, basic addition salts, or zwitterions. Salts of the compounds of this invention having formula (I), and prodrugs thereof, can be prepared during their isolation or following their purification. Acid addition salts of the compounds of this invention having formula (I), and prodrugs thereof, are those derived from reacting the same and an acid. For example, the acetate, adipate, alginate, bicarbonate, citrate, aspartate, benzoate, benzenesulfonate, bisulfate, butyrate, camphorate, camphorsufonate, citrate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetate, trifluoroacetate, para-toluenesulfonate, and undecanoate salts of the compounds of this invention having formula (I), and prodrugs thereof, are meant to be included in this invention. Basic addition salts of the compounds of this invention having formula (I), and prodrugs thereof, can be prepared by reacting the same and a base such as the hydroxide, carbonate, bicarbonate, phosphate, hydrogen phosphate, or dihydrogen phosphate of cations such as calcium, iron, lithium, potassium, sodium, or magnesium.

Compounds of this invention having formula (I), and salts, prodrugs, and salts of prodrugs thereof, can be administered with or without an excipient. Excipients include encapsulating materials or formulation additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, and mixtures thereof. Excipients for orally administered compounds of this invention having formula (I) and salts, prodrugs, and salts of prodrugs thereof, in solid dosage forms include agar, alginic acid, aluminum hydroxide, benzyl alcohol, benzyl benzoate, 1,3-butylene glycol, castor oil, cellulose, cellulose acetate, cocoa butter, corn starch, corn oil, cottonseed oil, ethanol, ethyl acetate, ethyl carbonate, ethyl cellulose, ethyl laureate, ethyl oleate, gelatin, germ oil, glucose, glycerol, groundnut oil, isopropanol, isotonic saline, lactose, magnesium hydroxide, magnesium stearate, malt, olive oil, peanut oil, potassium phosphate salts, potato starch, propylene glycol, Ringer's solution, talc, tragacanth, water, safflower oil, sesame oil, sodium carboxymethyl cellulose, sodium lauryl sulfate, sodium phosphate salts, soybean oil, sucrose, tetrahydrofurfuryl alcohol, and mixtures thereof. Excipients for ophthalmically and orally administered compounds of this invention having formula (I), and salts, prodrugs, and salts of prodrugs thereof, in liquid dosage forms include benzyl alcohol, benzyl benzoate, 1,3-butylene glycol, castor oil, corn oil, cottonseed oil, ethanol, ethyl acetate, ethyl carbonate, fatty acid esters of sorbitan, germ oil, groundnut oil, glycerol, isopropanol, olive oil, polyethylene glycols, propylene glycol, sesame oil, tetrahydrofurfuryl alcohol, water, and mixtures thereof. Excipients for osmotically administered compounds of this invention having formula (I), and salts, prodrugs, and salts of prodrugs thereof, include chlorofluoro-hydrocarbons, ethanol, isopropanol, water, and mixtures thereof. Excipients for parenterally administered compounds of this invention having formula (I), and salts, prodrugs, and salts of prodrugs thereof, include 1,3-butanediol, castor oil, corn oil, cottonseed oil, germ oil, groundnut oil, liposomes, oleic acid, olive oil, peanut oil, Ringer's solution, safflower oil, sesame oil, soybean oil, U.S.P. or isotonic sodium chloride solution, water, and mixtures thereof. Excipients for rectally and vaginally administered compounds of this invention having formula (I), and salts, prodrugs, and salts of prodrugs thereof, include cocoa butter, polyethylene glycol, wax, and mixtures thereof.

Compounds of this invention having formula (I), and salts, prodrugs, and salts of prodrugs thereof, can be administered orally, ophthalmically, osmotically, parenterally (subcutaneously, intramuscularly, intrasternally, intravenously), rectally, topically, transdermally, or vaginally. Orally administered compounds of this invention having formula (I), and salts, prodrugs, and salts of prodrugs thereof, in solid dosage forms can be administered as capsules, dragees, granules, pills, powders, and tablets. Ophthalmically and orally administered compounds of this invention having formula (I), and salts, prodrugs, or salts of prodrugs thereof, in liquid dosage forms can be administered as elixirs, emulsions, microemulsions, solutions, suspensions, and syrups. Osmotically and topically administered compounds of this invention having formula (I), and salts, prodrugs, or salts of prodrugs thereof, can be administered as creams, gels, inhalants, lotions, ointments, pastes, powders, solutions, and sprays. Parenterally administered compounds of this invention having formula (I), and salts, prodrugs, and salts of prodrugs thereof, can be administered as aqueous or oleaginous solutions or aqueous or oleaginous suspensions which comprise crystalline, amorphous, or otherwise insoluble forms of the compounds of this invention having formula (I). Rectally and vaginally administered compounds of this invention having formula (I), and salts, prodrugs, and salts of prodrugs thereof, can be administered as creams, gels, lotions, ointments, and pastes.

The therapeutically acceptable amount of a compound of this invention having formula (I), or a salt, prodrug, or salt of a prodrug thereof, depends on variables such as the recepient of treatment, the disorder being treated and the severity thereof, the composition containing the compound, the time of administration, the route of administration, the duration of treatment, the potency of the compound, the rate of clearance of the compound, and whether or not another drug is co-administered. The daily amount of a compound of this invention having formula (I), or a salt, prodrug, or salt of a prodrug thereof, administered to a patient in a single dose or in divided doses, is from about 0.1 to about 200 mg/kg body weight, preferably from about 0.25 to about 100 mg/kg body weight. Single dose compositions contain these amounts of a compound of this invention having formula (I), or a salt, prodrug, or salt of a prodrug thereof, or combinations of submultiples thereof.

To determine the antibacterial activity of the compounds of this invention having formula (I), twelve petri dishes, each containing successive aqueous dilutions of representative compounds of this invention having formula (I) in sterilized Brain Heart Infusion agar (Difco 0418-01-5) (10 mL), were inoculated with 1:100 dilutions of the representative microorganisms in TABLE 1 using a Steers replicator block (or 1:10 dilutions for slow-growing *Streptococcus* strains), co-incubated at 35–37° C. for 20–24 hours with a control plate having no compound, and inspected visually to provide the minimum inhibitory concentration (MIC), in μg/mL, by which is meant the lowest concentration of the test compound of this invention having formula (I) which yielded no growth, a slight haze, or sparsely isolated colonies on the inoculums spot as compared to growth in the control plate.

TABLE 1

| Microorganism | Code |
| --- | --- |
| Quinoline Succeptable *Streptococcus pneumoniae* ATCC 6303 | AA |
| Quinolone-Resistant *Streptococcus pneumoniae* 7257 | BB |

TABLE 2

| Example | AA MIC | BB MIC |
| --- | --- | --- |
| Ciprofloxacin | 1 | 16 |
| Norfloxacin | 1 | 32 |
| Trovafloxacin | 0.06 | 4 |
| Linezolid | 2 | 0.5 |

The antibacterial activity of the representative compounds of this invention having formula (I) was superior to the control containing no compound and in the range of about 32 μg/mL to about 64 μg/mL against AA and about 8 μg/mL to about 64 μg/mL against BB. These data demonstrate the utility of the compounds of this invention having formula (I) as antibacterials.

Bacterial protein synthesis inhibitory activity of representative compounds of this invention having formula (I) and the commercially-available antibacterials in TABLE 2 was determined by translation assays using the firefly luciferase reporter system described by Murray et al., (2001), "*Staphylococcus aureus* Cell Extract Transcription—Translation Assay: Firefly Luciferase Reporter System for Evaluating Protein Translation Inhibitors," Antimicrob. Agents Chemother. 45(6): 1900–1904, but replacing the *Staphylococcus aureus* S30 extract described therein with S30 *Streptococcus pneumoniae* extract from quinolone-succeptable *Streptococcus pneumoniae* ATCC 46919, and replacing plasmid coding for the luciferase gene with mRNA (encoding produced by in vitro transcription from the plasmid pAS10rbs3) which encoded the luciferase gene with an upstream *Streptococcus pneumoniae* promoter and Shine-Dalgarno site.

The $IC_{50}$'s of the representative compounds of this invention having formula (I), defined as concentrations of the same which caused 50% inhibition of bacterial protein synthesis, were in the range of about 1.5 μM to about 76 μM.

The $IC_{50}$'s of the commercially-available quinolones tested were greater than about 100 μM compared to the $IC_{50}$ of Linezolid which is about 3 μM.

These data demonstrate that the commercially-available quinolones which were tested do not inhibit bacterial protein synthesis in *Streptococcus pneumoniae*, even at high concentrations, that the utility of the compounds of this invention having formula (I) as antibacterials is due, at least in part, to their ability to inhibit bacterial protein synthesis, and therefore bacterial growth, and that the inhibition of bacterial protein synthesis by the compounds of this invention having formula (I) would be comparable to the inhibition of bacterial protein synthesis provided by Linezolid.

Therefore, while not being limited by theory, the compounds of this invention having formula (I) would be expected to function by a mechanism more similar to Linezolid (which inhibits bacterial protein synthesis) than quinolones (which inhibit the enzyme DNA gyrase).

Because the representative compounds of this invention having formula (I) inhibit the growth of quinolone resistant bacteria at least as well as the growth of quinolone susceptible bacteria, and because they function by a mechanism which differs from quinolones, the compounds of this invention having formula (I), and the salts, prodrugs, salts of prodrugs, and metabolites thereof, would be expected to be useful not only for treating bacterial infections but also for treating bacterial infections for which quinolones would be ineffective or only partially effective.

Metabolites of the compounds of this invention having formula (I), produced by in vitro or in vivo metabolic processes, can also be useful as antibacterials. Once identified, these metabolites can also be synthesized and evaluated for utility as antibacterials.

Compounds of this invention having formula (I), and salts, prodrugs, salts of prodrugs, and metabolites thereof, can be prepared by chemical processes, examples of which chemical processes and intermediates used in the processes are shown in the following schemes. It is meant to be understood that the order of the steps in the processes can be varied, that different intermediates, reagents, solvents, and reaction conditions can be substituted for those specifically mentioned, and that vulnerable moieties can be protected and deprotected, as needed, during the processes.

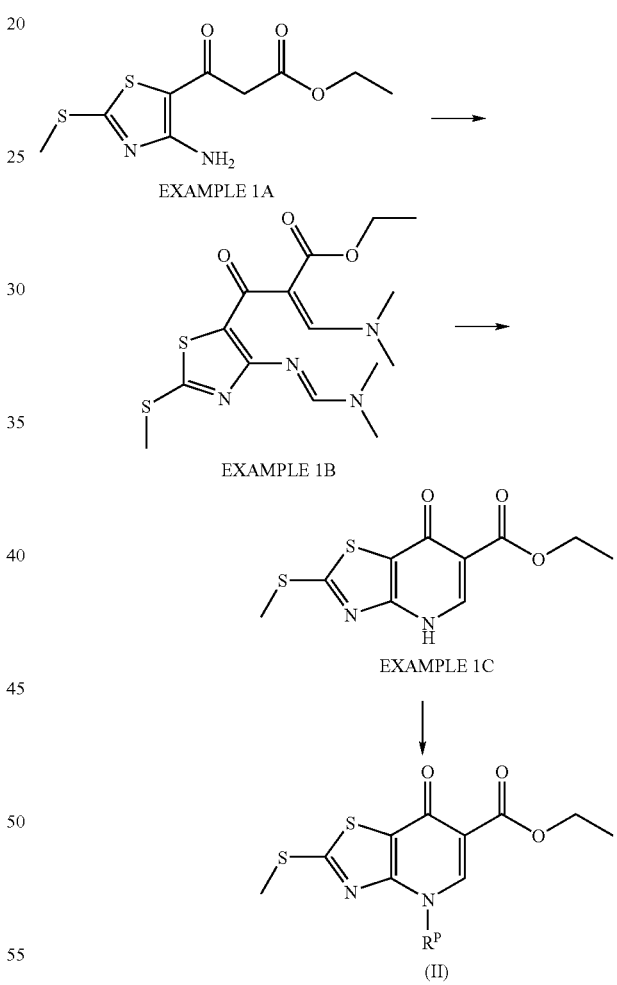

SCHEME 1

EXAMPLE 1A

EXAMPLE 1B

EXAMPLE 1C (II)

Ethyl-4-chloroacetoacetate can be converted to ethyl 3-(4-amino-2-(methylsulfanyl)-1,3-thiazol-5-yl)-3-oxopropanoate (EXAMPLE 1A) by reacting the former and potassium cyanimidodithiocarbonate at about 20° C. to about 30° C., for about 18 hours to about 24 hours, in acetone.

EXAMPLE 1A can be converted to ethyl (2Z)-3-(dimethyl-amino)-2-((4-(((E)-(dimethylamino)methylidene)-amino)-2-(methylsulfanyl)-1,3-thiazol-5-yl)carbonyl)-2-propenoate (EXAMPLE 1B) by reacting the former and N,N-dimethyl-formamide dimethyl acetal at about 100° C. to about 120° C., for about 3 hours to about 5 hours, in toluene.

EXAMPLE 1B can be converted to ethyl 2-(methylsulfanyl)-7-oxo-4,7-dihydro[1,3]thiazolo[4,5-b]pyridine-6-carboxylate (EXAMPLE 1C) by reacting the former and acetic acid at about 20° C. to about 35° C., for about 18 hours to about 24 hours.

EXAMPLE 1C can be converted to compounds having formula (II), in which $R^P$ is a nitrogen protecting group, by reacting the former, a first base, and a nitrogen protecting group precursor. Examples of first bases include sodium carbonate, potassium carbonate, triethylamine, and diisopropylethyl-amine. Examples of nitrogen protecting group precursors include methoxymethyl chloride, para-methoxybenzyloxymethyl chloride, 2,2,2-trichloroethoxymethyl chloride, 2-(trimethylsilyl)ethoxymethyl bromide, 2-(trimethylsilyl)-ethoxymethyl chloride, 3,4-dimethoxybenzyl bromide, 3,4-dimethoxybenzyl chloride, and triphenylmethyl chloride. The reaction is typically conducted at about 25° C. to about 100° C., for about 1 hour to about 24 hours, in solvents such as acetonitrile, ethyl acetate, tetrahydrofuran, N,N-dimethyl-formamide, dimethylsulfoxide, N-methylpyrrolidinone, and mixtures thereof.

SCHEME 2

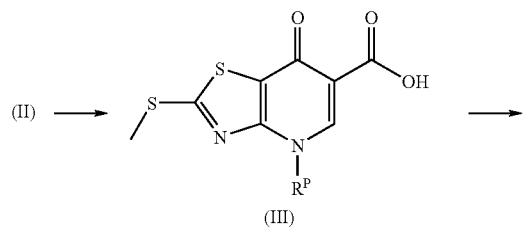

Compounds having formula (II) can be converted to compounds having formula (III) by reacting the former and either a hydroxide base or 1M hydrochloric acid. When using the 1M hydrochloric acid, the reaction is typically conducted at about 90° C. to about 110° C., for about 18 hours to about 24 hours, in acetic acid. When using the hydroxide base, the reaction is typically conducted at about 25° C. to about 100° C., for about 1 hour to about 24 hours, in solvents such as water, N,N-dimethylformamide, dimethylsulfoxide, tetrahydrofuran, dioxane, and a mixture of water and either N,N-dimethylformamide, dimethylsulfoxide, tetrahydrofuran, or dioxane.

Compounds having formula (III) can be converted to compounds having formula (IV) by reacting the former and meta-chloroperbenzoic acid at about 25° C. to about 100° C., for about 1 hour to about 24 hours, in solvents such as dichloromethane, chloroform, carbon tetrachloride, and mixtures thereof.

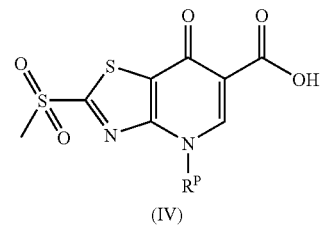

SCHEME 3

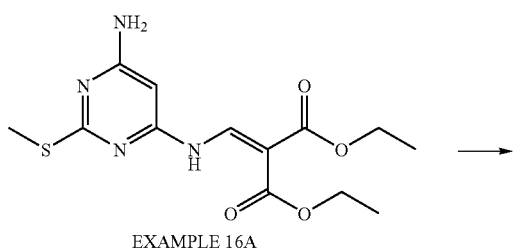
EXAMPLE 16A

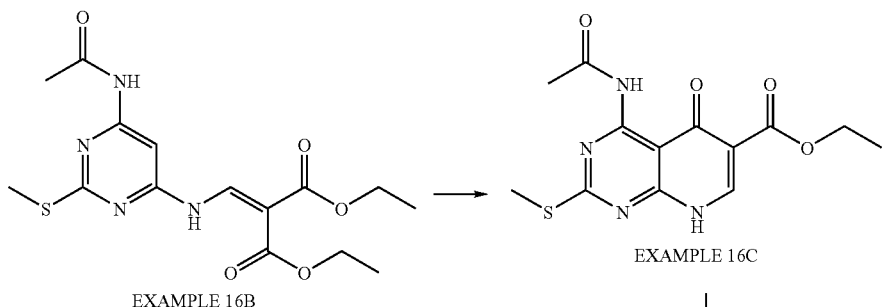
EXAMPLE 16B
EXAMPLE 16C

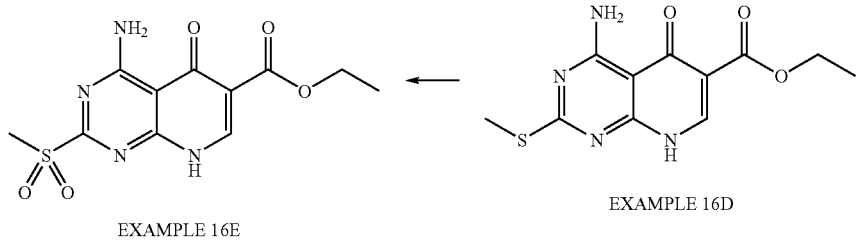

EXAMPLE 16E      EXAMPLE 16D 4,6-Diamino-2-ethylmercaptopyrimidine can be converted to diethyl 2-((((6-amino-2-(methylsulfanyl)-4-pyrimidinyl)amino)methylene)malonate (EXAMPLE 16A) by reacting the former and diethyl ethoxymethylene malonate at about 150° C. to about 170° C., for about 30 minutes to about 1 hour.

EXAMPLE 16A can be converted to diethyl 2-((((6-(acetylamino)-2-(methylsulfanyl)-4-pyrimidinyl)amino)-methylene)malonate (EXAMPLE 16B) by reacting the former and acetic anhydride at about 130° C. to about 150° C., for about 1 hour to about 6 hours.

EXAMPLE 16B can be converted to ethyl 4-(acetylamino)-2-(methylsulfanyl)-5-oxo-5,8-dihydro[2,3-d]pyrimidino-pyridine-6-carboxylate (EXAMPLE 16C) by heating at about 200° C. to about 275° C., for about 20 minutes to about 1 hour, in a 73.5:26.5 (v/v) mixture of phenyl ether and biphenyl.

EXAMPLE 16C can be converted to ethyl 4-amino-2-(methylsulfanyl)-5-oxo-5,8-dihydro[2,3-d]pyrimidinopyridine-6-carboxylate (EXAMPLE 16D) by reacting the former and sodium ethoxide at about 20° C. to about 80° C., for about 20 minutes to about 30 minutes, in absolute ethanol.

EXAMPLE 16D can be converted to ethyl 4-amino-2-(methylsulfonyl)-5-oxo-5,8-dihydro[2,3-d]pyrimidinopyridine-6-carboxylate (EXAMPLE 16E) by reacting the former and meta-chloroperbenzoic acid at about 40° C. about 60° C., for about 10 to about 30 minutes, in ethanol.

Compounds having formula (IV) and EXAMPLE 16E can be interconverted or intraconverted, respectively, to compounds of this invention having formula (I) by reacting the former and a nucleophile. Examples of nucleophiles include compounds having formulas $(M^+)(^-OR^6)$, $(M^+)(^-O(CH_2)R^7)$, $(M^+)(^-O(CH_2)R^8)$, $(M^+)(^-OR^9)$, $(M^+)(^-O(CH_2)R^{10})$, $(M^+)(^-O(CH_2)R^{11})$, $(M^+)(^-SR^6)$, $(M^+)(^-S(CH_2)R^7)$, $(M^+)(^-S(CH_2)R^8)$, $(M^+)(^-SR^9)$, $(M^+)(^-S(CH_2)R^{10})$, $(M^+)(^-S(CH_2)R^{11})$, $NH_3$, $H_2NR^6$, $H_2NR^7$, $H_2NR^8$, $H_2NR^9$, $H_2NR^{10}$, $H_2NR^{11}$, $HN(R^6)_2$, $HN(R^7)_2$, $HN(R^8)_2$, $HN(R^9)_2$, $HN(R^{10})_2$, and $HN(R^{11})_2$, in which M is sodium or potassium and $X^1$ is Cl or Br.

The —NH— and —NH$_2$ moieties of the compounds of this invention can be reacted, with or without the first base, with compounds having formula $ClC(O)R^6$, $ClC(O)R^7$, $ClC(O)R^8$, $ClC(O)R^9$, $ClC(O)R^{10}$, $ClC(O)R^{11}$, $ClC(O)OR^6$, $ClC(O)OR^7$, $ClC(O)OR^8$, $ClC(O)OR^9$, $ClC(O)OR^{10}$, $ClC(O)OR^{11}$, $ClSO_2R^6$, $ClSO_2R^7$, $ClSO_2R^8$, $ClSO_2R^9$, $ClSO_2R^{10}$, or $ClSO_2R^{11}$.

The —CO$_2$H moieties of the compounds of the invention can be reacted with ammonia or an amine having formula $H_2NR^5$ or $HN(R^5)_2$ and a dehydrating agent, with or without the first base, and with or without a promoter. Examples of dehydrating agents include carbonyldiimidazole, 1-(3-(dimethylamino)propyl)-3-ethylcarbodiimide hydrochloride and dicyclohexylcarbodiimide. Examples of promoters include 1-hydroxybenzotriazole and 4-(N,N-dimethylamino)pyridine. The reactions are typically conducted at about 0° C. to about 35° C., for about 1 hour to about 24 hours, in solvents such as N,N-dimethylformamide, tetrahydrofuran, dioxane, water, ethyl acetate, and acetonitrile.

The following examples further embody the compounds and processes of this invention.

EXAMPLE 1A ethyl 3-(4-amino-2-(methylsulfanyl)-1,3-thiazol-5-yl)-3-oxopropanoate A mixture of potassium cyanimidodithiocarbonate (10 g) and ethyl-4-chloroacetoacetate (12.6 g) in acetone (75 mL) at 25° C. was stirred for 18 hours and concentrated. The concentrate was treated with water and extracted with dichloromethane. The extract was washed with water and brine, dried over anhydrous sodium sulfate, filtered, and concentrated. The concentrate was triturated with ethanol, stored at 0° C. for 18 hours, and filtered. $^1$H NMR (300 MHz, CDCl$_3$) δ 6.65 (b, 2H), 4.21 (q, 2H), 3.57 (s, 2H), 2.66 (s, 3H), 1.23 (t, 3H).

EXAMPLE 1B ethyl (2Z)-3-(dimethylamino)-2-((4-(((E)-(dimethylamino)methylidene)amino)-2-(methylsulfanyl)-1,3-thiazol-5-yl)carbonyl)-2-propenoate A mixture of EXAMPLE 1A (8.8 g) and N,N-dimethylformamide dimethyl acetal (15.1 g) in toluene (170 mL) at 110° C. was stirred for 3 hours, concentrated to half volume, cooled, and filtered. $^1$H NMR (300 MHz, CDCl$_3$) δ 8.40 (s, 1H), 7.42 (s, 1H), 3.99 (q, 2H), 3.05 (d, 6H), 2.92 (b, 6H), 2.65 (s, 3H), 1.04 (t, 3H).

EXAMPLE 1C ethyl 2-(methylsulfanyl)-7-oxo-4,7-dihydro[1,3]thiazolo[4,5-b]pyridine-6-carboxylate EXAMPLE 1B (18.5 g) in acetic acid (250 mL) at 25° C. was stirred for 18 hours and filtered. $^1$H NMR (300 MHz, DMSO-d$_6$) δ 8.35 (s, 1H), 4.22 (q, 2H), 2.80 (s, 3H), 1.26 (t, 3H).

EXAMPLE 1D ethyl 4-(4-methoxybenzyl)-2-(methylsulfanyl)-7-oxo-4,7-dihydro[1,3]thiazolo[4,5-b]pyridine-6-carboxylate A mixture of EXAMPLE 1C (6.5 g), potassium carbonate (3.9 g), and 4-methoxybenzyl chloride (11.3 g) in N,N-dimethylformamide (100 mL) at 100° C. was stirred for 4 hours, cooled, poured into water, and extracted with ethyl acetate. The extract was washed with water and brine, dried over anhydrous sodium sulfate, filtered, and concentrated. The concentrate was triturated with 1:1 hexanes/ethyl ether and filtered. $^1$H NMR (300 MHz, CDCl$_3$) δ 8.68 (s, 1H), 7.35 (d, 2H), 6.93 (d, 2H), 5.51 (s, 2H), 4.23 (q, 2H), 3.73 (s, 3H), 2.81 (s, 3H), 1.28 (t, 3H).

EXAMPLE 1E 4-(4-methoxybenzyl)-2-(methylsulfanyl)-7-oxo-4,7-dihydro[1,3]thiazolo[4,5-b]pyridine-6-carboxylic acid EXAMPLE 1D (2.5 g) in acetic acid (42 mL) and 1M hydrochloric acid (24 mL) at 100° C. was stirred for 18 hours, cooled, poured into a mixture of ice and water, and filtered. $^1$H NMR (300 MHz, DMSO-d$_6$) δ 15.01 (br s, 1H), 9.04 (s, 1H), 7.42 (d, 2H), 6.94 (d, 2H), 3.73 (s, 3H), 2.87 (s, 3H).

EXAMPLE 1F 4-(4-methoxybenzyl)-2-(methylsulfonyl)-7-oxo-4,7-dihydro[1,3]thiazolo[4,5-b]pyridine-6-carboxylic acid EXAMPLE 1E (7 g) in chloroform (120 mL) at 25° C. was treated with 77% meta-chloroperbenzoic acid (14.3 g), stirred at 90° C. for 2 hours, cooled, treated with ethyl ether, and filtered. $^1$H NMR (300 MHz, DMSO-d$_6$) δ 14.3 (br s, 1H), 9.27 (s, 1H), 7.50 (d, 2H), 6.96 (d, 2H), 5.75 (s, 2H), 3.7 (s, 3H), 3.6 (s, 3H).

EXAMPLE 1G 1-benzyl-3-pyrrolidinyl methanesulfonate

1-Benzyl-3-pyrrolidinol (1.1 g) in toluene (10 mL) at 0° C. was treated with triethylamine (1 mL) and methanesulfonyl chloride (0.53 mL), warmed to room temperature, washed with saturated aqueous sodium bicarbonate, water, and brine, dried over anhydrous sodium sulfate, and concentrated. $^1$H NMR (300 MHz, DMSO-d$_6$) δ 7.31 (s, 5H), 5.21 (m, 1H), 3.65 (q, 2H), 2.82 (m, 2H), 2.5 (m, 2H), 2.36 (m, 2H), 2.1 (m, 1H).

EXAMPLE 1H 1-benzyl-3-pyrrolidinecarbonitrile

A mixture of EXAMPLE 1G (1.5 g) and tetrabutlyammonium cyanide (3.15 gm) in acetonitrile (25 mL) was heated at 65° C. for 24 hours, poured into saturated aqueous sodium bicarbonate, and extracted with toluene. The extract was washed with distilled water, dried over anhydrous sodium sulfate, and concentrated. $^1$H NMR (300 MHz, CDCl$_3$) δ 7.33 (s, 5H), 3.42 (m, 2H), 2.89 (m, 1H), 2.72 (m, 1H), 1.68 (b, 3H), 1.45 (m, 2H).

EXAMPLE 1I tert-butyl (1-benzyl-3-pyrrolidinyl)methylcarbamate

A mixture of EXAMPLE 1H (3.54 g) and methanol-washed Raney Nickel (16 g) in 20% ammonia in methanol (w/w) (60 mL) at 25° C. in a Paar apparatus was stirred under 60 pounds per square inch of hydrogen gas for 1 hour, filtered through diatomaceous earth (Celite®), and concentrated. The concentrate was dissolved in methanol (30 mL), treated with di-tert-butyl dicarbonate (4.9 g), stirred for 48 hours, poured into distilled water, and extracted with ethyl acetate. The extract was washed with 1% hydrochloric acid, water, and brine, dried over anhydrous sodium sulfate, and concentrated. $^1$H NMR (300 MHz, CDCl$_3$) δ 7.32 (s, 5H), 5.07 (m, 1H), 3.54 (s, 2H), 3.10 (b, 2H), 2.7 (m, 1H), 2.70 (m, 1H), 2.54 (m, 1H), 2.40 (m, 2H), 2.00(b, 1H), 1.80 (b, 1H).

EXAMPLE 1J tert-butyl 3-pyrrolidinylmethylcarbamate

A mixture of EXAMPLE 1I (3.9 g) and 20% Pd/C (1.4 g) in methanol (20 mL) at 25° C. in a Paar apparatus was stirred under 50 pounds per square inch of hydrogen gas for 22 hours, filtered through diatomaceous earth (Celite®), and concentrated. $^1$H NMR (300 MHz, DMSO-d$_6$) δ 2.80–2.70 (m, 5H), 2.41 (m, 1H), 2.09 (m, 1H), 1.73 (m, 1H), 1.37 (s, 9H), 1.25 (m, 1H).

EXAMPLE 1K 2-(3-(R/S)-(((tert-butoxycarbonyl)amino)methyl)-pyrrolidin-1-yl)-4-(4-methoxybenzyl)-7-oxo-4,7-dihydro[1,3]thiazolo[4,5-b]pyridine-6-carboxylic acid A mixture of EXAMPLE 1F (300 mg) and EXAMPLE 1J (500 mg) in absolute ethanol (30 mL) at reflux was stirred for 18 hours, cooled, poured into water, and extracted with dichloromethane. The extract was washed with water and brine, dried over anhydrous sodium sulfate, filtered, and concentrated. The concentrate was flash chromatographed on silica gel with 65:5 chloroform/methanol. $^1$H NMR (300 MHz, DMSO-d$_6$) δ 8.45 (s, 1H), 7.29 (d, 2H), 6.87 (d, 2H), 5.37 (s, 2H), 3.80 (s, 3H), 3.25 (m, 3H), 2.67 (m, 2H), 2.22 (m, 2H), 1.90 (m, 2H), 1.45 (s, 9H).

EXAMPLE 1L 2-(3-(aminomethyl)pyrrolidin-1-yl)-7-oxo-4,7-dihydro[1,3]thiazolo[4,5-b]pyridine-6-carboxylic acid, trifluoroacetic acid salt EXAMPLE 1K (130 mg) in trifluoroacetic acid (15 mL) at 110° C. was stirred for 18 hours, cooled, and concentrated. The concentrate was triturated twice with toluene then with ethyl ether and filtered. $^1$H NMR (300 MHz, DMSO-d$_6$) δ 13.7 (br s 1H), 8.37 (s, 1H), 7.94 (b, 2H), 2.99 (m, 3H), 2.68 (m, 2H), 2.23 (m, 2H), 1.90 (m, 2H).

EXAMPLE 2A tert-butyl 3-pyridinylcarbamate

3-Aminopyridine (2 g) in tetrahydrofuran (20 mL) at 25° C. was treated with 1M sodium bis(trimethylsilylamide) in tetrahydrofuran (46.7 mL), stirred for 15 minutes, treated with di-tert-butyldicarbonate (5 g) in tetrahydrofuran, stirred for 24 hours, and concentrated. The concentrate was treated with 0.1M hydrochloric acid (40 mL) and ethyl acetate (40 mL), and the organic layer was separated, washed with brine, dried over anhydrous sodium sulfate, flitered, and concentrated. The concentrate was flash chromatographed on silica gel with 60:40 ethyl acetate/hexanes. $^1$H NMR (300 MHz, DMSO-d$_6$) δ 8.43 (d, 1H), 8.29 (dd, 1H), 7.98 (m, 1H), 6.57 (b, 1H), 1.53 (s, 9H).

EXAMPLE 2B tert-butyl 3-piperidinylcarbamate

A mixture of tert-butyl 3-pyridinylcarbamate (2.2 g) and 5% rhodium on carbon (200 mg) in ethanol (50 mL) at 25° C. in a paar apparatus was stirred under hydrogen at 60 pounds per square inch for 24 hours, filtered through diatomaceous earth (Celite®), and concentrated. $^1$H NMR (300 MHz, CDCl$_3$) δ 5.86 (b, 1H), 3.59 (b, 1H), 3.07 (dd, 1H), 2.84 (m, 1H), 2.68 (m, 1H), 2.55 (m, 1H), 2.10 (s, 1H), 1.82 (m, 1H), 1.68 (m, 1H), 1.50 (m, 1H), 1.46 (s, 9H).

EXAMPLE 2C 2-(3-((tert-butoxycarbonyl)amino)piperidin-1-yl)-4-(4-methoxybenzyl)-7-oxo-4,7-dihydro[1,3]thiazolo[4,5-b]pyridine-6-carboxylic acid A mixture of EXAMPLE 1F (350 mg) and EXAMPLE 2B (450 mg) in absolute ethanol (30 mL) at reflux was stirred for 18 hours, cooled, poured into water, and extracted with chloroform. The extract was washed with water and brine, dried over anhydrous sodium sulfate, filtered, and concentrated. The concentrate was flash chromatographed on silica gel with 65:5 chloroform/methanol. $^1$H NMR (300 MHz, DMSO-d$_6$) δ 8.84 (s, 1H), 7.48 (d, 2H), 6.92 (d, 2H), 5.49 (s, 2H), 3.73 (s, 2H), 3.53 (b, 2H), 3.43 (b, 4H), 2.90 (d, 1H), 2.78 (d, 1H), 1.5 (b, 1H), 1.42 (d, 9H).

EXAMPLE 2D 2-(3-aminopiperidin-1-yl)-7-oxo-4,7-dihydro[1,3]thiazolo[4,5-b]pyridine-6-carboxylic acid, trifluoroacetic acid salt This example was prepared by substituting EXAMPLE 2C for EXAMPLE 1K in EXAMPLE 1L. $^1$H NMR (300 MHz, DMSO-d$_6$) δ 8.35 (s, 1H), 4.14 (d, 1H), 3.78 (m, 1H), 3.51 (q, 1H), 3.42 (m, 2H), 2.07 (b, 1H), 1.92 (m, 1H), 1.75 (m, 2H).

EXAMPLE 3A tert-butyl 3-piperidinylmethylcarbamate

A mixture of tert-butyl 3-pyridinylmethylcarbamate (4.3 g) and 5% rhodium on carbon (400 mg) in ethanol (50 mL) at 25° C. in a paar apparatus was stirred under hydrogen at 60 pounds per square inch for 27 hours, filtered through diatomaceous earth (Celite®), and concentrated. $^1$H NMR (300 MHz, CDCl$_3$) δ 4.55 (b, 1H), 2.99 (m, 4H), 2.56 (t, 1H), 2.33 (t, 1H), 1.74 (m, 1H), 1.66 (m, 2H), 1.44 (s, 9H).

EXAMPLE 3B 2-(3-(((tert-butoxycarbonyl)amino)methyl)piperidin-1-yl)-4-(4-methoxybenzyl)-7-oxo-4,7-dihydro[1,3]thiazolo[4,5-b]pyridine-6-carboxylic acid This example was prepared by substituting EXAMPLE 3A for EXAMPLE 1J in EXAMPLE 1K. $^1$H NMR (300 MHz, CDCl$_3$) δ 8.43 (s, 1H), 7.28 (d, 2H), 6.88 (d, 2H), 5.35 (s, 2H), 3.80 (s, 2H), 3.28 (m, 1H), 3.15 (m, 2H), 2.77 (m, 1H), 2.07 (b, 1H), 1.84 (m, 3H), 1.44 (d, 9H).

EXAMPLE 3C 2-(3-(aminomethyl)piperidin-1-yl)-7-oxo-4,7-dihydro[1,3]thiazolo[4,5-b]pyridine-6-carboxylic acid, trifluoroacetic acid salt This example was prepared by substituting EXAMPLE 3B for EXAMPLE 1K in EXAMPLE 1L. $^1$H NMR (300 MHz, CDCl$_3$) δ 8.80 (s, 1H), 3.5 (b, 3H), 3.24 (m, 2H), 2.31 (m, 1H), 2.16 (m, 1H), 2.00 (m, 1H), 1.81(m, 1H), 1.60 (m, 1H).

EXAMPLE 4

2-(methyl(2-phenylethyl)amino)-7-oxo-4,7-dihydro[1,3]thiazolo[4,5-b]pyridine-6-carboxylic acid This example was prepared by substituting N-methyl-2-phenylethanamine for EXAMPLE 1J in EXAMPLE 1K and reacting the product therefrom and trifluoroacetic acid as described for EXAMPLE 1K in EXAMPLE 1L. $^1$H NMR (500 MHz, DMSO-d$_6$) δ 16.02 (s, 1H), 13.81 (s, 1H), 8.33 (s, 1H), 7.31 (m, 4H), 7.22 (m, 1H), 3.81 (m, 2H), 3.14 (s, 3H), 2.98 (t, 2H).

EXAMPLE 5

2-((2-(3,4-dimethoxyphenyl)ethyl)(methyl)amino)-7-oxo-4,7-dihydro[1,3]thiazolo[4,5-b]pyridine-6-carboxylic acid This example was prepared by substituting N-(2-(3,4-dimethoxyphenyl)ethyl)-N-methylamine for EXAMPLE 1J in EXAMPLE 1K and reacting the product therefrom and trifluoroacetic acid as described for EXAMPLE 1K in EXAMPLE IL. $^1$H NMR (500 MHz, DMSO-d$_6$) δ 15.92 (s, 1H), 13.78 (s, 1H), 8.33 (s, 1H), 6.89 (d, 1H), 6.87 (d, 1H), 6.78 (dd, 1H), 3.80 (m, 2H), 3.73 (s, 3H), 3.70 (s, 3H), 3.14 (s, 3H), 2.91 (t, 2H).

EXAMPLE 6

2-(4-(2-fluorophenyl)piperazin-1-yl)-7-oxo-4,7-dihydro[1,3]thiazolo[4,5-b]pyridine-6-carboxylic acid, trifluoroacetic acid salt This example was prepared by substituting 1-(2-fluorophenyl)piperazine for EXAMPLE 1J in EXAMPLE 1K and reacting the product therefrom and trifluoroacetic acid as described for EXAMPLE 1K in EXAMPLE 1L. $^1$H NMR (500 MHz, DMSO-d$_6$) δ 15.82 (s, 1H), 13.86 (s, 1H), 8.38 (s, 1H), 7.10 (m, 4H), 3.83 (m, 4H), 3.19 (m, 4H).

EXAMPLE 7

2-(4-(2-chlorophenyl)piperazin-1-yl)-7-oxo-4,7-dihydro[1,3]thiazolo[4,5-b]pyridine-6-carboxylic acid, trifluoroacetic acid salt This example was prepared by substituting 1-(2-chlorophenyl)piperazine for EXAMPLE 1J in EXAMPLE 1K and reacting the product therefrom and trifluoroacetic acid as described for EXAMPLE 1K in EXAMPLE 1L. $^1$H NMR NMR (500 MHz DMSO-d$_6$) δ 15.88 (s, 1H), 13.84 (s, 1H), 8.38 (s, 1H), 7.46 (dd, 1H), 7.33 (m, 1H), 7.21 (dd, 1H), 7.10 (m, 1H), 3.83 (m, 4H), 3.16 (m, 4H).

EXAMPLE 8

2-(2-fluoro-4-methylanilino)-7-oxo-4,7-dihydro[1,3]thiazolo[4,5-b]pyridine-6-carboxylic acid This example was prepared by substituting 2-fluoro-4-methylaniline for EXAMPLE 1J in EXAMPLE 1K and reacting the product therefrom and trifluoroacetic acid as described for EXAMPLE 1K in EXAMPLE 1L. $^1$H NMR (500 MHz DMSO-d$_6$) δ 15.79 (s, 1H), 14.01 (s, 1H), 11.00 (s, 1H), 8.40 (s, 1H), 7.98 (t, 1H), 7.20 (dd, 1H), 7.09 (d, 1H), 2.34 (s, 3H).

EXAMPLE 9

2-(3-fluoro-4-methylanilino)-7-oxo-4,7-dihydro[1,3]thiazolo[4,5-b]pyridine-6-carboxylic acid This example was prepared by substituting 3-fluoro-4-methylaniline for EXAMPLE 1J in EXAMPLE 1K and reacting the product therefrom and trifluoroacetic acid as described for EXAMPLE 1K in EXAMPLE 1L. $^1$H NMR (500 MHz DMSO-d$_6$) δ 15.73 (s, 1H), 14.10 (s, 1H), 11.38 (s, 1H), 8.45 (s, 1H), 7.77 (dd, 1H), 7.31 (t, 1H), 7.26 (dd, 1H), 2.22 (s, 3H).

EXAMPLE 10

2-(4-bromo-3-methylanilino)-7-oxo-4,7-dihydro[1,3]thiazolo[4,5-b]pyridine-6-carboxylic acid This example was prepared by substituting 4-bromo-3-methylaniline for EXAMPLE 1J in EXAMPLE 1K and reacting the product therefrom and trifluoroacetic acid as described for EXAMPLE 1K in EXAMPLE 1L. $^1$H NMR (500 MHz DMSO-d$_6$) δ 15.69 (s, 1H), 14.08 (s, 1H), 11.35 (s, 1H), 8.45 (s, 1H), 7.69 (d, 1H), 7.61 (d, 1H), 7.51 (dd, 1H), 2.38 (s, 3H).

EXAMPLE 11

7-oxo-2-(4-propoxyanilino)-4,7-dihydro[1,3]thiazolo[4,5-b]pyridine-6-carboxylic acid This example was prepared by substituting 4-propoxyaniline for EXAMPLE 1J in EXAMPLE 1K and reacting the product therefrom and trifluoroacetic acid as described for EXAMPLE 1K in EXAMPLE 1L. $^1$H NMR (500 MHz DMSO-d$_6$) δ 15.81 (s, 1H), 13.97 (s, 1H), 11.14 (s, 1H), 8.39 (s, 1H), 7.56 (d, 2H), 6.99 (d, 2H), 3.94 (t, 2H), 1.73 (m, 2H), 0.99 (t, 3H).

EXAMPLE 12

2-(4-(methylsulfanyl)anilino)-7-oxo-4,7-dihydro[1,3]thiazolo[4,5-b]pyridine-6-carboxylic acid This example was prepared by substituting 4-(methylsulfanyl)aniline for EXAMPLE 1J in EXAMPLE 1K and reacting the product therefrom and trifluoroacetic acid as described for EXAMPLE 1K in EXAMPLE 1L. $^1$H NMR (500 MHz DMSO-d$_6$) δ 15.76 (s, 1H), 14.05 (s, 1H), 11.31 (s, 1H), 8.42 (s, 1H), 7.66 (d, 2H), 7.34 (d, 2H), 2.49 (s, 3H).

EXAMPLE 13A 2-(methylsulfanyl)-4-pyrimidinamine

A mixture of 4-chloro-2-methylsulfanylpyrimidine (8 g) and 7N ammonia in methanol (100 mL) at 100° C. was stirred for 2 days in a sealed tube, cooled, concentrated, treated with water, and extracted with ethyl acetate. The extract was washed with brine, dried over anhydrous sodium sulfate, and concentrated. The concentrate was triturated with ethyl ether and filtered. $^1$H NMR (300 MHz, CDCl$_3$) δ 8.06 (d, 1H), 6.12 (d, 1H), 4.83 (s, 2H), 2.51 (s, 3H).

EXAMPLE 13B ethyl 2-(((2-(methylsulfanyl)-4-pyrimidinyl)amino)-methylene)malonate A mixture of EXAMPLE 13A (3 g) and diethyl ethoxymethylene malonate (5.15 mL) at 150° C. was stirred for 15 hours, cooled and filtered. The filtrant was recrystallized from ethanol/ethyl ether. $^1$H NMR (300 MHz, CDCl$_3$) δ 9.11 (d, 1H), 8.34 (d, 1H), 6.46 (d, 1H), 4.30 (m, 4H), 2.58 (s, 3H), 1.36 (m, 6H).

EXAMPLE 13C ethyl 2-(methylsulfanyl)-5-oxo-5,8-dihydro[2,3-d]pyrimidinopyridine-6-carboxylate EXAMPLE 13B (1.5 g) in 73.5:26.5 (v/v) phenyl ether/biphenyl (15 mL) at 250° C. was stirred for 90 minutes, cooled, and filtered. $^1$H NMR (300 MHz, DMSO-d$_6$) δ 9.14 (s, 1H), 8.42 (s, 1H), 4.22 (q, 2H), 2.60 (s, 3H), 1.27 (m, 3H).

EXAMPLE 13D ethyl 2-(methylsulfonyl)-5-oxo-5,8-dihydro[2,3-d]pyrimidinopyridine-6-carboxylate EXAMPLE 13C (100 mg) in dimethylacetamide (1.5 mL) at 25° C. was treated with meta-chloroperbenzoic acid (325 mg) in dimethylacetamide (0.5 mL), stirred for 2 hours, and concentrated. The concentrate was triturated with ethyl ether and methanol and filtered. $^1$H NMR (300 MHz, DMSO-d$_6$) δ 9.53 (s, 1H), 8.63 (s, 1H), 4.24 (q, 2H), 3.46 (s, 3H), 1.29 (t, 3H).

EXAMPLE 13E ethyl 5-oxo-2-(pyrrolidin-1-yl)-5,8-dihydro[2,3-d]pyrimidinopyridine-6-carboxylate A mixture of EXAMPLE 13D (37 mg) and pyrrolidine (88.5 mg) in dimethylacetamide (0.5 mL) at 25° C. was stirred for 30 minutes and concentrated. The concentrate was triturated with ether and methanol and filtered. $^1$H NMR (300 MHz, DMSO-$d_6$) δ 8.97 (s, 1H), 8.24 (s, 1H), 4.18 (q, 2H), 3.60 (m, 4H), 1.96 (m, 4H), 1.25 (t, 3H).

EXAMPLE 13F 2-(pyrrolidin-1-yl)-5-oxo-5,8-dihydro[2,3-d]pyrimidinopyridine-6-carboxylic acid, Citric acid salt A mixture of EXAMPLE 13E (24.3 mg) and lithium hydroxide monohydrate (7.1 mg) in iso-propanol (0.5 mL) and water (0.15 mL) at 85° C. was stirred for 1 hour, treated with 2N sodium hydroxide (1 mL), stirred for 30 minutes, cooled, and concentrated. The concentrate was treated with concentrated aqueous citric acid (2 mL) and filtered. $^1$H NMR (300 MHz, DMSO-$d_6$) δ 14.86 (br s, 1H), 9.18 (s, 1H), 8.48 (s, 1H), 3.61 (m, 4H), 1.98 (m, 4H).

EXAMPLE 14A ethyl 2-(azetidin-1-yl)-5-oxo-5,8-dihydro[2,3-d]pyrimidinopyridine-6-carboxylate This example was prepared by substituting azetidine for pyrrolidine in EXAMPLE 13E. $^1$H NMR (300 MHz, DMSO-$d_6$) δ 8.95 (s, 1H), 8.23 (s, 1H), 4.17 (m, 6H), 2.35 (m, 2H), 1.25 (t, 3H).

EXAMPLE 14B 2-(azetidin-1-yl)-5-oxo-5,8-dihydro[2,3-d]pyrimidinopyridine-6-carboxylic acid This example was prepared by substituting EXAMPLE 14A for EXAMPLE 13E in EXAMPLE 13F. $^1$H NMR (300 MHz, DMSO-$d_6$) δ 14.83 (s, 1H), 9.15 (s, 1H), 8.48 (s, 1H), 4.21 (m, 4H), 2.38 (m, 2H).

EXAMPLE 15A ethyl 2-(3-aminopyrrolidin-1-yl)-5-oxo-5,8-dihydro[2,3-d]pyrimidinopyridine-6-carboxylate This example was prepared by substituting (±)-tert-butyl 3-pyrrolidinylcarbamate for pyrrolidine in EXAMPLE 13E, reacting the product therefrom and 5% trifluoroacetic acid in dichloromethane for 3 hours at 25° C., and purifying the product by chromatography for 12 minutes on a 40 mm×100 mm Waters Symmetry $C_8$ column (7 µm particle size) at a flow rate of 70 mL/minute with a gradient of 10% to 100% acetonitrile:0.1% (v/v) aqueous trifluoroacetic acid. $^1$H NMR (300 MHz, DMSO-$d_6$) δ 9.02 (s, 1H), 8.26 (d, 1H), 8.05 (s, 2H), 4.19 (q, 2H), 3.97 (s, 1H), 3.79 (m, 4H), 2.33 (m, 1H), 2.09 (m, 1H), 1.26 (t, 3H).

EXAMPLE 15B 2-(3-aminopyrrolidin-1-yl)-5-oxo-5,8-dihydro[2,3-d]pyrimidinopyridine-6-carboxylic acid, citric acid salt This example was prepared by substituting EXAMPLE 15A for EXAMPLE 13E in EXAMPLE 13F. $^1$H NMR (300 MHz, CD$_3$OD) δ 9.28 (d, 1H), 8.65 (s, 1H), 4.07 (m, 1H), 3.92 (m, 4H), 2.86 (m, 4H (citrate)), 2.53 (m, 1H), 2.22 (m, 1H).

EXAMPLE 16A diethyl 2-(((6-amino-2-(methylsulfanyl)-4-pyrimidinyl)amino)methylene)malonate A mixture of 4,6-diamino-2-ethylmercaptopyrimidine (9.95 g) and diethyl ethoxymethylene malonate (13.77 g) at 165° C. was stirred for 40 minutes, cooled to 135° C., stirred for 60 minutes, cooled to 25° C., and added to refluxing ethanol (700 mL). This mixture was treated with decolorizing carbon (NORIT®) stirred for 30 minutes, cooled, filtered, concentrated to 300 mL, heated until homogeneous, cooled, treated with water until cloudy, stored at 0° C. for 18 hours, and filtered. $^1$H NMR (300 MHz, DMSO-$d_6$) δ 10.41 (d, 1H), 8.96 (d, 1H), 6.98 (s, 2H), 5.97 (s, 1H), 4.21 (q, 2H), 4.12 (q, 2H), 2.43 (s, 3H), 1.26 (t, 3H), 1.23 (t, 3H).

EXAMPLE 16B diethyl 2-(((6-(acetylamino)-2-(methylsulfanyl)-4-pyrimidinyl)amino)methylene)malonate A mixture of EXAMPLE 16A (9.91 g) and acetic anhydride (150 mL) at reflux was stirred for 16 hours, treated with additional acetic anhydride (60 mL), refluxed for 5 hours, cooled and concentrated. The concentrate was dissolved in 9:1 ethanol/ethyl acetate (100 mL), stored at 0° C. for 18 hours, and filtered. $^1$H NMR (300 MHz, DMSO-$d_6$) δ 10.65 (d, 1H), 8.90 (d, 1H), 7.66 (s, 1H), 4.23 (q, 2H), 4.14 (q, 2H), 2.52 (s, 3H), 2.26 (s, 1H), 2.11 (s, 3H), 1.27 (t, 3H), 1.23 (t, 3H).

EXAMPLE 16C ethyl 4-(acetylamino)-2-(methylsulfanyl)-5-oxo-5,8-dihydro[2,3-d]pyrimidinopyridine-6-carboxylate EXAMPLE 16B (4 g) in 73.5:26.5 (v/v) phenyl ether/biphenyl (90 mL) at 250° C. was stirred for 20 minutes, cooled, diluted with ethyl ether (300 mL), stored at 0° C. for 1 hour, and filtered. A solution of the filtrant in ethylene glycol dimethyl ether (600 mL) at 80° C. was treated with decolorizing carbon (NORIT®), stirred for 30 minutes, filtered, concentrated to 80 mL, cooled to 0° C., and filtered. $^1$H NMR (500 MHz, CDCl$_3$) δ 8.39 (s, 1H), 4.33 (q, 2H), 2.56 (s, 3H), 2.52 (s, 3H), 1.35 (t, 3H).

EXAMPLE 16D ethyl 4-amino-2-(methylsulfanyl)-5-oxo-5,8-dihydro[2,3-d]pyrimidinopyridine-6-carboxylate EXAMPLE 16C (900 mg) in absolute ethanol (125 mL) at 25° C. was treated with 21% (w/w) sodium ethoxide in ethanol (2.9 mL), heated at reflux for 20 minutes, cooled, concentrated to 30 mL, adjusted to pH 7 with acetic acid, and filtered. The filtrant was dissolved in hot 4:1 ethanol:water (20 mL), filtered hot, cooled, and filtered. $^1$H NMR (500 MHz, CDCl$_3$) δ 9.45 (d, 1H), 8.21 (s, 1H), 8.18 (d, 1H), 4.20 (q, 2H), 2.48 (s, 3H), 1.26 (t, 3H).

EXAMPLE 16E ethyl 4-amino-2-(methylsulfonyl)-5-oxo-5,8-dihydro [2,3-d]pyrimidinopyridine-6-carboxylate EXAMPLE 16D (590 mg) in absolute ethanol (60 mL) was treated with 70% 3-chloroperoxybenzoic acid (1.25 g), warmed to 50° C. for 18 hours, diluted with ethyl ether (100 mL), and filtered. $^1$H NMR (300 MHz, DMSO-$d_6$) δ 9.81 (d, 1H), 8.87 (d, 1H), 8.41 (s, 1H), 4.21 (q, 2H), 2.31 (s, 3H), 1.27 (t, 3H).

EXAMPLE 16F ethyl 4-amino-5-oxo-2-(pyrrolidin-1-yl)-5,8-dihydro [2,3-d]pyrimidinopyridine-6-carboxylate A mixture of EXAMPLE 16E (80 mg) and pyrrolidine (96 mg) in dimethylacetamide (5 mL) at 25° C. was stirred for 24 hours and concentrated. The concentrate was triturated with cold ethyl ether and filtered. $^1$H NMR (300 MHz, DMSO-$d_6$) δ 9.32 (m, 2H), 8.04 (s, 1H), 4.16 (q, 2H), 3.47 (m, 4H), 1.89 (m, 4H), 1.24 (t, 3H).

EXAMPLE 16G 4-amino-5-oxo-2-(pyrrolidin-1-yl)-5,8-dihydro[2,3-d]pyrimidinopyridine-6-carboxylic acid A mixture of EXAMPLE 16F (170 mg) and 2N sodium hydroxide (8 mL) in absolute ethanol (4 mL) was stirred at 90° C. for 2 hours, cooled to 25° C., adjusted to pH 7 with acetic acid, cooled to 0° C., and filtered. $^1$H NMR (300 MHz, DMSO-$d_6$) δ 8.82 (s, 1H), 8.50 (s, 1H), 7.31 (s, 1H), 7.31 (s, 1H), 3.48 (m, 4H), 1.88 (m, 4H).

EXAMPLE 17A ethyl 4-amino-2-(azetidin-1-yl)-5-oxo-5,8-dihydro [2,3-d]pyrimidinopyridine-6-carboxylate This example was prepared by substituting azetidine for pyrrolidine in EXAMPLE 16F. $^1$H NMR (500 MHz, DMSO-$d_6$) δ 8.30 (s, 1H), 4.33 (s, 2H), 4.32 (s, 4H), 1.39 (t, 3H), 2.50 (m, 2H).

EXAMPLE 17B 2-(azetidin-1-yl)-4-amino-5-oxo-5,8-dihydro[2,3-d] pyrimidinopyridine-6-carboxylic acid This example was prepared by substituting EXAMPLE 17A EXAMPLE 16F in EXAMPLE 16G. $^1$H NMR (300 MHz, DMSO-$d_6$) δ 8.39 (s, 1H), 4.04 (t, 4H), 2.50 (s, 1H), 1.91 (s, 2H).

EXAMPLE 18 ethyl 2-(3-aminopyrrolidin-1-yl)-4-amino-5-oxo-5, 8-dihydro[2,3-d]pyrimidinopyridine-6-carboxylate This example was prepared by substituting (±)-tert-butyl 3-pyrrolidinylcarbamate for pyrrolidine in EXAMPLE 16F, reacting the product therefrom and 50% trifluoroacetic acid in dichloromethane at 25° C. for 16 hours, and concentrating. $^1$H NMR (500 MHz, DMSO-$d_6$) δ 8.09 (d, 1H), 7.69 (dd, 2H), 4.17 (q, 2H), 3.65 (m, 4H), 2.26 (m, 3H), 2.04 (m, 2H), 1.25 (t, 3H).

EXAMPLE 19

2-(3-aminopyrrolidin-1-yl)-4-amino-5-oxo-5,8-dihydro[2,3-d]pyrimidinopyridine-6-carboxylic acid This example was prepared by substituting EXAMPLE 18 for EXAMPLE 16F in EXAMPLE 16G. $^1$H NMR (500 MHz, DMSO-$d_6$) δ 8.67 (s, 1H), 8.33 (d, 1H), 8.15 (m, 2H), 3.69 (m, 4H), 2.29 (dd, 3H), 2.07 (m, 2H).

EXAMPLE 20

2-(1-benzylhexahydropyrrolo[3,4-b]pyrrol-5(1H)-yl)-4-amino-5-oxo-5,8-dihydropyrido[2,3-d]pyrimidine-6-carboxylic acid A mixture of EXAMPLE 16E (84 mg) in dimethyl acetamide (5 mL) at 25° C. was treated with 1-benzyl-octahydropyrrolo[3,4-b]pyrrole (280 mg) in diethyl acetamide (2 mL), stirred for 40 hours, and concentrated. The concentrate was treated with 2N sodium hydroxide (30 mL), stirred at 90° C. for 16 hours, concentrated to one-half volume, adjusted to pH 7 with acetic acid, cooled, triturated with cold ethyl ether, and filtered. $^1$H NMR (500 MHz, DMSO-$d_6$) δ 8.88 (s, 1H), 8.54 (s, 1H), 7.20 (m, 5H), 3.92 (d, 2H), 3.72 (dd, 4H), 3.39 (m, 2H), 3.15 (d, 1H), 2.85 (d, 1H), 1.24 (s, 2H).

These examples are merely illustrative of this invention and are not intended to limit the same to the specifically embodied compounds and processes. Variations and changes which are obvious to one skilled in the art are intended to be within the scope of this invention as defined in the appended claims.

The invention claimed is:

1. A compound having formula (I),

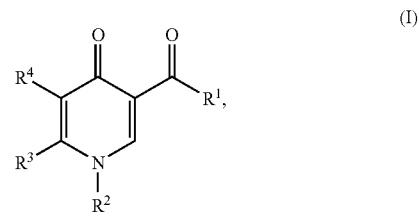

or a salt thereof, in which $R^1$ is —OH, —$OR^5$, —$NH_2$, —$NHR^5$, or —$N(R^5)_2$;

$R^2$ is hydrogen, tert-butyl, —O(allyl), (4-methoxyphenyl)methyl, or (2,4-dimethoxyphenyl)methyl;

$R^3$ and $R^4$ together are thiazole which is substituted with one or two independently selected $R^6$, $R^7$, $R^8$, $R^9$, $R^{10}$, $R^{11}$, —$OR^6$, —$O(CH_2)R^7$, —$O(CH_2)R^8$, —$OR^9$, —$O(CH_2)R^{10}$, —$O(CH_2)R^{11}$, —$SR^6$, —$S(CH_2)R^7$, —$S(CH_2)R^8$, —$SR^9$, —$S(CH_2)R^{10}$, —$S(CH_2)R^{11}$, —$S(O)R^6$, —$S(O)(CH_2)R^7$, —$S(O)(CH_2)R^8$, —$S(O)R^9$, —$S(O)(CH_2)R^{10}$, —$S(O)(CH_2)R^{11}$, —$SO_2R^6$, —$SO_2(CH_2)R^7$, —$SO_2(CH_2)R^8$, —$SO_2R^9$, —$SO_2(CH_2)R^{10}$, —$SO_2(CH_2)R^{11}$, —$CO(O)R^6$, —$C(O)OR^7$, —$C(O)OR^8$, —$CO(O)R^9$, —$C(O)OR^{10}$, —$C(O)OR^{11}$, —$NH_2$, —$NHR^6$, —$NHR^7$, —$NHR^8$, —$NHR^9$, —$NHR^{10}$, —$NHR^{11}$, —$NHC(O)R^6$, —$NHC(O)R^7$, —$NHC(O)R^8$, —$NHC(O)R^9$, —$NHC(O)R^{10}$, —$NHC(O)R^{11}$, —$NHC(O)OR^6$, —$NHC(O)OR^7$, —$NHC(O)OR^8$, —$NHC(O)OR^9$, —$NHC(O)OR^{10}$, —$NHC(O)OR^{11}$, —$NHSO_2R^6$, —$NHSO_2R^7$, —$NHSO_2R^8$, —NHSO$_2$R$^9$, —NHSO$_2$R$^{10}$, —NHSO$_2$R$^{11}$, —N(R$^6$)$_2$, —N(R$^7$)$_2$, —N(R$^8$)$_2$, —N(R$^9$)$_2$, —N(R$^{10}$)$_2$, or —N(R$_{11}$)$_2$ substituents;

R$^5$ is C$_1$-alkyl, C$_2$-alkyl, C$_3$-alkyl, C$_4$-alkyl, C$_5$-alkyl, or C$_6$-alkyl;

R$^6$ is C$_1$-alkyl, C$_2$-alkyl, C$_3$-alkyl, C$_4$-alkyl, C$_5$-alkyl, or C$_6$-alkyl, each of which is unsubstituted or substituted with one —F, —Cl, —Br, —I, —OH, —OR$^{6a}$, —NH$_2$, —NHR$^{6a}$, —N(R$^{6a}$)$_2$, R$^{12}$, R$^{13}$, or R$^{14}$ substituent;

R$^{6a}$ is C$_1$-alkyl, C$_2$-alkyl, C$_3$-alkyl, C$_4$-alkyl, C$_5$-alkyl, C$_6$-alkyl, or R$^{6b}$;

R$^{6b}$ is C$_1$-alkyl, C$_2$-alkyl, C$_3$-alkyl, C$_4$-alkyl, C$_5$-alkyl, or C$_6$-alkyl, each of which is substituted with one or two independently selected —F, —Cl, —Br, —I, —OH, =O, —OR$^{6c}$, —NH$_2$, —NHR$^{6c}$, —N(R$^{6c}$)$_2$, or R$^{6d}$ substituents;

R$^{6c}$ is C$_1$-alkyl, C$_2$-alkyl, C$_3$-alkyl, C$_4$-alkyl, C$_5$-alkyl, or C$_6$-alkyl;

R$^{6d}$ is phenyl, furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl;

R$^7$ is C$_2$-alkenyl, C$_3$-alkenyl, C$_4$-alkenyl, C$_5$-alkenyl, or C$_6$-alkenyl, each of which is unsubstituted or substituted with one —F, —Cl, —Br, —I, —OH, —OR$^{7a}$, —NH$_2$, —NHR$^{7a}$, —N(R$^{7a}$)$_2$, R$^{12}$, R$^{13}$, or R$^{14}$ substituent;

R$^{7a}$ is C$_1$-alkyl, C$_2$-alkyl, C$_3$-alkyl, C$_4$-alkyl, C$_5$-alkyl, C$_6$-alkyl, or R$^{7b}$;

R$^{7b}$ is C$_1$-alkyl, C$_2$-alkyl, C$_3$-alkyl, C$_4$-alkyl, C$_5$-alkyl, or C$_6$-alkyl, each of which is substituted with one or two independently selected —F, —Cl, —Br, —I, —OH, =O, —OR$^{7c}$, —NH$_2$, —NHR$^{7c}$, —N(R$^{7c}$)$_2$, or R$^{7d}$ substituents;

R$^{7c}$ is C$_1$-alkyl, C$_2$-alkyl, C$_3$-alkyl, C$_4$-alkyl, C$_5$-alkyl, or C$_6$-alkyl;

R$^{7d}$ is phenyl, furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl;

R$^8$ is C$_2$-alkynyl, C$_3$-alkynyl, C$_4$-alkynyl, C$_5$-alkynyl, or C$_6$-alkynyl, each of which is unsubstituted or substituted with one —F, —Cl, —Br, —I, —OH, —OR$^{8a}$, —NH$_2$, —NHR$^{8a}$, —N(R$^{8a}$)$_2$, R$^{12}$, R$^{13}$, or R$^{14}$ substituent;

R$^{8a}$ is C$_1$-alkyl, C$_2$-alkyl, C$_3$-alkyl, C$_4$-alkyl, C$_5$-alkyl, C$_6$-alkyl, or R$^{8b}$;

R$^{8b}$ is C$_1$-alkyl, C$_2$-alkyl, C$_3$-alkyl, C$_4$-alkyl, C$_5$-alkyl, or C$_6$-alkyl, each of which is substituted with one or two independently selected —F, —Cl, —Br, —I, —OH, =O, —OR$^{8c}$, —NH$_2$, —NHR$^{8c}$, —N(R$^{8c}$)$_2$, or R$^{8d}$ substituents;

R$^{8c}$ is C$_1$-alkyl, C$_2$-alkyl, C$_3$-alkyl, C$_4$-alkyl, C$_5$-alkyl, or C$_6$-alkyl;

R$^{8d}$ is phenyl, furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl;

R$^9$ is phenyl which is unfused or fused with cyclopentane, cyclohexane, cyclopentene, cyclohexene, benzene, naphthylene, furan, imidazole, isothiazole, isoxazole, oxazole, pyrazine, pyrazole, pyridazine, pyridine, pyrimidine, pyrrole, thiazole, or thiophene, in which each ring is unsubstituted or substituted with one or two or three or four independently selected R$^{9a}$, —F, —Cl, —Br, —I, —CN, —OH, —OR$^{9a}$, —NH$_2$, —NHR$^{9a}$, —N(R$^{9a}$)$_2$, —NO$_2$, —CF$_3$, —OCF$_3$, —SR$^{9a}$, —S(O)R$^{9a}$, —SO$_2$R$^{9a}$, —C(O)R$^{9a}$, —C(O)OH, —C(O)OR$^{9a}$, —C(O)NH$_2$, —C(O)NHR$^{9a}$, —C(O)N(R$^{9a}$)$_2$, R$^{15}$, or R$^{16}$ substituents;

R$^{9a}$ is C$_1$-alkyl, C$_2$-alkyl, C$_3$-alkyl, C$_4$-alkyl, C$_5$-alkyl, C$_6$-alkyl, or R$^{9b}$;

R$^{9b}$ is C$_1$-alkyl, C$_2$-alkyl, C$_3$-alkyl, C$_4$-alkyl, C$_5$-alkyl, or C$_6$-alkyl, each of which is substituted with one or two independently selected —F, —Cl, —Br, —I, —OH, =O, —OR$^{9c}$, —NH$_2$, —NHR$^{9c}$, —N(R$^{9c}$)$_2$, or R$^{9d}$ substituents;

R$^{9c}$ is C$_1$-alkyl, C$_2$-alkyl, C$_3$-alkyl, C$_4$-alkyl, C$_5$-alkyl, or C$_6$-alkyl;

R$^{9d}$ is phenyl, furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl;

R$^{10}$ is furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl, each of which is unfused or fused with benzene, naphthylene, furan, imidazole, isothiazole, isoxazole, oxazole, pyrazine, pyrazole, pyridazine, pyridine, pyrimidine, pyrrole, thiazole, or thiophene, in which each ring is unsubstituted or substituted with one or two or three independently selected R$^{10a}$, —F, —Cl, —Br, —I, —CN, —OH, —OR$^{10a}$, —NH$_2$, —NHR$^{10a}$, —N(R$^{10a}$)$_2$, —NO$_2$, —CF$_3$, —OCF$_3$, —SR$^{10a}$, —S(O)R$^{10a}$, —SO$_2$R$^{10a}$, —C(O)R$^{10a}$, —C(O)OH, —C(O)OR$^{10a}$, —C(O)NH$_2$, —C(O)NHR$^{10a}$, —C(O)N(R$^{10a}$)$_2$, R$^{15}$, or R$^{16}$ substituents;

R$^{10a}$ is C$_1$-alkyl, C$_2$-alkyl, C$_3$-alkyl, C$_4$-alkyl, C$_5$-alkyl, C$_6$-alkyl, or R$^{10b}$;

R$^{10b}$ is C$_1$-alkyl, C$_2$-alkyl, C$_3$-alkyl, C$_4$-alkyl, C$_5$-alkyl, or C$_6$-alkyl, each of which is substituted with one or two independently selected —F, —Cl, —Br, —I, —OH, =O, —OR$^{10c}$, —NH$_2$, —NHR$^{10c}$, —N(R$^{10c}$)$_2$, or R$^{10d}$ substituents;

R$^{10c}$ is C$_1$-alkyl, C$_2$-alkyl, C$_3$-alkyl, C$_4$-alkyl, C$_5$-alkyl, or C$_6$-alkyl;

R$^{10d}$ is phenyl, furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl;

R$^{11}$ is aziridinyl, azetidinyl, pyrrolidinyl, piperidinyl, or piperazinyl, each of which is unfused or fused with benzene, aziridine, azetidine, pyrrolidine, piperidine, or piperazine, in which each ring is unsubstituted or substituted with one or two or three independently selected R$^{11a}$, —F, —Cl, —Br, —I, —CN, —OH, =O, —OR$^{11a}$, —NH$_2$, —NHR$^{11a}$, —N(R$^{11a}$)$_2$, —NO$_2$, —CF$_3$, —OCF$_3$, —SR$^{11a}$, —S(O)R$^{11a}$, —SO$_2$R$^{11a}$, —C(O)R$^{11a}$, —C(O)OH, —C(O)OR$^{11a}$, —C(O)NH$_2$, —C(O)NHR$^{11a}$, —C(O)N(R$^{11a}$)$_2$, R$^{15}$, or R$^{16}$ substituents;

R$^{11a}$ is C$_1$-alkyl, C$_2$-alkyl, C$_3$-alkyl, C$_4$-alkyl, C$_5$-alkyl, C$_6$-alkyl, or R$^{11b}$;

R$^{11B}$ is C$_1$-alkyl, C$_2$-alkyl, C$_3$-alkyl, C$_4$-alkyl, C$_5$-alkyl, or C$_6$-alkyl, each of which is substituted with one or two independently selected —F, —Cl, —Br, —I, —OH, =O, —OR$^{11c}$, —NH$_2$, —NHR$^{11c}$, —N(R$^{11c}$)$_2$, or R$^{11d}$ substituents;

R$^{11c}$ is C$_1$-alkyl, C$_2$-alkyl, C$_3$-alkyl, C$_4$-alkyl, C$_5$-alkyl, or C$_6$-alkyl;

R$^{11d}$ is phenyl, furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl;

$R^{12}$ is phenyl which is unfused or fused with cyclopentane, cyclohexane, cyclopentene, cyclohexene, benzene, naphthylene, furan, imidazole, isothiazole, isoxazole, oxazole, pyrazine, pyrazole, pyridazine, pyridine, pyrimidine, pyrrole, thiazole, or thiophene, in which each ring is unsubstituted or substituted with one or two or three or four independently selected $R^{12a}$, —F, —Cl, —Br, —I, —CN, —OH, —$OR^{12a}$, —$NH_2$, —$NHR^{12a}$, —$N(R^{12a})_2$, —$NO_2$, —$CF_3$, —$OCF_3$, —$SR^{12a}$, —$S(O)R^{12a}$, —$SO_2R^{12a}$, —$C(O)R^{12a}$, —C(O)OH, —$C(O)OR^{12a}$, —$C(O)NH_2$, —$C(O)NHR^{12a}$, —$C(O)N(R^{12a})_2$, $R^{15}$, or $R^{16}$ substituents;

$R^{12a}$ is $C_1$-alkyl, $C_2$-alkyl, $C_3$-alkyl, $C_4$-alkyl, $C_5$-alkyl, $C_6$-alkyl, or $R^{12b}$;

$R^{12b}$ is $C_1$-alkyl, $C_2$-alkyl, $C_3$-alkyl, $C_4$-alkyl, $C_5$-alkyl, or $C_6$-alkyl, each of which is substituted with one or two independently selected —F, —Cl, —Br, —I, —OH, =O, —$OR^{12c}$, —$NH_2$, —$NHR^{12c}$, —$N(R^{12c})_2$, or $R^{12d}$ substituents;

$R^{12c}$ is $C_1$-alkyl, $C_2$-alkyl, $C_3$-alkyl, $C_4$-alkyl, $C_5$-alkyl, or $C_6$-alkyl;

$R^{12d}$ is phenyl, furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl;

$R^{13}$ is furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl, each of which is unfused or fused with benzene, naphthylene, furan, imidazole, isothiazole, isoxazole, oxazole, pyrazine, pyrazole, pyridazine, pyridine, pyrimidine, pyrrole, thiazole, or thiophene, in which each ring is unsubstituted or substituted with one or two or three independently selected $R^{13a}$, —F, —Cl, —Br, —I, —CN, —OH, —$OR^{13a}$, —$NH_2$, —$NHR^{13a}$, —$N(R^{13a})_2$, —$NO_2$, —$CF_3$, —$OCF_3$, —$SR^{13a}$, —$S(O)R^{13a}$, —$SO_2R^{13a}$, —$C(O)R^{13a}$, —C(O)OH, —$C(O)OR^{13a}$, —$C(O)NH_2$, —$C(O)NHR^{13a}$, —$C(O)N(R^{13a})_2$, $R^{15}$, or $R^{16}$ substituents;

$R^{13a}$ is $C_1$-alkyl, $C_2$-alkyl, $C_3$-alkyl, $C_4$-alkyl, $C_5$-alkyl, $C_6$-alkyl, or $R^{13b}$;

$R^{13b}$ is $C_1$-alkyl, $C_2$-alkyl, $C_3$-alkyl, $C_4$-alkyl, $C_5$-alkyl, or $C_6$-alkyl, each of which is substituted with one or two independently selected —F, —Cl, —Br, —I, —OH, =O, —$OR^{13c}$, —$NH_2$, —$NHR^{13c}$, —$N(R^{13c})_2$, or $R^{13d}$ substituents;

$R^{13c}$ is $C_1$-alkyl, $C_2$-alkyl, $C_3$-alkyl, $C_4$-alkyl, $C_5$-alkyl, or $C_6$-alkyl;

$R^{13d}$ is phenyl, furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl;

$R^{14}$ is aziridinyl, azetidinyl, pyrrolidinyl, piperidinyl, or piperazinyl, each of which is unfused or fused with benzene, aziridine, azetidine, pyrrolidine, piperidine, or piperazine, in which each ring is unsubstituted or substituted with one or two or three independently selected $R^{14a}$, —F, —Cl, —Br, —I, —CN, —OH, =O, —$OR^{14a}$, —$NH_2$, —$NHR^{14a}$, —$N(R^{14a})_2$, —$NO_2$, —$CF_3$, —$OCF_3$, —$SR^{14a}$, —$S(O)R^{14a}$, —$SO_2R^{14a}$, —$C(O)R^{14a}$, —C(O)OH, —$C(O)OR^{14a}$, —$C(O)NH_2$, —$C(O)NHR^{14a}$, —$C(O)N(R^{14a})_2$, $R^{15}$, or $R^{16}$ substituents;

$R^{14a}$ is $C_1$-alkyl, $C_2$-alkyl, $C_3$-alkyl, $C_4$-alkyl, $C_5$-alkyl, $C_6$-alkyl, or $R^{14b}$;

$R^{14b}$ is $C_1$-alkyl, $C_2$-alkyl, $C_3$-alkyl, $C_4$-alkyl, $C_5$-alkyl, or $C_6$-alkyl which is substituted with one or two independently selected —F, —Cl, —Br, —I, —OH, =O, —$OR^{14c}$, —$NH_2$, —$NHR^{14c}$, —$N(R^{14c})_2$, or $R^{14d}$ substituents;

$R^{14c}$ is $C_1$-alkyl, $C_2$-alkyl, $C_3$-alkyl, $C_4$-alkyl, $C_5$-alkyl, or $C_6$-alkyl;

$R^{14d}$ is phenyl, furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl;

$R^{15}$ is phenyl which is unsubstituted or substituted with one or two or three or four independently selected $R^{15a}$, —F, —Cl, —Br, —I, —CN, —OH, —$OR^{15a}$, —$NH_2$, —$NHR^{15a}$, —$N(R^{15a})_2$, —$NO_2$, —$CF_3$, —$OCF_3$, —$SR^{15a}$, —$S(O)R^{15a}$, —$SO_2R^{15a}$, —$C(O)R^{15a}$, —C(O)OH, —$C(O)OR^{15a}$, —$C(O)NH_2$, —$C(O)NHR^{15a}$, or —$C(O)N(R^{15a})_2$ substituents;

$R^{15a}$ is $C_1$-alkyl, $C_2$-alkyl, $C_3$-alkyl, $C_4$-alkyl, $C_5$-alkyl, or $C_6$-alkyl, or $R^{15b}$;

$R^{15b}$ is $C_1$-alkyl, $C_2$-alkyl, $C_3$-alkyl, $C_4$-alkyl, $C_5$-alkyl, or $C_6$-alkyl, each of which is substituted with one or two independently selected —F, —Cl, —Br, —I, —OH, =O, —$OR^{15c}$, —$NH_2$, —$NHR^{15c}$, —$N(R^{15c})_2$, or $R^{15d}$ substituents;

$R^{15c}$ is $C_1$-alkyl, $C_2$-alkyl, $C_3$-alkyl, $C_4$-alkyl, $C_5$-alkyl, or $C_6$-alkyl;

$R^{15d}$ is phenyl, furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl;

$R^{16}$ is furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl, each of which is unsubstituted or substituted with one or two or three independently selected $R^{16a}$, —F, —Cl, —Br, —I, —CN, —OH, —$OR^{16a}$, —$NH_2$, —$NHR^{16a}$, —$N(R^{16a})_2$, —$NO_2$, —$CF_3$, —$OCF_3$, —$SR^{16a}$, —$S(O)R^{16a}$, —$SO_2R^{16a}$, —$C(O)R^{16a}$, —C(O)OH, —$C(O)OR^{16a}$, —$C(O)NH_2$, —$C(O)NHR^{16a}$, or —$C(O)N(R^{16a})_2$ substituents;

$R^{16a}$ is $C_1$-alkyl, $C_2$-alkyl, $C_3$-alkyl, $C_4$-alkyl, $C_5$-alkyl, $C_6$-alkyl, or $R^{16b}$;

$R^{16b}$ is $C_1$-alkyl, $C_2$-alkyl, $C_3$-alkyl, $C_4$-alkyl, $C_5$-alkyl, or $C_6$-alkyl, each of which is substituted with one or two independently selected —F, —Cl, —Br, —I, —OH, —$OR^{16c}$, =O, —$NH_2$, —$NHR^{16c}$, —$N(R^{16c})_2$, or $R^{16d}$ substituents;

$R^{16c}$ is $C_1$-alkyl, $C_2$-alkyl, $C_3$-alkyl, $C_4$-alkyl, $C_5$-alkyl, or $C_6$-alkyl; and $R^{16d}$ is phenyl, furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl.

2. A compound of claim 1 having formula (I), or a salt thereof, in which $R^1$ is —OH, —$OR^5$, —$NH_2$, —$NHR^5$, or —$N(R^5)_2$;

$R^2$ is hydrogen, tert-butyl, —O(allyl), (4-methoxyphenyl)methyl, or (2,4-dimethoxyphenyl)methyl;

$R^3$ and $R^4$ together are thiazole which is substituted with one or two independently selected $R^6$, $R^9$, $R^{10}$, $R^{11}$, —$OR^6$, —$OR^9$, —$O(CH_2)R^{10}$, —$O(CH_2)R^{11}$, —$SR^6$, —$SR^9$, —$S(CH_2)R^{10}$, —$S(CH_2)R^{11}$, —$S(O)R^6$, —$S(O)R^9$, —$S(O)(CH_2)R^{10}$, —$S(O)(CH_2)R^{11}$, —$SO_2R^6$, —$SO_2R^9$, —$SO_2(CH_2)R^{10}$, —$SO_2(CH_2)R^{11}$, —$CO(O)R^6$, —$CO(O)R^9$, —$C(O)OR^{10}$, —$C(O)OR^{11}$, —$NH_2$, —$NHR^6$, —$NHR^9$, —$NHR^{10}$, —$NHR^{11}$, —$NHC(O)R^6$, —$NHC(O)R^9$, —$NHC(O)R^{10}$, —$NHC(O)R^{11}$, —$NHC(O)OR^6$, —$NHC(O)OR^9$, —NHC(O)

OR$^{10}$, —NHC(O)OR$^{11}$, —NHSO$_2$R$^6$, —NHSO$_2$R$^9$, —NHSO$_2$R$^{10}$, —NHSO$_2$R$^{11}$, —N(R$^6$)$_2$, —N(R$^9$)$_2$, —N(R$^{10}$)$_2$, or —N(R$^{11}$)$_2$ substituents;

R$^5$ is C$_1$-alkyl, C$_2$-alkyl, C$_3$-alkyl, C$_4$-alkyl, C$_5$-alkyl, or C$_6$-alkyl;

R$^6$ is C$_1$-alkyl, C$_2$-alkyl, C$_3$-alkyl, C$_4$-alkyl, C$_5$-alkyl, or C$_6$-alkyl, each of which is unsubstituted or substituted with one —F, —Cl, —Br, —I, —OH, —OR$^{6a}$, —NH$_2$, —NHR$^{6a}$, —N(R$^{6a}$)$_2$, R$^{12}$, R$^{13}$, or R$^{14}$ substituent;

R$^{6a}$ is C$_1$-alkyl, C$_2$-alkyl, C$_3$-alkyl, C$_4$-alkyl, C$_5$-alkyl, C$_6$-alkyl, or R$^{6b}$;

R$^{6b}$ is C$_1$-alkyl, C$_2$-alkyl, C$_3$-alkyl, C$_4$-alkyl, C$_5$-alkyl, or C$_6$-alkyl, each of which is substituted with one or two independently selected —F, —Cl, —Br, —I, —OH, =O, —OR$^{6c}$, —NH$_2$, —NHR$^{6c}$, or —N(R$^{6c}$)$_2$ substituents;

R$^{6c}$ is C$_1$-alkyl, C$_2$-alkyl, C$_3$-alkyl, C$_4$-alkyl, C$_5$-alkyl, or C$_6$-alkyl;

R$^9$ is phenyl which is unsubstituted or substituted with one or two or three or four independently selected R$^{9a}$, —F, —Cl, —Br, —I, —CN, —OH, —OR$^{9a}$, —NH$_2$, —NHR$^{9a}$, —N(R$^{9a}$)$_2$, —NO$_2$, —CF$_3$, —OCF$_3$, —SR$^{9a}$, —S(O)R$^{9a}$, —SO$_2$R$^{9a}$, —C(O)R$^{9a}$, —C(O)OH, —C(O)OR$^{9a}$, —C(O)NH$_2$, —C(O)NHR$^{9a}$, —C(O)N(R$^{9a}$)$_2$, R$^{15}$, or R$^{16}$ substituents;

R$^{9a}$ is C$_1$-alkyl, C$_2$-alkyl, C$_3$-alkyl, C$_4$-alkyl, C$_5$-alkyl, or C$_6$-alkyl, or R$^{9b}$;

R$^{9b}$ is C$_1$-alkyl, C$_2$-alkyl, C$_3$-alkyl, C$_4$-alkyl, C$_5$-alkyl, or C$_6$-alkyl, each of which is substituted with one or two independently selected —F, —Cl, —Br, —I, —OH, =O, —OR$^{9c}$, —NH$_2$, —NHR$^{9c}$, or —N(R$^{9c}$)$_2$ substituents;

R$^{9c}$ is C$_1$-alkyl, C$_2$-alkyl, C$_3$-alkyl, C$_4$-alkyl, C$_5$-alkyl, or C$_6$-alkyl;

R$^{10}$ is furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl, each of which is unsubstituted or substituted with one or two or three independently selected R$^{10a}$, —F, —Cl, —Br, —I, —CN, —OH, —OR$^{10a}$, —NH$_2$, —NHR$^{10a}$, —N(R$^{10a}$)$_2$, —NO$_2$, —CF$_3$, —OCF$_3$, —SR$^{10a}$, —S(O)R$^{10a}$, —SO$_2$R$^{10a}$, —C(O)R$^{10a}$, —C(O)OH, —C(O)OR$^{10a}$, —C(O)NH$_2$, —C(O)NHR$^{10a}$, —C(O)N(R$^{10a}$)$_2$, R$^{15}$ or R$^{16}$ substituents;

R$^{10a}$ is C$_1$-alkyl, C$_2$-alkyl, C$_3$-alkyl, C$_4$-alkyl, C$_5$-alkyl, C$_6$-alkyl, or R$^{10b}$;

R$^{10b}$ is C$_1$-alkyl, C$_2$-alkyl, C$_3$-alkyl, C$_4$-alkyl, C$_5$-alkyl, or C$_6$-alkyl, each of which is substituted with one or two independently selected —F, —Cl, —Br, —I, —OH, =O, —OR$^{10c}$, —NH$_2$, —NHR$^{10c}$, or N(R$^{10c}$)$_2$, substituents;

R$^{10c}$ is C$_1$-alkyl, C$_2$-alkyl, C$_3$-alkyl, C$_4$-alkyl, C$_5$-alkyl, or C$_6$-alkyl;

R$^{11}$ is aziridinyl, azetidinyl, pyrrolidinyl, piperidinyl, or piperazinyl, each of which is unfused or fused with benzene, aziridine, azetidine, pyrrolidine, piperidine, or piperazine, each of which is unsubstituted or substituted with one or two or three independently selected R$^{11a}$, —F, —Cl, —Br, —I, —CN, —OH, =O, —OR$^{11a}$, —NH$_2$, —NHR$^{11a}$, —N(R$^{11a}$)$_2$, —NO$_2$, —CF$_3$, —OCF$_3$, —SR$^{11a}$, —S(O)R$^{11a}$, —SO$_2$R$^{11a}$, —C(O)R$^{11a}$, —C(O)OH, —C(O)OR$^{11a}$, —C(O)NH$_2$, —C(O)NHR$^{11a}$, —C(O)N(R$^{11a}$)$_2$, R$^{15}$ or R$^{16}$ substituents;

R$^{11a}$ is C$_1$-alkyl, C$_2$-alkyl, C$_3$-alkyl, C$_4$-alkyl, C$_5$-alkyl, C$_6$-alkyl, or R$^{11b}$;

R$^{11B}$ is C$_1$-alkyl, C$_2$-alkyl, C$_3$-alkyl, C$_4$-alkyl, C$_5$-alkyl, or C$_6$-alkyl, each of which is substituted with one or two independently selected —F, —Cl, —Br, —I, —OH, =O, —OR$^{11c}$, —NH$_2$, —NHR$^{11c}$, or —N(R$^{11c}$)$_2$, substituents;

R$^{11c}$ is C$_1$-alkyl, C$_2$-alkyl, C$_3$-alkyl, C$_4$-alkyl, C$_5$-alkyl, or C$_6$-alkyl;

R$^{12}$ is phenyl which is unsubstituted or substituted with one or two or three or four independently selected R$^{12a}$, —F, —Cl, —Br, —I, —CN, —OH, —OR$^{12a}$, —NH$_2$, —NHR$^{12a}$, —N(R$^{12a}$)$_2$, —NO$_2$, —CF$_3$, —OCF$_3$, —SR$^{12a}$, —S(O)R$^{12a}$, —SO$_2$R$^{12a}$, —C(O)R$^{12a}$, —C(O)OH, —C(O)OR$^{12a}$, —C(O)NH$_2$, —C(O)NHR$^{12a}$, —C(O)N(R$^{12a}$)$_2$, R$^{15}$, or R$^{16}$ substituents;

R$^{12a}$ is C$_1$-alkyl, C$_2$-alkyl, C$_3$-alkyl, C$_4$-alkyl, C$_5$-alkyl, or C$_6$-alkyl, or R$^{12b}$;

R$^{12b}$ is C$_1$-alkyl, C$_2$-alkyl, C$_3$-alkyl, C$_4$-alkyl, C$_5$-alkyl, or C$_6$-alkyl, each of which is substituted with one or two independently selected —F, —Cl, —Br, —I, —OH, =O, —OR$^{12c}$, —NH$_2$, —NHR$^{12c}$, or —N(R$^{12c}$)$_2$ substituents;

R$^{12c}$ is C$_1$-alkyl, C$_2$-alkyl, C$_3$-alkyl, C$_4$-alkyl, C$_5$-alkyl, or C$_6$-alkyl;

R$^{13}$ is furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl, each of which is unsubstituted or substituted with one or two or three independently selected R$^{13a}$, —F, —Cl, —Br, —I, —CN, —OH, —OR$^{13a}$, —NH$_2$, —NHR$^{13a}$, —N(R$^{13a}$)$_2$, —NO$_2$, —CF$_3$, —OCF$_3$, —SR$^{13a}$, —S(O)R$^{13a}$, —SO$_2$R$^{13a}$, —C(O)R$^{13a}$, —C(O)OH, —C(O)OR$^{13a}$, —C(O)NH$_2$, —C(O)NHR$^{13a}$, —C(O)N(R$^{13a}$)$_2$, R$^{15}$, or R$^{16}$ substituents;

R$^{13a}$ is C$_1$-alkyl, C$_2$-alkyl, C$_3$-alkyl, C$_4$-alkyl, C$_5$-alkyl, C$_6$-alkyl, or R$^{13b}$;

R$^{13b}$ is C$_1$-alkyl, C$_2$-alkyl, C$_3$-alkyl, C$_4$-alkyl, C$_5$-alkyl, or C$_6$-alkyl, each of which is substituted with one or two independently selected —F, —Cl, —Br, —I, —OH, =O, —OR$^{13c}$, —NH$_2$, —NHR$^{13c}$ or —N(R$^{13c}$)$_2$ substituents;

R$^{13c}$ is C$_1$-alkyl, C$_2$-alkyl, C$_3$-alkyl, C$_4$-alkyl, C$_5$-alkyl, or C$_6$-alkyl;

R$^{14}$ is aziridinyl, azetidinyl, pyrrolidinyl, piperidinyl, or piperazinyl, each of which is unsubstituted or substituted with one or two or three independently selected R$^{14a}$, —F, —Cl, —Br, —I, —CN, —OH, =O, —OR$^{14a}$, —NH$_2$, —NHR$^{14a}$, —N(R$^{14a}$)$_2$, —NO$_2$, —CF$_3$, —OCF$_3$, —SR$^{14a}$, —S(O)R$^{14a}$, —SO$_2$R$^{14a}$, —C(O)R$^{14a}$, —C(O)OH, —C(O)OR$^{14a}$, —C(O)NH$_2$, —C(O)NHR$^{14a}$, —C(O)N(R$^{14a}$)$_2$, R$^{16}$ or R$^{17}$ substituents;

R$^{14a}$ is C$_1$-alkyl, C$_2$-alkyl, C$_3$-alkyl, C$_4$-alkyl, C$_5$-alkyl, C$_6$-alkyl, or R$^{14b}$;

R$^{14b}$ is C$_1$-alkyl, C$_2$-alkyl, C$_3$-alkyl, C$_4$-alkyl, C$_5$-alkyl, or C$_6$-alkyl which is substituted with one or two independently selected —F, —Cl, —Br, —I, —OH, =O, —OR$^{14c}$, —NH$_2$, —NHR$^{14c}$, or —N(R$^{14c}$)$_2$, substituents;

R$^{14c}$ is C$_1$-alkyl, C$_2$-alkyl, C$_3$-alkyl, C$_4$-alkyl, C$_5$-alkyl, or C$_6$-alkyl;

R$^{15}$ is phenyl which is unsubstituted or substituted with one or two or three or four independently selected R$^{15a}$, —F, —Cl, —Br, —I, —CN, —OH, —OR$^{15a}$, —NH$_2$, —NHR$^{15a}$ —N(R$^{15a}$)$_2$, —NO$_2$, —CF$_3$, —OCF$_3$, —SR$^{15a}$, —S(O)R$^{15a}$, —SO$_2$R$^{15a}$, —C(O)R$^{15a}$, —C(O)OH, —C(O)OR$^{15a}$, —C(O)NH$_2$, —C(O)NHR$^{15a}$, or —C(O)N(R$^{15a}$)$_2$ substituents;

R$^{15a}$ is C$_1$-alkyl, C$_2$-alkyl, C$_3$-alkyl, C$_4$-alkyl, C$_5$-alkyl, C$_6$-alkyl, or R$^{15b}$;

R$^{15b}$ is C$_1$-alkyl, C$_2$-alkyl, C$_3$-alkyl, C$_4$-alkyl, C$_5$-alkyl, or C$_6$-alkyl which is substituted with one or two independently selected —F, —Cl, —Br, —I, —OH, =O, —OR$^{15c}$, —NH$_2$, —NHR$^{15c}$, or —N(R$^{15c}$)$_2$ substituents;

R$^{15c}$ is C$_1$-alkyl, C$_2$-alkyl, C$_3$-alkyl, C$_4$-alkyl, C$_5$-alkyl, or C$_6$-alkyl;

R$^{16}$ is furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl, each of which is unsubstituted or substituted with one or two or three independently selected R$^{16a}$, —F, —Cl, —Br, —I, —CN, —OH, —OR$^{16a}$, —NH$_2$, —NHR$^{16a}$, —N(R$^{16a}$)$_2$, —NO$_2$, —CF$_3$, —OCF$_3$, —SR$^{16a}$, —S(O)R$^{16a}$, —SO$_2$R$^{16a}$, —C(O)R$^{16a}$, —C(O)OH, —C(O)OR$^{16a}$, —C(O)NH$_2$, —C(O)NHR$^{16a}$, or —C(O)N(R$^{16a}$)$_2$ substituents;

R$^{16a}$ is C$_1$-alkyl, C$_2$-alkyl, C$_3$-alkyl, C$_4$-alkyl, C$_5$-alkyl, C$_6$-alkyl, or R$^{16b}$;

R$^{16b}$ is C$_1$-alkyl, C$_2$-alkyl, C$_3$-alkyl, C$_4$-alkyl, C$_5$-alkyl, or C$_6$-alkyl, each of which is substituted with one or two independently selected —F, —Cl, —Br, —I, —OH, —OR$^{16c}$, =O, —NH$_2$, —NHR$^{16c}$, or —N(R$^{16c}$)$_2$ substituents; and R$^{16c}$ is C$_1$-alkyl, C$_2$-alkyl, C$_3$-alkyl, C$_4$-alkyl, C$_5$-alkyl, or C$_6$-alkyl.

3. A compound of claim 2 having formula (I), or a salt thereof, in which R$^1$ is —OH, —OR$^5$, —NH$_2$, —NHR$^5$, or —N(R$^5$)$_2$;

R$^2$ is hydrogen, tert-butyl, —O(allyl), (4-methoxyphenyl)methyl, or (2,4-dimethoxyphenyl)methyl;

R$^3$ and R$^4$ together are thiazole which is substituted with one or two independently selected R$^6$, R$^9$, R$^{11}$, —OR$^6$, —OR$^9$, —O(CH$_2$)R$^{11}$, —SR$^6$, —SR$^9$, —S(CH$_2$)R$^{11}$, —S(O)R$^6$, —S(O)R$^9$, —S(O)(CH$_2$)R$^{11}$, —SO$_2$R$^6$, —SO$_2$R$^9$, —SO$_2$(CH$_2$)R$^{11}$, —CO(O)R$^6$, —CO(O)R$^9$, —C(O)OR$^{11}$, —NH$_2$, —NHR$^6$, —NHR$^9$, —NHR$^{11}$, —NHC(O)R$^6$, —NHC(O)R$^9$, —NHC(O)R$^{11}$, —NHC(O)OR$^6$, —NHC(O)OR$^9$, —NHC(O)OR$^{11}$, —NHSO$_2$R$^6$, —NHSO$_2$R$^9$, —NHSO$_2$R$^{11}$, —N(R$^6$)$_2$, —N(R$^9$)$_2$, or —N(R$^{11}$)$_2$ substituents;

R$^5$ is C$_1$-alkyl, C$_2$-alkyl, C$_3$-alkyl, C$_4$-alkyl, C$_5$-alkyl, or C$_6$-alkyl;

R$^6$ is C$_1$-alkyl, C$_2$-alkyl, C$_3$-alkyl, C$_4$-alkyl, C$_5$-alkyl, or C$_6$-alkyl, each of which is unsubstituted or substituted with one —F, —Cl, —Br, —I, —OH, —OR$^{6a}$, —NH$_2$, —NHR$^{6a}$, —N(R$^{6a}$)$_2$, R$^{12}$, R$^{13}$, or R$^{14}$ substituent;

R$^{6a}$ is C$_1$-alkyl, C$_2$-alkyl, C$_3$-alkyl, C$_4$-alkyl, C$_5$-alkyl, or C$_6$-alkyl;

R$^9$ is phenyl which is unsubstituted or substituted with one or two or three or four independently selected R$^{9a}$, —F, —Cl, —Br, —I, —CN, —OH, —OR$^{9a}$, —NH$_2$, —NHR$^{9a}$, —N(R$^{9a}$)$_2$, —NO$_2$, —CF$_3$, —OCF$_3$, —SR$^{9a}$, —S(O)R$^{9a}$, —SO$_2$R$^{9a}$, —C(O)R$^{9a}$, —C(O)OH, —C(O)OR$^{9a}$, —C(O)NH$_2$, —C(O)NHR$^{9a}$, —C(O)N(R$^{9a}$)$_2$, R$^{15}$, or R$^{16}$ substituents;

R$^{9a}$ is C$_1$-alkyl, C$_2$-alkyl, C$_3$-alkyl, C$_4$-alkyl, C$_5$-alkyl, or C$_6$-alkyl;

R$^{10}$ is furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl, each of which is unsubstituted or substituted with one or two or three independently selected R$^{10a}$, —F, —Cl, —Br, —I, —CN, —OH, —OR$^{10a}$, —NH$_2$, —NHR$^{10a}$, —N(R$^{10a}$)$_2$, —NO$_2$, —CF$_3$, —OCF$_3$, —SR$^{10a}$, —S(O)R$^{10a}$, —SO$_2$R$^{10a}$, —C(O)R$^{10a}$, —C(O)OH, —C(O)OR$^{10a}$, —C(O)NH$_2$, —C(O)NHR$^{10a}$, —C(O)N(R$^{10a}$)$_2$, R$^{15}$, or R$^{16}$ substituents;

R$^{10a}$ is C$_1$-alkyl, C$_2$-alkyl, C$_3$-alkyl, C$_4$-alkyl, C$_5$-alkyl, or C$_6$-alkyl;

R$^{11}$ is aziridinyl, azetidinyl, pyrrolidinyl, piperidinyl, or piperazinyl, each of which is unfused or fused with benzene, aziridine, azetidine, pyrrolidine, piperidine, or piperazine, in which each ring is unsubstituted or substituted with one or two or three independently selected R$^{11a}$, —F, —Cl, —Br, —I, —CN, —OH, =O, —OR$^{11a}$, —NH$_2$, —NHR$^{11a}$, —N(R$^{11a}$)$_2$, —NO$_2$, —CF$_3$, —OCF$_3$, —SR$^{11a}$, —S(O)R$^{11a}$, —SO$_2$R$^{11a}$, —C(O)R$^{11a}$, —C(O)OH, —C(O)OR$^{11a}$, —C(O)NH$_2$, —C(O)NHR$^{11a}$, —C(O)N(R$^{11a}$)$_2$, R$^{15}$, or R$^{16}$ substituents;

R$^{11a}$ is C$_1$-alkyl, C$_2$-alkyl, C$_3$-alkyl, C$_4$-alkyl, C$_5$-alkyl, C$_6$-alkyl, or R$^{11b}$;

R$^{11B}$ is C$_1$-alkyl, C$_2$-alkyl, C$_3$-alkyl, C$_4$-alkyl, C$_5$-alkyl, or C$_6$-alkyl, each of which is substituted with one or two independently selected —F, —Cl, —Br, —I, —OH, =O, —OR$^{11c}$, —NH$_2$, NHR$^{11c}$, or —N(R$^{11c}$)$_2$, substituents;

R$^{11c}$ is C$_1$-alkyl, C$_2$-alkyl, C$_3$-alkyl, C$_4$-alkyl, C$_5$-alkyl, or C$_6$-alkyl;

R$^{12}$ is phenyl which is unsubstituted or substituted with one or two or three or four independently selected R$^{12a}$, —F, —Cl, —Br, —I, —CN, —OH, —OR$^{12a}$, —NH$_2$, —NHR$^{12a}$, —N(R$^{12a}$)$_2$, —NO$_2$, —CF$_3$, —OCF$_3$, —SR$^{12a}$, —S(O)R$^{12a}$, —SO$_2$R$^{12a}$, —C(O)R$^{12a}$, —C(O)OH, —C(O)OR$^{12a}$, —C(O)NH$_2$, —C(O)NHR$^{12a}$, —C(O)N(R$^{12a}$)$_2$, R$^{15}$, or R$^{16}$ substituents;

R$^{12a}$ is C$_1$-alkyl, C$_2$-alkyl, C$_3$-alkyl, C$_4$-alkyl, C$_5$-alkyl, or C$_6$-alkyl;

R$^{13}$ is furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl, each of which is unsubstituted or substituted with one or two or three independently selected R$^{13a}$, —F, —Cl, —Br, —I, —CN, —OH, —OR$^{13a}$, —NH$_2$, —NHR$^{13a}$, —N(R$^{13a}$)$_2$, —NO$_2$, —CF$_3$, —OCF$_3$, —SR$^{13a}$, —S(O)R$^{13a}$, —SO$_2$R$^{13a}$, —C(O)R$^{13a}$, —C(O)OH, —C(O)OR$^{13a}$, —C(O)NH$_2$, —C(O)NHR$^{13a}$, —C(O)N(R$^{13a}$)$_2$, R$^{15}$, or R$^{16}$ substituents;

R$^{13a}$ is C$_1$-alkyl, C$_2$-alkyl, C$_3$-alkyl, C$_4$-alkyl, C$_5$-alkyl, or C$_6$-alkyl;

R$^{14}$ is aziridinyl, azetidinyl, pyrrolidinyl, piperidinyl, or piperazinyl, each of which is unsubstituted or substituted with one or two or three independently selected R$^{14a}$, —F, —Cl, —Br, —I, —CN, —OH, =O, —OR$^{14a}$, —NH$_2$, —NHR$^{14a}$, —N(R$^{14a}$)$_2$, —NO$_2$, —CF$_3$, —OCF$_3$, —SR$^{14a}$, —S(O)R$^{14a}$, —SO$_2$R$^{14a}$, —C(O)R$^{14a}$, —C(O)OH, —C(O)OR$^{14a}$, —C(O)NH$_2$, —C(O)NHR$^{14a}$, —C(O)N(R$^{14a}$)$_2$, R$^{16}$, or R$^{17}$ substituents;

R$^{14a}$ is C$_1$-alkyl, C$_2$-alkyl, C$_3$-alkyl, C$_4$-alkyl, C$_5$-alkyl, or C$_6$-alkyl;

R$^{15}$ is phenyl which is unsubstituted or substituted with one or two or three or four independently selected R$^{15a}$, —F, —Cl, —Br, —I, —CN, —OH, —OR$^{15a}$, —NH$_2$, —NHR$^{15a}$, —N(R$^{15a}$)$_2$, —NO$_2$, —CF$_3$, —OCF$_3$, —SR$^{15a}$, —S(O)R$^{15a}$, —SO$_2$R$^{15a}$, —C(O)R$^{15a}$, —C(O)OH, —C(O)OR$^{15a}$, —C(O)NH$_2$, —C(O)NHR$^{15a}$, or —C(O)N(R$^{15a}$)$_2$ substituents;

R$^{15a}$ is C$_1$-alkyl, C$_2$-alkyl, C$_3$-alkyl, C$_4$-alkyl, C$_5$-alkyl, or C$_6$-alkyl;

R$^{16}$ is furanyl, imidazolyl, isothiazolyl, isoxazolyl, oxazolyl, pyrazinyl, pyrazolyl, pyridazinyl, pyridyl, pyrimidinyl, pyrrolyl, tetraäzolyl, thiazolyl, thiophenyl, or 1,2,3-triazolyl, each of which is unsubstituted or substituted with one or two or three independently selected R$^{16a}$, —F, —Cl, —Br, —I, —CN, —OH, —OR$^{16a}$, —NH$_2$, —NHR$^{16a}$, —N(R$^{16a}$)$_2$, —NO$_2$, —CF$_3$, —OCF$_3$, —SR$^{16a}$, —S(O)R$^{16a}$, —SO$_2$R$^{16a}$, —C(O)R$^{16a}$, —C(O)OH, —C(O)OR$^{16a}$, —C(O)NH$_2$, —C(O)NHR$^{16a}$, or —C(O)N(R$^{16a}$)$_2$ substituents; and R$^{16a}$ is C$_1$-alkyl, C$_2$-alkyl, C$_3$-alkyl, C$_4$-alkyl, C$_5$-alkyl, or C$_6$-alkyl.

4. A compound of claim 1 having formula (I), or a salt thereof, in which R$^1$ is —OH or —O(ethyl); R$^2$ is hydrogen; and R$^3$ and R$^4$ together are 2-(aminomethyl)-piperidin-1-yl[1,3]thiazolo, 2-(amino-methyl)pyrrolidin-1-yl[1,3]thiazolo, 3-aminopiperidin-1-yl[1,3]thiazolo, 4-bromo-3-methyl-anilino[1,3]thiazolo, 4-(2-chlorophenyl)piperazin-1-yl[1,3]thiazolo, ((3,4-dimethoxyphenyl)ethyl)(methyl)amino[1,3]thiazolo, 2-fluoro-4-methylanilino[1,3]thiazolo, or 3-fluoro-4-methylanilino[1,3]thiazolo.

5. A compound of claim 1 having formula (I), or a salt thereof, in which R$^1$ is —OH or —O(ethyl); R$^2$ is hydrogen; and R$^3$ and R$^4$ together are together are 4-(2-fluorophenyl)piperazin-1-yl[1,3]thiazolo, 1H-indazol-4-ylamino[1,3]thiazolo, methyl(2-phenylethyl) amino-[1,3]thiazolo, 4-(methylsulfanyl)anilino-[1,3] thiazolo, 4-propoxyanilino[1,3]thiazolo, or pyrrolidin-1-yl[1,3] thiazolo.

6. A composition for treating bacterial infection in a fish or a mammal, the composition comprising a therapeutically effective amount of a compound of claim 1 and an excipient.

7. A compound of claim 1 having formula (I), or a salt thereof, which is 2-(3-(aminomethyl)pyrrolidin-1-yl)-4-(4-methoxy-benzyl)-7-oxo-4,7-dihydro[1,3]thiazolo[4,5-b]pyridine-6-carboxylic acid, 2-(3-aminopiperidin-1-yl)-7-oxo-4,7-dihydro[1,3]thiazolo[4,5-b]pyridine-6-carboxylic acid, 2-(3-(aminomethyl)piperidin-1-yl)-7-oxo-4,7-dihydro[1,3]thiazolo[4,5-b]pyridine-6-carboxylic acid, 2-(methyl(2-phenylethyl)amino)-7-oxo-4,7-dihydro[1,3] thiazolo[4,5-b]pyridine-6-carboxylic acid, 2-((2-(3,4-dimethoxyphenyl)ethyl)(methyl)amino)-7-oxo-4,7-dihydro[1,3]thiazolo[4,5-b]pyridine-6-carboxylic acid, 2-(4-(2-fluorophenyl)piperazin-1-yl)-7-oxo-4,7-dihydro [1,3]thiazolo[4,5-b]pyridine-6-carboxylic acid, 2-(4-(2-chlorophenyl)piperazin-1-yl)-7-oxo-4,7-dihydro [1,3]thiazolo[4,5-b]pyridine-6-carboxylic acid, 2-(2-fluoro-4-methylanilino)-7-oxo-4,7-dihydro[1,3]thiazolo[4,5-b]pyridine-6-carboxylic acid, 2-(3-fluoro-4-methylanilino)-7-oxo-4,7-dihydro[1,3]thiazolo[4,5-b]pyridine-6-carboxylic acid, 2-(4-bromo-3-methylanilino)-7-oxo-4,7-dihydro[1,3] thiazolo[4,5-b]pyridine-6-carboxylic acid 7-oxo-2-(4-propoxyanilino)-4,7-dihydro[1,3]thiazolo[4,5-b]pyridine-6-carboxylic acid or 2-(4-(methylsulfanyl)anilino)-7-oxo-4,7-dihydro[1,3] thiazolo[4,5-b]pyridine-6-carboxylic acid.

\* \* \* \* \*